United States Patent
Canafax et al.

(10) Patent No.: US 11,510,892 B2
(45) Date of Patent: *Nov. 29, 2022

(54) PHARMACOKINETICS OF COMBINED RELEASE FORMULATIONS OF A γ-HYDROXYBUTYRIC ACID DERIVATIVE

(71) Applicant: XWPHARMA LTD., Grand Cayman (KY)

(72) Inventors: Daniel M. Canafax, Half Moon Bay, CA (US); William W. Xiang, Fremont, CA (US); Leonard Blum, Edina, MN (US); Jia-Ning Xiang, Fremont, CA (US)

(73) Assignee: XWPHARMA LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/698,609

(22) Filed: Mar. 18, 2022

(65) Prior Publication Data

US 2022/0304969 A1    Sep. 29, 2022

Related U.S. Application Data

(60) Provisional application No. 63/163,096, filed on Mar. 19, 2021.

(51) Int. Cl.
 *A61K 31/22* (2006.01)
 *A61K 9/00* (2006.01)
 *A61K 9/48* (2006.01)
 *A61K 9/50* (2006.01)

(52) U.S. Cl.
 CPC ............ *A61K 31/22* (2013.01); *A61K 9/0053* (2013.01); *A61K 9/485* (2013.01); *A61K 9/4866* (2013.01); *A61K 9/5047* (2013.01)

(58) Field of Classification Search
 CPC ...... A61K 31/22; A61K 9/0053; A61K 9/485; A61K 9/4866; A61K 9/5047
 See application file for complete search history.

(56) References Cited

U.S. PATENT DOCUMENTS

| | | | |
|---|---|---|---|
| 4,370,338 A | 1/1983 | Mizoule | |
| 5,110,797 A | 5/1992 | Ienaga et al. | |
| 6,489,350 B1 | 12/2002 | Benedyk et al. | |
| 7,482,429 B2 | 1/2009 | Albericio et al. | |
| 7,521,455 B2 | 4/2009 | Nagase et al. | |
| 7,960,561 B2 | 6/2011 | Sorensen et al. | |
| 8,529,954 B2 | 9/2013 | Lebon et al. | |
| 8,598,191 B2 | 12/2013 | Liang et al. | |
| 9,309,182 B2 | 4/2016 | Tung et al. | |
| 10,398,662 B1 | 9/2019 | Allphin et al. | |
| 10,457,627 B2 | 10/2019 | Xiang et al. | |
| 10,501,401 B2 | 12/2019 | Xiang et al. | |
| 10,640,451 B2 | 5/2020 | Xiang et al. | |
| 10,774,031 B2 | 9/2020 | Xiang et al. | |
| 11,395,801 B2 | 7/2022 | Karaborni et al. | |
| 2004/0214755 A1 | 10/2004 | Albericio et al. | |
| 2005/0182045 A1 | 8/2005 | Nagase et al. | |
| 2006/0122383 A1 | 6/2006 | Zhou et al. | |
| 2006/0210630 A1 | 9/2006 | Liang et al. | |
| 2007/0134315 A1 | 6/2007 | Viera et al. | |
| 2008/0175873 A1 | 7/2008 | Zhou et al. | |
| 2010/0144869 A1 | 6/2010 | Nudelman et al. | |
| 2011/0111027 A1 | 5/2011 | Rourke et al. | |
| 2011/0178068 A1 | 7/2011 | Almarsson et al. | |
| 2011/0293729 A1 | 12/2011 | Lebon et al. | |
| 2012/0283300 A1 | 11/2012 | Kim et al. | |
| 2016/0052862 A1 | 2/2016 | Frost et al. | |
| 2018/0021284 A1 | 1/2018 | Megret et al. | |
| 2018/0193277 A1 | 7/2018 | Suplie et al. | |
| 2019/0183806 A1 | 6/2019 | Guillard | |
| 2020/0009076 A1 | 1/2020 | Patel et al. | |
| 2020/0223783 A1 | 7/2020 | Xiang et al. | |
| 2020/0276142 A1 | 9/2020 | Grassot et al. | |
| 2022/0023247 A1 | 1/2022 | Xiang et al. | |
| 2022/0105044 A1 | 4/2022 | Karaborni et al. | |

FOREIGN PATENT DOCUMENTS

| | | |
|---|---|---|
| CN | 1422278 | 6/2003 |
| CN | 101511388 | 8/2009 |
| CN | 102076342 | 5/2011 |
| CN | 102834098 | 12/2012 |
| CN | 103370289 | 10/2013 |
| DE | 852392 | 10/1952 |
| EP | 0635265 | 1/1995 |
| EP | 2566462 | 3/2013 |
| FR | 2662695 | 12/1991 |
| JP | 62-270552 | 11/1987 |
| JP | 2002-503673 | 2/2002 |

(Continued)

OTHER PUBLICATIONS

International Search Report and Written Opinion for International Application No. PCT/CN2016/099763, dated Jan. 3, 2017, 15 pages.
International Search Report and Written Opinion for International Application No. PCT/CN2017/078873, dated Jan. 9, 2018, 12 pages.
International Search Report and Written Opinion for International Application No. PCT/CN2018/090151, dated Feb. 20, 2019, 14 pages.
International Search Report and Written Opinion for International Application No. PCT/CN2018/097241, dated Apr. 28, 2019, 11 pages.
International Search Report and Written Opinion for International Application No. PCT/CN2018/109115, dated Jul. 8, 2019, 11 pages.
International Search Report and Written Opinion for International Application No. PCT/CN2018/118565, dated Jul. 8, 2019, Apr. 28, 2019, 13 pages.

(Continued)

*Primary Examiner* — Robert A Wax
*Assistant Examiner* — Olga V. Tcherkasskaya

(57) ABSTRACT

Pharmaceutical compositions comprising an immediate release component comprising 4-((L-valyl)oxy)butanoic acid and a modified release component comprising 4-((L-valyl)oxy)butanoic acid and the pharmacokinetics of 4-((L-valyl)oxy)butanoic acid and γ-hydroxybutyrate following oral administration of the pharmaceutical compositions is disclosed.

15 Claims, 5 Drawing Sheets

(56) References Cited

FOREIGN PATENT DOCUMENTS

| | | |
|---|---|---|
| JP | 2003-522198 | 7/2003 |
| JP | 2004059452 | 2/2004 |
| JP | 2008-526713 | 7/2008 |
| JP | 2013-516465 | 5/2013 |
| RU | 2142800 | 12/1999 |
| WO | 1999/041275 | 8/1999 |
| WO | 1999/051613 | 10/1999 |
| WO | 2004/087169 | 10/2004 |
| WO | 2005/123731 | 12/2005 |
| WO | 2006/038226 | 4/2006 |
| WO | 2009/040331 | 4/2009 |
| WO | 2009/102462 | 8/2009 |
| WO | 2009/137717 | 11/2009 |
| WO | 2010/124046 | 10/2010 |
| WO | 2011/119839 | 9/2011 |
| WO | 2013/019561 | 2/2013 |
| WO | 2013/163244 | 10/2013 |
| WO | 2014/031840 | 2/2014 |
| WO | 2014/078014 | 5/2014 |
| WO | 2014/152263 | 9/2014 |
| WO | 2014/205393 | 12/2014 |
| WO | 2015/057884 | 4/2015 |
| WO | 2015/083129 | 6/2015 |
| WO | 2017/049470 | 3/2017 |
| WO | 2017/050259 | 3/2017 |
| WO | 2018/015563 | 1/2018 |
| WO | 2018/098472 | 5/2018 |

OTHER PUBLICATIONS

International Search Report and Written Opinion for International Application No. PCT/US2020/066047, dated Mar. 23, 2021, 11 pages.
Partial International Search Report and Written Opinion for PCT Application No. PCT/US2021/037830, dated Oct. 6, 2021, 14 pages.
International Search Report and Written Opinion for PCT Application No. PCT/US2021/037830, dated Dec. 7, 2021,20 pages.
Partial International Search Report and Written Opinion for PCT Application No. PCT/US2021/037909, dated Oct. 4, 2021, 26 pages.
International Search Report and Written Opinion for PCT Application No. PCT/US2021/037909, dated Dec. 2, 2021, 27 pages.
International Search Report and Written Opinion for PCT Application No. PCT/US2021/042818, dated Nov. 12, 2021, 13 pages.
International Search Report and Written Opinion for PCT Application No. PCT/US2021/042818, dated Jan. 11, 2022, 18 pages.
International Search Report and Written Opinion for PCT Application No. PCT/US2021/053640, dated Mar. 3, 2022, 18 pages.
Non-Final Office Action for U.S. Appl. No. 16/831,086, dated Apr. 13, 2020, 8 pages.
Non-Final Office Action for U.S. Appl. No. 16/791,243, dated Apr. 8, 2020, 20 pages.
Ahn et al., "Hapten and Antibody Production for a Sensitive Immunoassay Determining a Human Urinary Metabolite of the Pyrethroid Insecticide Permethrin," Journal of Agricultural and Food Chemistry, Jun. 2004, vol. 52, No. 15, p. 4583-4594.
Search Report for Australia Application No. 2017406159, dated Feb. 28, 2020, 6 pages.
Search Report for Australia Application No. 2016328150, dated Mar. 27, 2020, 4 pages.
Search Report for Russia Application No. 2019134607, dated Feb. 11, 2020, 7 pages (translation).
Cameo Chemicals, ethyl-3-hydroxybutyrate, retrieved from https://web.archive.org/web/20170209085248/ https://cameochemicals.noaa.gov/chemical/20385, 2017, 5 pages.

Durig et al., "Pharmaceutical Technology Report: Water-Soluble Cellulose Ethers as Release Modulators for Ethylcellulose Coatings on Multiparticulates", Annual Meeting of the American Association of Pharmaceutical Scientists, Nov. 2011, 9 pages.
Jiang, et al., Copper-Catalyzed Aerobic Oxidative Regioselective Thiocyanation of Aromatics and Heteroaromatics. J. Org. Chem. 2017, 82, 18, 9312-9320.
Jimonet et al., "Riluzole series. Synthesis and in vivo "antiglutamate" activity of 6-substituted-2-benzothiazolamines and 3-substituted-2-imino-benzothiazolines", Journal of Medical Chemistry, 1999, vol. 42, p. 2828-2843.
Jordan, et al., Efficient Conversion of Substituted Aryl Thioureas to 2-Aminobenzothiazoles Using Benzyltrimethylammonium Tribromide. J. Org. Chem. 2003, 68, 22, 8693-8696.
Kaname et al., "One-pot copper-catalyzed tandem addition-cyclization of 2-iodoanilines with isoselenocyanates for the practical preparation of 2-aminobenzoselenazoles," Tetrahedron Letters, Jan. 2011, vol. 52, Issue 4, p. 505-508.
Lee et al., "Development of an Immunoassay for the Residues of the Herbicide Bensulfuron-Methyl," Journal of Agricultural and Food Chemistry, Mar. 2002, vol. 50, No. 7, p. 1791-1803.
Luengo et al., "Synthesis and Structure-Activity Relationships of Macrocyclic FKBP Ligands", Bioorganic & Medicinal Chemistry Letters, 1994, vol. 4, No. 2, p. 321-324.
McGeer et al., "Pharmacologic Approaches to the Treatment of Amyotrophic Lateral Sclerosis", Drug Mechanisms and Targets, 2006, vol. 19, No. 1, p. 31-37.
RN 1243631-58-4, STN entry date Sep. 29, 2010.
STN Columbus, Registry Jul. 21, 1990, 128321-03-09, 81055-72-3.
STN Columbus, Registry Dec. 4, 2015, CAS No. 1822708-15-5.
RN 142229-71-8, STN entry date Jul. 3, 1992.
RN 1211588-05-4, STN REG, Mar. 19, 2010.
RN 1354448-66-0, STN REG, Jan. 25, 2012.
RN 1206250-52-3, STN REG, Feb. 12, 2010.
RN 1206250-51-2, STN REG, Feb. 12, 2010.
RN 1206250-54-5, STN REG, Feb. 12, 2010.
RN 1206248-58-9, STN REG, Feb. 12, 2010.
RN 1744-22-5, STN entry date Nov. 16, 1984.
RN 326-45-4, STN entry date Nov. 16, 1984.
RN 747353-64-6, STN REG, Sep. 17, 2004.
RN 60176-62-7, STN entry date Nov. 16, 1984.
RN 60176-63-8, STN REG, Nov. 16, 1984.
RN 60388-38-7, STN entry date Nov. 16, 1984.
CAS Registry No. 238401-16-6 entry date Sep. 10, 1999.
Rothweiler, et al., Probing the ATP-Binding Pocket of Protein Kinase DYRK1A with Benzothiazole Fragment Molecules. J. Med. Chem. 2016, 59, 21, 9814-9824.
Rynearson et al., "2-Aminobenzoxazole ligands of the hepatitis C virus internal ribosome entry site," Bioorganic & Medicinal Chemistry Letters, Aug. 2014, vol. 24, No. 15, p. 3521-3525.
Sankaranarayanan et al., "Naphtho[1,2-d]thiazol-2-ylamine (SKA-31), a new activator of KCa2 and KCa3.1 potassium channels, potentiates the endothelium-derived hyperpolarizing factor response and lowers blood pressure", Molecular Pharmacology, 2009, vol. 75, p. 281-295.
Staldweiser et al., "Combinatorial Solid-Phase Synthesis of Structurally Complex Thiazolylhydantoines," Angewandte Chemie Int. Ed., A Journal of the German Chemical Society, Jun. 1998, vol. 37, No. 10, p. 1402-1404.
Ward et al., "Discovery of an Orally Bioavailable Nki Receptor Antagonist, (2S, 3S)-(2-Methoxy-5-tetrazol-1-ylbenzyl)(2-phenylpiperidin-3-yl)amine (GR203040), with Potent Antiemetic Activity," Journal of Med. Chem., 1995, vol. 38, p. 4985-4992.
International Search Report and Written Opinion for PCT Application No. PCT/US2022/020926, dated Jun. 20, 2022, 16 pages.
Abdul et al., "A flexible technology for modified-release drugs: Multiple-unit pellet system (MUPS)", Journal of Controlled Release, Oct. 2010, vol. 147, No. 1, pp. 2-16.

| Formulation | | Predose | 0.5 | 1 | 1.5 | 2 | 2.5 | 3 | 3.5 | 4 | 4.5 | 5 | 5.5 | 6 | 6.5 | 7 | 8 | 10 | 12 |
|---|---|---|---|---|---|---|---|---|---|---|---|---|---|---|---|---|---|---|---|
| CR1 | Mean | 0.00 | 18.19 | 11.34 | 7.81 | 5.72 | 4.22 | 3.41 | 3.41 | 2.23 | 1.90 | 1.04 | 0.65 | 0.56 | 0.70 | 0.42 | 0.23 | 0.02 | 0.01 |
| | SD | 0.00 | 7.78 | 3.94 | 3.70 | 2.70 | 2.26 | 1.63 | 2.80 | 2.08 | 1.30 | 0.83 | 0.58 | 0.63 | 1.24 | 0.85 | 0.61 | 0.06 | 0.05 |
| CR2 | Mean | 0.00 | 16.61 | 7.42 | 5.34 | 5.37 | 4.06 | 3.39 | 2.58 | 3.34 | 1.83 | 0.96 | 0.64 | 0.48 | 0.30 | 0.14 | 0.05 | 0.00 | 0.00 |
| | SD | 0.00 | 5.82 | 1.89 | 1.69 | 2.15 | 1.62 | 2.21 | 1.72 | 4.54 | 0.69 | 0.46 | 0.49 | 0.26 | 0.18 | 0.12 | 0.08 | 0.00 | 0.00 |
| CR3 | Mean | 0.00 | 15.25 | 8.74 | 10.97 | 7.92 | 5.05 | 3.44 | 3.90 | 3.20 | 3.55 | 1.77 | 2.28 | 1.01 | 0.83 | 0.60 | 0.33 | 0.17 | 0.04 |
| | SD | 0.00 | 6.56 | 3.66 | 5.66 | 5.71 | 2.41 | 2.21 | 6.75 | 3.27 | 4.65 | 1.60 | 2.79 | 1.21 | 1.02 | 0.79 | 0.46 | 0.28 | 0.09 |
| CR4 | Mean | 0.00 | 14.03 | 10.36 | 6.34 | 4.57 | 5.85 | 4.78 | 3.39 | 4.66 | 3.14 | 2.38 | 1.35 | 1.57 | 1.46 | 0.87 | 0.42 | 0.12 | 0.01 |
| | SD | 0.00 | 6.02 | 5.35 | 3.34 | 1.59 | 4.98 | 3.72 | 2.88 | 4.76 | 2.87 | 2.10 | 0.75 | 1.56 | 1.80 | 1.03 | 0.50 | 0.18 | 0.03 |

FIG. 3

| Formulation | | Predose | 0.5 | 1 | 1.5 | 2 | 2.5 | 3 | 3.5 | 4 | 4.5 | 5 | 5.5 | 6 | 6.5 | 7 | 8 | 10 | 12 |
|---|---|---|---|---|---|---|---|---|---|---|---|---|---|---|---|---|---|---|---|
| CR1 | Mean | 0.00 | 58.70 | 86.02 | 93.60 | 91.66 | 86.25 | 75.00 | 70.95 | 60.96 | 51.88 | 40.32 | 30.53 | 23.86 | 15.65 | 10.58 | 3.61 | 0.47 | 0.05 |
| | SD | 0.00 | 29.12 | 18.33 | 22.19 | 23.15 | 22.61 | 24.60 | 25.08 | 27.66 | 26.07 | 24.03 | 21.53 | 19.22 | 14.46 | 10.74 | 3.57 | 0.59 | 0.15 |
| CR2 | Mean | 0.00 | 54.48 | 71.37 | 68.52 | 67.59 | 65.33 | 59.81 | 54.05 | 51.43 | 44.68 | 36.25 | 28.43 | 24.66 | 18.81 | 14.03 | 6.11 | 1.08 | 0.39 |
| | SD | 0.00 | 19.62 | 17.27 | 16.10 | 15.28 | 18.93 | 21.57 | 24.36 | 29.63 | 28.09 | 27.10 | 25.16 | 21.24 | 17.29 | 13.53 | 6.54 | 1.46 | 0.46 |
| CR3 | Mean | 0.00 | 48.51 | 61.65 | 82.68 | 81.98 | 76.06 | 70.20 | 62.02 | 57.96 | 51.35 | 43.51 | 39.09 | 29.90 | 22.47 | 17.22 | 9.53 | 3.71 | 0.80 |
| | SD | 0.00 | 25.51 | 25.76 | 25.53 | 24.78 | 26.80 | 29.70 | 28.80 | 34.27 | 29.39 | 28.27 | 30.68 | 27.24 | 23.90 | 21.82 | 15.28 | 6.65 | 1.61 |
| CR4 | Mean | 0.00 | 40.50 | 71.03 | 70.21 | 65.30 | 68.54 | 67.64 | 62.60 | 60.22 | 57.94 | 49.45 | 41.81 | 33.03 | 28.60 | 23.57 | 14.01 | 5.01 | 0.97 |
| | SD | 0.00 | 21.17 | 25.11 | 25.21 | 18.89 | 25.32 | 26.74 | 31.73 | 29.28 | 31.38 | 29.91 | 28.88 | 24.87 | 27.51 | 23.90 | 18.33 | 8.13 | 2.16 |

FIG. 4

PHARMACOKINETICS OF COMBINED RELEASE FORMULATIONS OF A γ-HYDROXYBUTYRIC ACID DERIVATIVE

This application claims the benefit under 35 U.S.C. § 119(e) of U.S. Provisional Application No. 63/163,096 filed on Mar. 19, 2021, which is incorporated by reference in its entirety.

This application is related to U.S. Application Publication No. 2022/0023247, and U.S. Application Publication No. 2021/0393537 A1, and U.S. Application Publication No. 2021/0393529 A1.

FIELD

The disclosure relates to pharmaceutical compositions comprising 4-((L-valyl)oxy)butanoic acid and the pharmacokinetics of 4-((L-valyl)oxy)butanoic acid and γ-hydroxybutyrate following oral administration of the pharmaceutical compositions.

BACKGROUND

Sodium γ-hydroxybutyrate is approved by the United States Food and Drug Administration for the treatment of sudden muscle weakness and excessive daytime sleepiness associated with narcolepsy. Sodium γ-hydroxybutyrate is the sodium salt of γ-hydroxybutyric acid.

SUMMARY

According to the present invention, pharmaceutical compositions comprise an immediate release (IR) component, wherein the immediate release component comprises from 1.5 g γ-hydroxybutyrate-equivalents to 3.5 g γ-hydroxybutyrate-equivalents; and a modified release (MR) component, wherein the modified release component comprises from 3 g γ-hydroxybutyrate to 9 g γ-hydroxybutyrate-equivalents.

According to the present invention, methods of treating fatigue or excessive daytime sleepiness associated with narcolepsy in a patient comprise orally administering to a patient in need of such treatment a therapeutically effective amount of the pharmaceutical composition according to the present invention.

According to the present invention, methods of treating narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia in a patient comprise orally administering to a patient in need of such treatment a therapeutically effective amount of the pharmaceutical composition according to the present invention.

According to the present invention, methods of treating a symptom associated with narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia in a patient comprise orally administering to a patient in need of such treatment a therapeutically effective amount of the pharmaceutical composition according to the present invention.

According to the present invention, methods of treating rapid eye movement (REM) sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety in a patient comprise orally administering to a patient in need of such treatment a therapeutically effective amount of the pharmaceutical composition according to the present invention.

According to the present invention, methods of treating a symptom associated with REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety in a patient comprise orally administering to a patient in need of such treatment a therapeutically effective amount of the pharmaceutical composition according to the present invention.

According to the present invention, methods of treating a sleep disorder associated with a bacterial infection in a patient comprise orally administering to a patient in need of such treatment, a therapeutically effective amount of the pharmaceutical composition according to the present invention.

According to the present invention, methods of enhancing cognitive function in a patent having a neurological disorder comprise orally administering to a patient in need of such treatment, a therapeutically effective amount of the pharmaceutical composition according to the present invention.

According to the present invention, kits comprise the pharmaceutical composition according to the present invention.

BRIEF DESCRIPTION OF THE DRAWINGS

Those skilled in the art will understand that the drawings described herein are for illustration purposes only. The drawings are not intended to limit the scope of the present disclosure.

FIG. 3 is a table showing the mean plasma concentration of compound (1) following oral administration of combined release formulations to fasted, healthy subjects.

FIG. 4 is a table showing the mean plasma γ-hydroxybutyrate concentration following oral administration of combined release formulations to fasted, healthy subjects.

DETAILED DESCRIPTION

Figure 1:
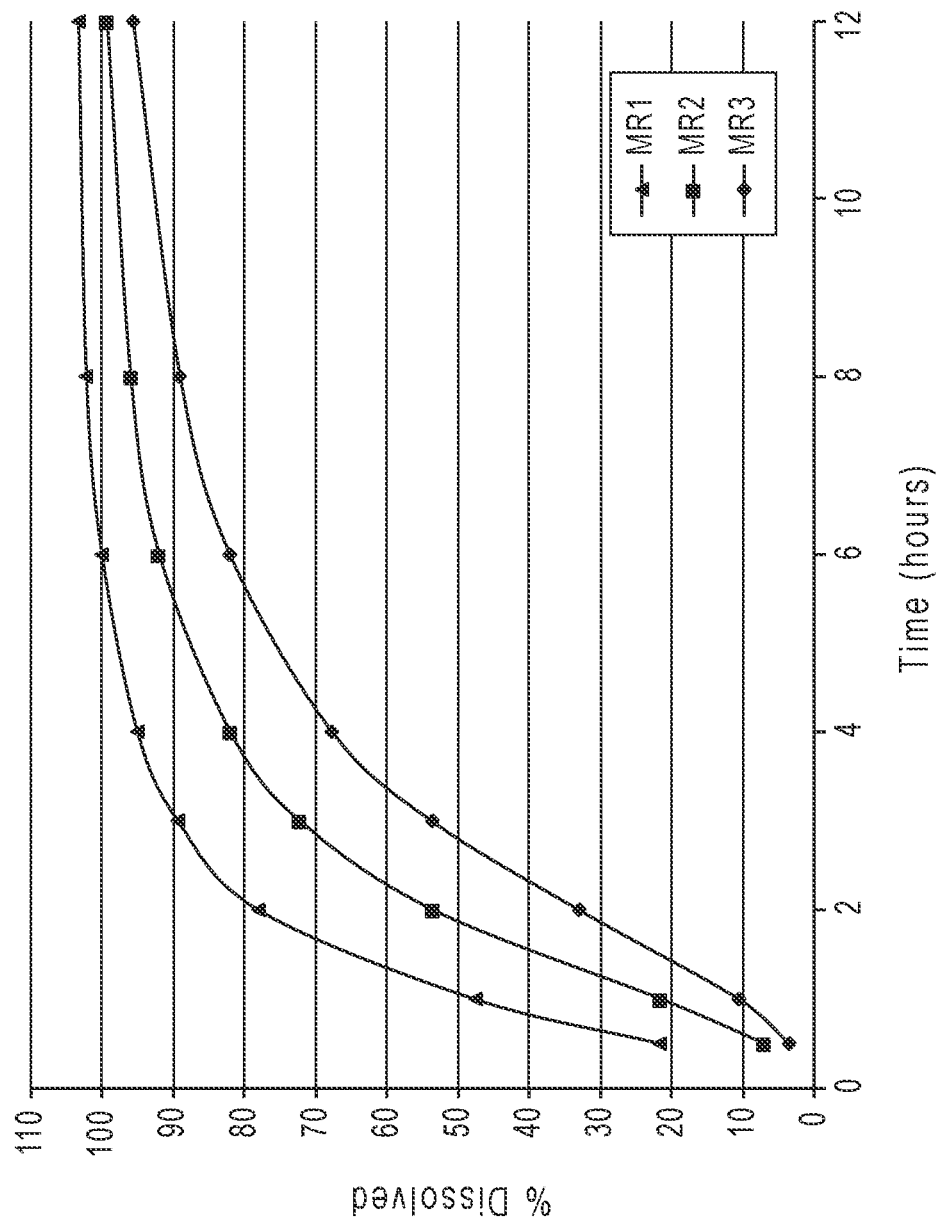
FIG. 1 shows dissolution profiles for modified release microparticles provided by the present disclosure.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Immediate release" refers to a composition that releases at least 80% of compound (1) within 1 hour when tested in a dissolution apparatus 2 according to United States Pharmacopeia (USP) 38 in a 0.1 N HCl dissolution medium at a temperature of 37° C. and a paddle speed of 75 rpm.

An immediate release composition or formulation can release substantially all of a pharmaceutically active ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the pharmaceutically active ingredient such as compound (1) in the pharmaceutical composition into the gastrointestinal tract within less than 1 hour, such as within less than 50 minutes, less than 40 minutes, less than 30 minutes, less than 20 minutes, or less than 10 minutes, following oral administration. Immediate release pharmaceutical compositions can be appropriate to administer pharmaceutically active ingredients that are absorbed into the systemic circulation from the upper portion of the gastrointestinal tract.

"Modified release" pharmaceutical compositions and formulations can include controlled release formulations, delayed release formulations, extended-release formulations, sustained release formulations, timed release formulations, pulsatile release formulations, and pH-dependent release formulations. These formulations are intended to release a pharmaceutically active ingredient from the pharmaceutical composition at a desired rate and/or at a desired time following oral administration by a patient and/or at a certain location or locations within the gastrointestinal tract and/or at a certain pH within the gastrointestinal tract. The United States Pharmacopeia (USP) defines a modified release system as one in which the time course or location of drug release or both, are chosen to accomplish objectives of therapeutic effectiveness or convenience not fulfilled by immediate release dosage forms. A modified release oral dosage form can include extended release and delayed-release components. A delayed release dosage form is one that releases a drug all at once at a time other than promptly after administration. A modified release formulation can include delayed-release using enteric coatings, site-specific or timed release such as for colonic delivery, extended-release including, for example, formulations capable of providing zero-order, first-order, or biphasic release profiles, and programmed release such as pulsatile and delayed extended release.

"Sustained release" pharmaceutical compositions and coating provide for a dissolution rate over an extended period of time following oral administration. Granulations comprising microparticles having a sustained release coating can be referred to as sustained release granulations. A pharmaceutical composition comprising a sustained release granulation can be referred to as a sustained release pharmaceutical composition.

"Bioequivalent" refers to a formulation and/or pharmaceutical composition that is therapeutically equivalent to a reference product when administered under the same conditions in a pharmacokinetic evaluation conforming to United States Food and Drug Administration (USFDA) Guidance on Bioequivalence Testing; regardless of biopharmaceutical class.

A value that is "bioequivalent" refers to a pharmacokinetic value such as the peak blood or plasma concentration ($C_{max}$) or area under the curve (AUC) that exhibits substantially similar pharmacokinetic profiles and/or therapeutic effects. Bioequivalence may be demonstrated by several in vivo and in vitro methods. These methods may include, for example, pharmacokinetic, pharmacodynamic, clinical and in vitro studies. Bioequivalence can be demonstrated using any suitable pharmacokinetic measures or combination of pharmacokinetic measures known in the art, including loading dose, steady-state dose, initial or steady-state concentration of drug, biological half-life, elimination rate, AUC, clearance, the $C_{max}$, time to peak concentration ($T_{max}$), bioavailability and potency. In some embodiments, a value is bioequivalent to a reference pharmacokinetic value when the geometric mean of the AUC and/or the $C_{max}$ is between 80% and 125% (e.g., at 90% confidence interval) of the reference pharmacokinetic value.

A similar or bioequivalent pharmacokinetic profile refers to a pharmacokinetic profile for which the mean $AUC_{0-inf}$ of a pharmaceutical composition is from 80% to 125% of the mean $AUC_{0-inf}$ a reference composition in a suitably designed cross-over trial, the mean plasma concentration at 8 hours $C_{8h}$ of the pharmaceutical composition is from 40% to 130% of the mean plasma concentration at 8 hours $C_{8h}$ of the reference composition, and/or that the maximum plasma concentration ($C_{max}$) of the pharmaceutical composition is from 50% to 140% of the $C_{max}$ of the reference composition.

A "fed state" refers to the period of time immediately after consumption of a meal up to two hours post consumption. The fed state can include the period less than two hours after eating.

A "fasted state" refers to the period of time after 8 hours post meal consumption.

"Patient" refers to a mammal, for example, a human.

"Pharmaceutically acceptable" refers to approved or approvable by a regulatory agency of the Federal or a state government or listed in the U.S. Pharmacopoeia (USP) or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable modified release groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof, or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Prodrug" refers to a derivative of a drug molecule that requires a transformation within the body to provide the active drug. Prodrugs are frequently, although not necessarily, pharmacologically inactive until converted to the parent drug. Prodrugs may be obtained by bonding a promoiety (defined herein) typically via a modified release group, to a drug.

"Curing" a disease refers to eliminating the disease or disorder or eliminating a symptom of the disease or disorder.

"Treating" or "treatment" of a disease or disorder refers to reducing the severity of one or more clinical symptom of the disease or disorder, delaying the onset of one or more clinical symptoms of the disease or disorder, and/or mitigating one or more clinical symptoms of the disease or disorder. "Treating" or "treatment" of a disease or disorder refers to inhibiting the disease or disorder or one or more clinical symptoms of the disease or disorder, arresting the development of the disease or disorder or one or more clinical symptoms of the disease or disorder, relieving the disease or disorder or one or more clinical symptoms of the disease or disorder, causing the regression of the disease or disorder or one or more clinical symptoms of the disease or disorder, and/or stabilization of the disease or disorder or one or more clinical symptoms of the disease or disorder, "Treating" or "treatment" of a disease or disorder refers to producing a clinically beneficial effect without curing the underlying disease or disorder.

"Therapeutically effective amount" refers to the amount of a pharmaceutically active ingredient such as compound (1) or γ-hydroxybutyrate, when administered to a patient for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. A therapeutically effective amount in any given instance may be ascertained by those skilled in the art or capable of determination by routine experimentation or based on the judgment of a prescribing physician or medical professional.

"Therapeutically effective dose" refers to a dose that provides effective treatment of a disease or disorder in a patient. A therapeutically effective dose of compound (1) or γ-hydroxybutyrate may vary from patient to patient and may depend upon factors such as the medical condition of the patient, the severity of the disease and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

"Percent weight gain" or "% wg" such as in a "35% wg" coating refers to a coated microparticle in which the weight of the coated microparticle is 35% greater than the weight of the uncoated microparticle.

Dissolution profiles are measured using a USP Type 2 dissolution apparatus a sodium acetate buffered solution at pH 4.5 at a temperature of 37° C. and a paddle speed of 75 rpm.

"$C_{max}$" refers to the maximum plasma concentration.

"$C_t$" refers to the plasma concentration at time t, where time t is the duration following administration. For example, $C_6$ refers to the plasma concentration of an analyte six (6) hours after administration.

"$T_{max}$" refers to the time to reach the maximum plasma concentration.

"$AUC_{0-tlast}$" refers to the area under the plasma concentration-time curve from time 0 to the time of the last quantifiable concentration.

"$AUC_{0-inf}$" refers to the area under the plasma concentration-time curve from time 0 to infinite time, calculated as the sum of $AUC_{0-tlast}$ and $C_{last}/\lambda z$.

"$AUC_{0-\tau}$" refers to the area under the plasma concentration-time curve during a dosing interval τ. For example, the interval can be 6 hours or 8 hours after dosing.

"λz" refers to the apparent terminal elimination rate constant.

"$T_{1/2}$" refers to the elimination half-life associated with the terminal slope ($\lambda z$) of the semilogarithmic drug concentration-time curve, calculated as $0.693/\lambda z$.

"CL/F" refers to the apparent total body clearance of a drug from the plasma calculated by: $CL/F=Dose/AUC_{0-inf}$.

Reference is now made to microparticles comprising 4-((L-valyl)oxy)butanoic acid, to pharmaceutical compositions comprising 4-((L-valyl)oxy)butanoic acid and, to the pharmacokinetics of 4-((L-valyl)oxy)butanoic acid and γ-hydroxybutyrate following oral administration of the pharmaceutical compositions comprising 4-((L-valyl)oxy)butanoic acid to fasted, healthy subjects. The disclosed microparticles, pharmaceutical compositions and pharmacokinetics are not intended to be limiting of the claims. To the contrary, the claims are intended to cover all alternatives, modifications, and equivalents.

Sodium oxybate (sodium γ-hydroxybutyrate) is approved by the United States Food and Drug Administration for the treatment of muscle fatigue and excessive daytime sleepiness associated with narcolepsy. Sodium oxybate is available under the tradename XYREM® from Jazz Pharmaceuticals. Sodium oxybate is orally administered and is a salt form of the pharmaceutically active ingredient γ-hydroxybutyric acid, also known as γ-hydroxybutyrate and oxybate. Sodium oxybate and γ-hydroxybutyric acid have the structure of Formula (2a) and Formula (2b), respectively.

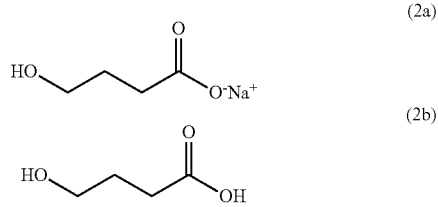

4-((L-Valyl)oxy)butanoic acid (Compound (1)) is a prodrug of γ-hydroxybutyric acid (GHB; γ-hydroxybutyrate), which following oral administration, is metabolized to provide γ-hydroxybutyrate in the plasma of a patient. 4-((L-valyl)oxy)butanoic acid has the structure of Formula (1):

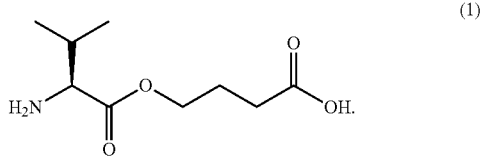

One gram of Compound (1) comprises 0.512 g γ-hydroxybutyrate equivalents. For example, 4.5 g of compound (1) comprises 2.3 g γ-hydroxybutyrate equivalents, and 10 g of compound (1) comprises 5.2 g γ-hydroxybutyrate equivalents.

Compound (1) is equivalent to 0.62 g of sodium γ-hydroxybutyrate. For example, 4.5 g of compound (1) is equivalent to 2.79 g sodium γ-hydroxybutyrate, and 4.5 g sodium γ-hydroxybutyrate is equivalent to 7.26 g of compound (1).

Pharmaceutical compositions provided by the present disclosure can comprise an immediate release component, a modified release component, and a combination thereof.

An immediate release (IR) component can comprise microparticles comprising compound (1) configured to immediately dissolve upon contact with gastrointestinal fluid or in an oral pharmaceutical composition.

A modified release (MR) component can comprise microparticles comprising compound (1) configured to dissolve in gastrointestinal fluid overtime.

A combined release (CR) pharmaceutical composition provided by the present disclosure can comprise an immediate release component and a modified release component. A pharmaceutical composition provided by the present disclosure can comprise, for example, from 3 g to 6 g of compound (1) in the IR component and from 6 g to 16 g of compound (1) in a MR component, from 3 g to 6 g in an IR component and from 7 g to 13 g in an MR component, from 3 g to 6 g in an IR component and from 8 g to 12 g in an MR components, from 3 g to 6 g in an IR component and from 9 g to 11 g in an MR component, or from 3.5 g to 5.5 g of compound (1) in an IR component and from 9 g to 11 g of compound (1) in an MR component.

A pharmaceutical composition provided by the present disclosure can comprise, for example, a weight ratio of compound (1) in the IR component to compound (1) in the MR component from 1:1.5 to 1:3.5, from 1:1.7 to 1:3.3, from 1:1.9 to 1:3.1, from 1:2.1 to 1:2.9, from 1:2.3 to 1:2.7, or from 1:2.4 to 1.2.7.

A pharmaceutical composition provided by the present disclosure can comprise, for example, from 20 wt % to 40 wt % compound (1) in the IR component, from 22 wt % to 38 wt %, from 24 wt % to 36 wt %, from 26 wt % to 36 wt %, or from 28 wt % to 34 wt % compound (1) in the IR component, where wt % is based on the total weight of compound (1) in the pharmaceutical composition.

A pharmaceutical composition provided by the present disclosure can comprise, for example, from 60 wt % to 80 wt % compound (1) in the MR component, from 62 wt % to 78 wt %, or from 65 wt % to 75 wt %, of compound (1) in the MR component, where wt % is based on the total weight of compound (1) in the pharmaceutical composition.

A pharmaceutical composition provided by the present disclosure can comprise a molar ratio of compound (1) in the immediate release component to compound (1) in the modified release component, for example, from 1:1 to 1:10, from 1:1 to 1:9, from 1:1.5 to 1:8.5, from 1:2 to 1:8, from 1:2.5 to 1:7.5, from 1:3 to 1:1.7, from 1:3.5 to 1:6.5 or from 1:4 to 1:6.

A pharmaceutical composition provided by the present disclosure can comprise a molar percentage of compound (1) in the immediate component, for example, from 5% to 40%, from 10% to 35%, from 15% to 30% or from 20% to 25% based on the total moles of compound (1) in the pharmaceutical composition.

A pharmaceutical composition provided by the present disclosure can comprise a molar percentage of compound (1) in the modified release component, for example, from 95% to 69%, from 90% to 65%, from 85% to 60%, from 80% to 55%, or from 75% to 60% based on the total moles of compound (1) in the pharmaceutical composition.

A pharmaceutical composition provided by the present disclosure can comprise, for example, from 1.5 g to 3 g γ-hydroxybutyrate equivalents in the IR component and from 3 g to 8 g γ-hydroxybutyrate equivalents in a MR component, from 1.5 g to 3 g in an IR component and from 3.5 g to 6.5 g in an MR component, from 1.5 g to 3 g in an IR component and from 4 g to 6 g in an MR components, from 1.5 g to 3 g in an IR component and from 4.5 g to 15.5 g in an MR component, or from 1.7 g to 52.8 g of compound (1) in an IR component and from 4.5 g to 5.5 g γ-hydroxybutyrate equivalents in an MR component.

A pharmaceutical composition provided by the present disclosure can comprise, for example, a weight ratio γ-hydroxybutyrate equivalents in the IR component to γ-hydroxybutyrate equivalents in the MR component from 1:1.5 to 1:3.5, from 1:1.7 to 1:3.3, from 1:1.9 to 1:3.1, from 1:2.1 to 1:2.9, from 1:2.3 to 1:2.7, or from 1:2.4 to 1.2.7.

A pharmaceutical composition provided by the present disclosure can comprise, for example, from 20 wt % to 40 wt % γ-hydroxybutyrate equivalents in the IR component, from 22 wt % to 38 wt %, from 24 wt % to 36 wt %, from 26 wt % to 36 wt %, or from 28 wt % to 34 wt % γ-hydroxybutyrate equivalents in the IR component, where wt % is based on the total weight of γ-hydroxybutyrate equivalents in the pharmaceutical composition.

A pharmaceutical composition provided by the present disclosure can comprise, for example, from 60 wt % to 80 wt % γ-hydroxybutyrate equivalents in the MR component, from 62 wt % to 78 wt %, or from 65 wt % to 75 wt %, γ-hydroxybutyrate equivalents in the MR component, where wt % is based on the total weight of γ-hydroxybutyrate equivalents in the pharmaceutical composition.

A pharmaceutical composition provided by the present disclosure can comprise a molar ratio of γ-hydroxybutyrate equivalents in the immediate release component to γ-hydroxybutyrate equivalents in the modified release component, for example, from 1:1 to 1:10, from 1:1 to 1:9, from 1:1.5 to 1:8.5, from 1:2 to 1:8, from 1:2.5 to 1:7.5, from 1:3 to 1:1.7, from 1:3.5 to 1:6.5 or from 1:4 to 1:6.

A pharmaceutical composition can com provided by the present disclosure can comprise a molar percentage of γ-hydroxybutyrate equivalents in the immediate component, for example, from 5% to 40%, from 10% to 35%, from 15% to 30% or from 20% to 25% based on the total γ-hydroxybutyrate equivalents in the pharmaceutical composition.

A pharmaceutical composition provided by the present disclosure can comprise a molar percentage of γ-hydroxybutyrate equivalents in the modified release component, for example, from 95% to 69%, from 90% to 65%, from 85% to 60%, from 80% to 55%, or from 75% to 60% based on the total moles of γ-hydroxybutyrate equivalents in the pharmaceutical composition.

A pharmaceutical composition provided by the present disclosure can comprise, for example, from 2 g to 6 g sodium γ-hydroxybutyrate equivalents in the IR component and from 6 g to 16 g of sodium γ-hydroxybutyrate equivalents in a MR component, from 2 g to 6 g in an IR component and from 7 g to 15 g in an MR component, from 3 g to 6 g in an IR component and from 8 g to 14 g in an MR components, from 2 g to 6 g in an IR component and from 9 g to 14 g in an MR component, or from 1.2 g to 3.8 g of sodium γ-hydroxybutyrate equivalents in an IR component and from 3.8 g to 9.0 g of sodium γ-hydroxybutyrate equivalents in an MR component.

An immediate release component provided by the present disclosure can comprise immediate release microparticles. An immediate release microparticle can comprise an uncoated microparticle or a microparticle comprising an immediate release coating.

A modified release component provided by the present disclosure can comprise a modified release microparticle. A modified release microparticle can comprise an uncoated microparticle comprising a modified release coating. A modified release microparticle can comprise an microparticle comprising an immediate release coating and an overlying modified release coating.

An uncoated immediate release microparticle provided by the present disclosure can comprise a pharmaceutically active ingredient, a binder, and an antistatic agent.

An uncoated immediate release microparticle can comprise, for example, greater than 90 wt % of compound (1), greater than 92 wt %, greater than 94 wt %, greater than 96 wt %, or greater than 98 wt % compound (1), where wt % is based on the total weight of the uncoated immediate release microparticle. An uncoated immediate release microparticle provided by the present disclosure can comprise, for example, from 90 wt % to 99.9 wt % of compound (1), from 91 wt % to 99.5 wt %, from 92 wt % to 99 wt %, from 93 wt % to 98.5 wt %, from 94 wt % to 98 wt %, or from 94.5 wt % to 97.5 wt % compound (1), where wt % is based on the total weight of the immediate release microparticle.

An uncoated immediate release microparticle can comprise a binder or a combination of binders.

An uncoated immediate release microparticle can comprise, for example, less than 1 wt % of a binder, less than 0.8 wt %, less than 0.6 wt %, less than 0.4 wt %, or less than 0.2 wt % of a binder, where wt % is based on the total weight of the uncoated immediate release microparticle. An uncoated immediate release microparticle can comprise, for example, from 0.1 wt % to 1.0 wt % of a binder, from 0.2 wt % to 0.9 wt %, from 0.2 wt % to 0.8 wt %, from 0.25 wt % to 0.75 wt %, or from 0.3 wt % to 0.7 wt % of a binder, where wt % is based on the total weight of the uncoated immediate release microparticle.

An uncoated microparticle can comprise, for example, less than 3 wt % of a binder, less than 2.5 wt %, less than 2 wt %, less than 1.5 wt %, or less than 1 wt % of a binder, where wt % is based on the total weight of the uncoated immediate release microparticle.

An uncoated immediate release microparticle can comprise any suitable binder. Examples of suitable binders include natural binders such as starch, pregelatinized starch, sodium alginate, and gelatin; synthetic binders such as polyvinyl pyrrolidone, methylcellulose, hydroxypropylmethyl cellulose, polymethacrylates, sodium carboxy methyl cellulose, and polyethylene glycol; and saccharides such as modified cellulose, hydroxypropyl cellulose, sorbitol, xylitol, and mannitol.

Examples of other suitable binders include, acacia, copovidone, carbomer, corn starch, pregelatinized starch, calcium carboxymethyl cellulose, calcium cellulose glycolate, carmellosum calcium, carboxymethyl cellulose sodium, carmellose sodium, ceratonia, chitosan hydrochloride, dextrates, dextrin, ethyl cellulose, liquid glucose, guar galactomannan, guar gum, hydroxyethyl cellulose, microcrystalline cellulose, hydroxyethylmethyl cellulose, hydroxypropyl cellulose, low-substituted hydroxypropyl cellulose, hydroxypropyl starch, hypromellose/hydroxypropyl methyl cellulose, inulin, magnesium aluminum silicate, maltodextrin, methylcellulose, polyethylene glycol, polyethylene oxide, povidone, sodium alginate, starch, pregelatinized starch, sucrose, compressible sugar, zein, gelatin, polymethacrylates, sorbitol, glucose, and sodium alginate.

An uncoated immediate release microparticle can comprise an antistatic agent or a combination of antistatic agents.

An uncoated immediate release microparticle can comprise, for example, less than 3 wt %, less than 2.5 wt %, less than 2 wt % of an antistatic agent, less than 1.25 wt %, less than 1 wt %, less than 0.75 wt %, less than 0.5 wt %, or less than 0.25 wt % of an antistatic agent, where wt % is based on the total weight of the uncoated immediate release microparticle. An uncoated immediate release microparticle can comprise, for example, from 0.1 wt % to 3.0 wt % of an antistatic agent, from 0.2 wt % to 2 wt %, from 0.5 wt % to 1.50 wt %, or from 0.75 wt % to 1.25 wt % of an antistatic agent, where wt % is based on the total weight of the uncoated immediate release microparticle.

An uncoated immediate release microparticle can comprise any suitable antistatic agent.

Examples of suitable antistatic agents include hydrophilic silica, talc, magnesium stearate, sodium stearyl fumarate, and combinations of any of the foregoing.

An antistatic agent can comprise, for example, hydrophilic fumed silica such as AEROSIL® 200 (Evonik Industries).

An uncoated immediate release microparticle can comprise, for example, from 95.0 wt % to 99.5 wt % of compound (1); from 0.1 wt % to 1.0 wt % of a binder; and from 0.1 wt % to 2.0 wt % of an antistatic agent, wherein wt % is based on the total weight of the uncoated immediate release microparticle.

An uncoated immediate release microparticle can comprise, for example, from 98 wt % to 99 wt % of compound (1); from 0.25 wt % to 0.75 wt % of a binder; and from 0.5 wt % to 1.5 wt % of an antistatic agent, wherein wt % is based on the total weight of the uncoated immediate release microparticle.

An uncoated immediate release microparticle can comprise, for example, from 98.25 wt % to 98.75 wt % of compound (1); from 0.33 wt % to 0.65 wt % of a binder; and from 0.74 wt % to 1.25 wt % of an antistatic agent, wherein wt % is based on the total weight of the uncoated immediate release microparticle.

In addition to a pharmaceutically active ingredient, a binder, and an antistatic agent, an uncoated immediate release microparticle can comprise one or more excipients such as, for example, flow control agents, lubricants, disintegrants, fillers, compression aids, surfactants, diluents, colorants, buffering agents, glidants, and combinations of any of the foregoing.

An uncoated immediate release microparticle can comprise, for example, less than 3 wt % of the one or more excipients, less than 2 wt %, less than 1 wt %, or less than 0.5 wt % of the one or more excipients, where wt % is based on the total weight of the uncoated immediate release microparticle. An uncoated immediate release microparticle can comprise, for example, from 0 wt % to 3 wt % of one or more excipients, from 0.1 wt % to 3 wt %, from 0.5 wt % to 2 wt %, or from 1 wt % to 2 wt % of one or more excipients, where wt % is based on the total weight of the uncoated immediate release microparticle.

Examples of suitable flow control agents or glidants include magnesium stearate, fumed silica (colloidal silicon dioxide), starch, and talc.

Examples of suitable lubricants include magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, zinc stearate, and combinations of any of the foregoing.

Examples of suitable disintegrants include citric acid, croscarmellose sodium, colloidal silicon dioxide, crospovidone, sodium starch glycolate, microcrystalline cellulose, pregelatinized starch, and combinations of any of the foregoing.

A surfactant can comprise an ionic surfactant or a non-ionic surfactant. Examples of suitable anionic surfactants include docusate sodium (dioctyl sulfosuccinate sodium salt), sodium lauryl sulfate, and combinations of any of the foregoing. Examples of suitable non-ionic surfactants include polyoxyethylene alkyl ethers, polyoxyethylene stearates, poloxamers, polysorbate, sorbitan esters, glyceryl monooleate, and combinations of any of the foregoing.

Examples of suitable fillers and compression aids include lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, sucrose, and combinations of any of the foregoing.

An uncoated immediate release microparticle provided by the present disclosure can be characterized by a sphericity, for example, from 0.90 to 1, such as from 0.91 to 0.99, or from 0.92 to 0.98, where sphericity of an uncoated immediate release microparticle provided by the present disclosure can be characterized by a sphericity, for example, greater than 0.90, greater than 0.91, greater than 0.92, greater than 0.93, greater than 0.94, or greater than 0.95.

An uncoated immediate release microparticle provided by the present disclosure can be comprise a plurality of microparticles characterized by a mode sphericity, for example, from 0.90 to 1, such as from 0.91 to 0.99, or from 0.92 to 0.98, where sphericity is determined using wet dispersion particle shape methods or by dynamic image analysis. An uncoated immediate release microparticle provided by the present disclosure can comprise a plurality of microparticles characterized by an average sphericity, for example, greater than 0.94, greater than 0.95, greater than 0.96, greater than 0.97, greater than 0.98, or greater than 0.99.

Uncoated immediate release microparticles provided by the present disclosure are solid and are characterized by a substantially homogeneous composition throughout the uncoated immediate release microparticle. A homogeneous composition refers to a composition that does not have an internal structure such a layers or core/shells and where the composition is the same with in less than ±5 wt %, less than ±2 wt %, or less than ±1 wt % throughout the microparticle.

For high dose pharmaceutically active ingredients, especially when reconstituted as a suspension before administration, to improve palatability it can be useful that the microparticles have a small mean diameter.

A plurality of uncoated immediate release microparticles provided by the present disclosure can be characterized, for example, by a particle size distribution (PSD) (D50) from 75 µm to 450 µm, from 100 µm to 400 µm, from 150 µm to 350 µm, from 175 µm to 325 µm, from 200 µm to 300 µm, or from 225 µm to 275 µm.

A plurality of uncoated immediate release microparticles can be characterized, for example, by a PSD (D10) from 50 µm to 150 µm, from 60 µm to 140 µm, from 70 µm, to 120 µm, or from 80 µm to 110 µm.

A plurality of uncoated immediate release microparticles can be characterized, for example, by a PSD (D90) from 450 µm to 750 µm, from 475 µm to 725 µm, from 500 µm to 700 µm, from 525 µm to 675 µm, or from 550 µm to 650 µm.

A plurality of uncoated immediate release microparticles can be characterized, for example, by a PSD (D10) from 50 µm to 150 µm; a PSD (D50) from 220 µm to 320 µm; and a PSD (D90) from 480 µm to 560 µm.

A plurality of uncoated immediate release microparticles can be characterized, for example, by a PSD (D10) from 60 µm to 140 µm; a PSD (D50) from 230 µm to 310 µm; and a PSD (D90) from 490 µm to 550 µm.

A plurality of uncoated immediate release microparticles can be characterized, for example, by a PSD (D10) from 70

μm to 130 μm; a PSD (D50) from 240 μm to 300 μm; and a PSD (D90) from 500 μm to 540 μm.

A particle size distribution can be determined by laser diffraction or by sieve analysis.

A plurality of uncoated immediate release microparticles can have a bulk density, for example, greater than 0.60 g/mL, greater than 0.90 g/mL, greater than 1.10 g/mL, greater than 1.30 g/mL, or greater than 1.50 g/mL.

A plurality of uncoated immediate release microparticles can have a bulk density, for example, from 0.60 g/mL to 1.60 g/mL, from 0.70 g/mL to 1.50 g/mL, from 0.80 g/mL to 1.40 g/mL, or from 1.00 g/mL to 1.20 g/mL.

Bulk density can be determined using a bulk density cylinder.

Smooth microparticle surfaces facilitate the ability to coat the microparticles with a thin, continuous functional coating having a substantially homogeneous thickness. The qualities of the coating can be important for modified or controlled release formulations. For example, rough and/or porous surfaces tend to require a significantly higher amount of a functional coating to achieve a comparable release profile to smooth surfaces. In addition, coatings of rough and/or porous surfaces can lead to a variable dissolution or release profile.

A plurality of uncoated immediate release microparticles provided by the present disclosure can be characterized by a loss on drying (LOD), for example, from 0.92 to 0.98, from 0.93 to 0.97, or from 0.94 to 0.96. The LOD represents removal of water incorporated into the microparticles during preparation of the uncoated microparticles. LOD is determined by thermogravimetric analysis.

A plurality of uncoated immediate release microparticles provided by the present disclosure can be characterized by a friability value, for example, from 0% to 2%, such as less than 2%, less than 1%, or less than 0.5%. Microparticles with low friability are easier to coat than are microparticles with high friability. Friability is defined as the number of microparticles having a diameter less than 75 μm that are generated by subjecting a granulation to a sonic sifter operated at a vibration amplitude of 8 corresponding to 3,600 sonic energy pulses per minute for at least 2 minutes.

A plurality of uncoated immediate release microparticles provided by the present disclosure can have a friability, for example, of 1.02% where friability is determined using a sonic sifter.

Methods of making uncoated immediate release microparticles provided by the present disclosure are disclosed in U.S. Application Publication No. 2021/039357 A1.

An immediate release component can comprise immediate release microparticles or an immediate release formulation can be prepared by dissolving immediate release microparticles in a solution suitable for oral administration.

Immediate release microparticles can have an average particle size distribution (PSD) (D50) from 150 μm to 400 μm, from 150 μm to 350 μm, from 150 μm to 300 μm, or from 150 μm to 250 μm, where PSD is determined by sieve analysis.

Immediate release microparticles can have, for example, a volume mean diameter D(4,3) from 200 μm to 500 μm or from 250 μm to 450 μm.

The core of an immediate release microparticle can comprise, for example, greater than 90 wt %, such as greater than 92 wt %, greater than 94 wt %, greater than 96 wt %, greater than 98 wt %, or greater than 99 wt % of compound (1), where wt % is based on the total weight of the core of the immediate release microparticle.

An immediate release microparticle can comprise a thin protective coating such as a seal coating.

An immediate release microparticle can comprise a plurality of uncoated immediate release microparticles. An immediate release microparticle comprising can comprise greater than 90 wt % of compound (1), where wt % is based on the total weight of the microparticle. An immediate release uncoated microparticle can dissolve completely, for example, in less than 10 minutes, less than 8 minutes, less than 6 minutes, less than 5 minutes, or less than 4 minutes, when tested in a USP Type 2 dissolution apparatus in a buffered solution at pH 4.5 at a temperature of 37° C. and a paddle speed of 75 rpm.

An immediate release microparticle can have an immediate release coating such as a seal coating. An immediate release microparticle can comprise greater than 80 wt % of compound (1). An immediate release microparticle can dissolve completely, for example, in less than 25 minutes, less than 20 minutes, less than 18 minutes, less than 16 minutes, less than 14 minutes, or less than 12 minutes, when tested in a USP Type 2 dissolution apparatus in a buffered solution at pH 4.5 at a temperature of 37° C. and a paddle speed of 75 rpm. An immediate release microparticle can release greater than 80% of compound (1), for example, in less than 10 minutes, less than 8 minutes, less than 6 minutes, or less than 4 minutes, when tested in a USP Type 2 dissolution apparatus in a buffered solution at pH 4.5 at a temperature of 37° C. and a paddle speed of 75 rpm.

A coated immediate release microparticle can comprise a coating comprising a water-soluble polymer such as, for example, hydroxypropyl cellulose, polyvinyl alcohol, hydroxypropylmethyl cellulose, hydroxypropylethyl cellulose, polyvinylpyrrolidone, or polyethyleneglycol. A coated immediate release microparticle can comprise a coating comprising an antistatic agent such as talc, magnesium stearate, or silicon dioxide.

An immediate release microparticle can dissolve in a solution suitable for oral administration.

A modified release component can comprise modified release microparticles. For example, a modified release component can comprise modified release microparticles suspended in a solution suitable for oral administration.

Modified release microparticles comprise a modified release coating. Modified release microparticles comprising 4-((L-valyl)oxy)butanoic acid (1), methods of preparing the modified release microparticles, and properties of the modified release microparticles are disclosed in U.S. Application Publication No. 2021/0393537 A1 and U.S. Application Publication No. 2021/0393529 A1.

A modified release microparticle can comprise an uncoated immediate release microparticle with an overlying modified release coating. A modified release microparticle can comprise an immediate release microparticle having a seal coating, and a modified release coating overlying the seal coating.

A modified release coating can have an average thickness, for example, of less than 300 μm, less than 200 μm, less than 150 μm, less than 100 μm, less than 50 μm, less than 25 μm, less than 20 μm, less than 10 μm, or less than 5 μm. A modified release coating can have an average thickness, for example, from 5 μm to 300 μm, from 5 μm to 200 μm, from 5 μm to 100 μm, from 5 μm to 50 μm, from 5 μm to 25 μm, from 5 μm to 20 μm, or from 5 μm to 15 μm.

A modified release microparticle can comprise, for example, less than 50 wt % of a modified release coating, less than 40 wt % of a modified release coating, less than 30 wt %, less than 20 wt %, or less than 10 wt % of a modified release coating, where wt % is based on the total weight of the modified release microparticle. Dosage forms containing a highly water-soluble pharmaceutically active ingredient such as compound (1) can have a thick coating to reduce the release rate of the pharmaceutically active ingredient and/or increase the storage stability of the pharmaceutically active ingredient by minimizing or preventing ingress of moisture.

A modified release microparticle can comprise, for example, greater than 60 wt % of compound (1), greater than 70 wt %, greater than 80 wt %, or greater than 85 wt % of compound (1), where wt % is based on the total weight of the modified release microparticle.

A modified release microparticle can comprise, for example, from 60 wt % to 85 wt % of compound (1), from 65 wt % to 80 wt %, or from 70 wt % to 75 wt % of compound (1), where wt % is based on the total weight of the modified release microparticle.

A modified release microparticle can comprise, for example, from 5 wt % to 40 wt % of a modified release coating, from 10 wt % to 35 wt %, from 15 wt % to 30 wt %, or from 20 wt % to 25 wt % of a modified release coating, where wt % is based on the total weight of the modified release microparticle. A modified release microparticle can comprise, for example, greater than 5 wt % of a modified release coating, greater than 10 wt %, greater than 15 wt %, greater than 20 wt %, greater than 25 wt %, or greater than 30 wt % of a modified release coating, where wt % is based on the total weight of the modified release microparticle. A modified release microparticle can comprise, for example, less than 40 wt % of a modified release coating, less than 35 wt %, less than 30 wt %, less than 25 wt %, less than 20 wt %, less than 15 wt %, or less than 10 wt % of a modified release coating, where wt % is based on the total weight of the modified release coating.

A modified release microparticle can comprise, for example, from 60 wt % to 95 wt % of an uncoated immediate release microparticle, from 65 wt % to 90 wt %, from 70 wt % to 85 wt %, or from 75 wt % to 80 wt % of an uncoated immediate release microparticle, where wt % is based on the total weight of the modified release microparticle. A modified release microparticle can comprise, for example, greater than 60 wt % of an uncoated immediate release microparticle, greater than 65 wt %, greater than 70 wt %, greater than 75 wt %, greater than 80 wt %, greater than 85 wt %, or greater than 90 wt % of an immediate release microparticles, where wt % is based on the total weight of the modified release microparticle.

A modified release coating can comprise, for example, a matrix polymer, an anti-static agent, and a plasticizer.

A modified release coating can comprise a matrix polymer or combination of matrix polymers. A combination of a matrix polymer and/or a pore forming polymer can be selected to provide for a desired release profile of compound (1) in the gastrointestinal tract.

A modified release coating can comprise, for example, from 60 wt % to 85 wt % of a matrix polymer, from 65 wt % to 80 wt %, or from 70 wt % to 80 wt %, of a matrix polymer, where wt % is based on the total weight of the modified release coating.

A modified release coating can comprise, for example, less than 85 wt % of a matrix polymer, less than 80 wt %, less than 75 wt %, less than 70 wt %, or less than 65 wt % of a matrix polymer, where wt % is based on the total weight of the modified release coating.

A modified release coating can comprise, for example, greater than 60% of a matrix polymer, greater than 65 wt %, greater than 70 wt %, greater than 75 wt %, or greater than 80 wt % of a matrix polymer, where wt % is based on the total weight of the modified release coating.

A matrix polymer can comprise a water-insoluble polymer or combination of water-insoluble polymers.

Examples of suitable water insoluble polymers include ethylcellulose and polyvinyl acetates, polyacrylates, and polymethacrylates.

A water insoluble polymer such as ethylcellulose can have a number average molecular weight, for example, from 25,000 Daltons, to 300,000 Daltons, such as from 50,000 Daltons to 200,000 Daltons, from 50,000 Daltons to 150,000 Daltons, or from 50,000 Daltons to 100,000 Daltons.

A water insoluble polymer such as ethylcellulose can have a viscosity, for example, less than 100 mPa×sec, less than 75 mPa×sec, less than 50 mPa×sec, less than 25 mPa×sec, less than 20 mPa×sec, or less than 15 mPa×sec, as determined using a Brookfield viscometer in an 80:20 mixture of toluene/ethanol.

Examples of suitable ethylcellulose polymers include AQUALON® T10 Pharm, N7 Pharm, N10 Pharm, N14 Pharm, N22 Pharm, N50 Pharm, and N100 Pharm polymers, available from Ashland. Other examples of suitable ethylcellulose polymers include ETHOCEL® Standard 7, Standard 10, Standard 14, Standard 20 polymers, available from Dupont.

A matrix polymer can comprise, for example, from 90 wt % to 100 wt % of a water-insoluble polymer, from 91 wt % to 99 wt %, from 82 wt % to 98 wt %, or from 93 wt % to 97 wt % of a water-insoluble polymer, where wt % is based on the total weight of the matrix polymer. A matrix polymer can comprise, for example, greater than 90 wt % of a water insoluble polymer, greater than 92 wt %, greater than 94 wt %, greater than 96 wt %, or greater than 98 wt % of a water insoluble polymer, where wt % is based on the total weight of the matrix polymer. A matrix polymer can comprise, for example less than 100 wt % of a water insoluble polymer, less than 98 wt %, less than 96 wt %, less than 94 wt %, or less than 92 wt % of a water insoluble polymer, where wt % is based on the total weight of the matrix polymer.

A matrix polymer can comprise a pore forming polymer. Examples of pore forming polymers include water-soluble polymers, polymers that swell or expand such as carbomers, and polymers soluble in gastric fluid such as cellulose acetate phthalate, hydroxypropylcellulose, hydroxypropyl methyl cellulose, methacrylic acid-methyl methacrylate copolymers, and polyvinyl acetate phthalate. A pore forming polymer can increase the permeability of a modified release coating under intended conditions.

A matrix polymer can comprise a water-soluble polymer or combination of water-soluble polymers.

Examples of suitable water-soluble polymers include hydroxypropyl cellulose, polyvinyl alcohol, hydroxypropylmethyl cellulose, hydroxypropylethyl cellulose, polyvinylpyrrolidone, polyethylene glycol, polyvinyl alcohol, povidone, copovidone, and poloxamer.

A water-soluble polymer such as hydroxypropylcellulose can have a number average molecular weight, for example less than 1,000,000 Daltons, less than 800,000 Daltons, less than 600,000 Daltons, less than 400,000 Daltons, less than 200,000 Daltons, less than 100,000 Daltons, or less than 50,0000 Daltons.

A water-soluble polymer such as hydroxypropyl cellulose can have a viscosity, for example less than 7,000 mPa×sec, less than 5,000 mPa×sec, less than 3,000 mPa×sec, or less than 1,000 mPa×sec, as determined using a Brookfield viscometer in an 80:20 mixture of toluene/ethanol.

Examples of suitable hydroxypropyl cellulose polymers include KLUCEL® H F Pharm, M F Pharm, G F Pharm J F Pharm, L F Pharm, E F Pharm, and E L F Pharm polymers, available from Ashland.

Examples of suitable hydroxypropylmethyl cellulose polymers include PHARMACOAT® 603, 645, 606 and 615 polymers, available from Shin-Etsu Chemical Co.

A matrix polymer can comprise, for example, from 90 wt % to 100 wt % of a water insoluble polymer and from 0 wt % to 10 wt %, from 1 wt % to 8 wt %, or from 2 wt % to 6 wt % of a water-soluble polymer, where wt % is based on the total weight of the matrix polymer. A matrix polymer can comprise, for example, greater than 0 wt % of a water-soluble polymer, greater than 2 wt %, greater than 4 wt %, greater than 6 wt %, or greater than 8 wt % of a water-soluble polymer, where wt % is based on the total weight of the matrix polymer. A matrix polymer can comprise, for example, less than 10 wt % of a water-soluble polymer, less than 8 wt %, less than 6 wt %, less than 4 wt %, or less than 2 wt % of a water-soluble polymer, where wt % is based on the total weight of the matrix polymer, where wt % is based on the total weight of the matrix polymer.

A matrix polymer can comprise, for example, from 90 wt % to 100 wt % of a water-insoluble polymer and from 0 wt % to 10 wt % of a water-soluble polymer, from 92 wt % to 98 wt % of a water-insoluble polymer and from 2 wt % to 8 wt % of a water-soluble polymer, or from 94 wt % to 96 wt % of a water-insoluble polymer and from 4 wt % to 6 wt % of a water-soluble polymer, where wt % is based on the total weight of the matrix polymer.

A modified release coating can be applied to immediate release microparticles provided by the present disclosure by any suitable method such as by spraying a solution, suspension, or dispersion of the modified release coating onto immediate release microparticles in a fluidized bed apparatus.

In addition to a matrix polymer or combination of matrix polymers, a modified release coating can comprise, for example, a plasticizing agent, an antistatic agent, an anti-tacking agent, a colorant or pigment, a glidant, a viscosity modifier, or a combination of any of the foregoing.

A modified release coating can comprise an antistatic agent or combination of antistatic agents.

An antistatic agent is useful to minimize or prevent agglomeration of the microparticles during application of the modified release coating.

Examples of suitable antistatic agents include talc (magnesium silicate), magnesium stearate, and silicon dioxide. For example, an antistatic agent can comprise talc.

A modified release coating can comprise, for example, from 10 wt % to 20 wt % of an antistatic agent, such as from 12 wt % to 18 wt %, or from 14 wt % to 16 wt % of an antistatic agent, where wt % is based on the total weight of the modified release coating. A modified release coating can comprise, for example, less than 20 wt % of an antistatic agent, less than 18 wt %, less than 16 wt %, less than 14 wt % or less than 12 wt % of an antistatic agent, where wt % is based on the total weight of the modified release coating. A modified release coating can comprise, for example, greater than 10 wt % of an antistatic agent, greater than 12 wt %, greater than 14 wt %, greater than 16 wt %, or greater than 18 wt % of an antistatic agent, where wt % is based on the total weight of the modified release coating.

A modified release coating can comprise a plasticizer or combination of plasticizers.

A plasticizer is useful to provide a modified release coating having a uniform thickness.

Examples of suitable plasticizers include dibutyl sebacate, polyethylene glycol, triacetin, and triethyl citrate.

A modified release coating can comprise, for example, from 0 wt % to 14 wt % of a plasticizer, such as from 2 wt % to 12 wt %, or from 4 wt % to 10 wt % of a plasticizer, where wt % is based on the total weight of the modified release coating. A modified release coating can comprise, for example, less than 14 wt % of a plasticizer, less than 12 wt %, less than 12 wt %, less than 8 wt %, less than 6 wt %, or less than 4 wt % of a plasticizer, where wt % is based on the total weight of the modified release coating. A modified release coating can comprise, for example, greater than 0 wt % of a plasticizer, greater than 2 wt %, greater than 4 wt %, greater than 6 wt %, greater than 8 wt %, greater than 10 wt %, or greater than 12 wt % of a plasticizer, where wt % is based on the total weight of the modified release coating.

A modified release coating provided by the present disclosure can comprise, for example, from 60 wt % to 85 wt % of a matrix polymer, from 10 wt % to 20 wt % of an antistatic agent, and from 0 wt % to 14 wt % of a plasticizer, where wt % is based on the total weight of the modified release coating.

A modified release coating provided by the present disclosure can comprise, for example, from 65 wt % to 80 wt % of a matrix polymer, from 12 wt % to 18 wt % of an antistatic agent, and from 2 wt % to 12 wt % of a plasticizer, where wt % is based on the total weight of the modified release coating.

A modified release coating provided by the present disclosure can comprise, for example, from 70 wt % to 80 wt % of a matrix polymer, from 14 wt % to 16 wt % of an antistatic agent, and from 4 wt % to 10 wt % of a plasticizer, where wt % is based on the total weight of the modified release coating.

In a modified release coating the matrix polymer can comprise ethylcellulose and hydroxypropyl cellulose, the plasticizer can comprise dibutyl sebacate, and the antistatic agent can comprise talc.

In a modified release coating the matrix polymer can comprise ethylcellulose and hydroxypropyl cellulose, the antistatic agent can comprise magnesium stearate, and there can be no plasticizer.

A coated immediate release microparticle can comprise a seal coating overlying the immediate release microparticle comprising the pharmaceutically active ingredient. A modified release coating can overly the seal coating.

A seal coating can minimize the ingress of moisture into the pharmaceutically active ingredient and thereby increase the storage stability of the coated microparticle by reducing hydrolysis of the pharmaceutically active ingredient. A seal coating can also minimize negative interactions between the modified release coating and the pharmaceutically active ingredient, and thereby increase the storage stability of the coated microparticle by reducing hydrolysis of the pharmaceutically active ingredient such as compound (1).

A seal coating can comprise a water-soluble polymer such as, for example, hydroxypropylcellulose, polyvinyl alcohol, hydroxypropylmethyl cellulose, hydroxypropylethyl cellulose, polyvinylpyrrolidone, or polyethylene glycol.

A seal coating can have an average thickness, for example from 0.5 μm to 5 μm, from 1 μm to 4 μm, or from 1 μm to 3 μm. A seal coating can have an average thickness, for example, less than 5 μm, less than 4 μm, less than 3 μm, less than 2 μm, or less than 1 μm.

A seal coating can be applied to an immediate release microparticle such that the % wg is less than 15% wg, less than 10% wg, less than 8% wg, less than 6% wg, or less than 4% wg, where % wg is based on the weight of the uncoated immediate release microparticle. A seal coating can be applied to a microparticle such that the % wg is from 1% wg to 15% wg, from 1% wg to 10% wg, from 2% wg to 8% wg, or from 4% wg to 6% wg, where % wg is based on the weight of the uncoated immediate release microparticle.

In a coated immediate release microparticle comprising a seal coating comprising a water-soluble polymer, the modified release coating may not contain a water-soluble polymer.

A modified release microparticle provided by the present disclosure can have a water content, for example, less than 2 wt %, less than 1.5 wt % less than 1 wt %, less than 0.5 wt % or less than 0.25 wt %, where wt % is based on the total weight of the modified release microparticle.

A modified release microparticle provided by the present disclosure can have a water content, for example, from 0.1 wt % to 2 wt %, from 0.1 wt % to 1 wt %, or from 0.2 wt % to 0.5 wt %, where wt % is based on the total weight of the modified release microparticle.

A modified release microparticle can have a bulk density, for example, greater than 0.55 g/mL, greater than 0.60 g/mL, greater than 0.65 g/mL, greater than 0.70 g/mL, or greater than 0.75 g/mL.

A modified release microparticle can have a bulk density, for example, from 0.55 g/mL to 0.80 g/mL, from 0.60 g/mL to 75 g/mL, from 0.60 g/mL to 0.70 g/mL.

Bulk density can be determined using a bulk density cylinder.

A modified release microparticle provided by the present disclosure can have a water content, for example, less than 2 wt %, less than 1.5 wt % less than 1 wt %, less than 0.5 wt % or less than 0.25 wt %, where wt % is based on the total weight of the modified release microparticle.

A modified release microparticle provided by the present disclosure can have a water content, for example, from 0.1 wt % to 2 wt %, from 0.1 wt % to 1 wt %, or from 0.2 wt % to 0.5 wt %, where wt % is based on the total weight of the modified release microparticle.

A modified release microparticle can have a bulk density, for example, greater than 0.55 g/mL, greater than 0.60 g/mL, greater than 0.65 g/mL, greater than 0.70 g/mL, or greater than 0.75 g/mL.

A modified release microparticle can have a bulk density, for example, from 0.55 g/mL to 0.80 g/mL, from 0.60 g/mL to 75 g/mL, from 0.60 g/mL to 0.70 g/mL.

Bulk density can be determined using a bulk density cylinder.

A modified release microparticle provided by the present disclosure can be characterized, for example, by a PSD (D50), for example, from 150 µm to 350 µm, such as from 175 µm to 325 µm, from 200 µm to 300 µm, or from 225 µm to 275 µm.

A modified release microparticle can be characterized, for example, by a PSD (D10) from 50 µm to 150 µm, from 60 µm to 140 µm, from 70 µm, to 120 µm, or from 80 µm to 110 µm.

An uncoated microparticle can be characterized, for example, by a PSD (D90) from 450 µm to 750 µm, from 475 µm to 725 µm, from 500 µm to 700 µm, from 525 µm to 675 µm, or from 550 µm to 650 µm.

A modified release microparticle can be characterized, for example, by a PSD (D10) from 50 µm to 150 µm such as from 60 µm to 140 µm; a PSD (D50) from 230 µm to 310 µm; and a PSD (D90) from 490 µm to 550 µm.

A modified release microparticle can be characterized, for example, by a PSD (D10) from 70 µm to 130 µm; a PSD (D50) from 240 µm to 300 µm; and a PSD (D90) from 500 µm to 540 µm.

A particle size distribution can be determined by laser diffraction or by sieve analysis.

A modified release microparticle (MR1) provided by the present disclosure can be characterized by a dissolution profile in which from 70% to 90% of compound (1) is released into the dissolution media within 2 hours, from 85% to 100% within 4 hours, and greater than 95% within 6 hours, as determined using a USP Type 2 dissolution apparatus with a buffered solution at pH 4.5 at a temperature of 37° C. and a paddle speed of 75 rpm.

A modified release microparticle (MR1) provided by the present disclosure can be characterized by a dissolution profile in which from 75% to 85% of compound (1) is released into the dissolution media within 2 hours, from 90% to 100% within 4 hours, and greater than 95% within 6 hours, as determined using a USP Type 2 dissolution apparatus with a buffered solution at pH 4.5 at a temperature of 37° C. and a paddle speed of 75 rpm.

A modified release microparticle (MR2) provided by the present disclosure can be characterized by a dissolution profile in which from 45% to 65% of compound (1) is released into the dissolution media within 2 hours, from 70% to 90% within 4 hours, from 80% to 100% within 6 hours, and greater than 90% within 8 hours, as determined using a USP Type 2 dissolution apparatus with a buffered solution at pH 4.5 at a temperature of 37° C. and a paddle speed of 75 rpm.

A modified release microparticle (MR2) provided by the present disclosure can be characterized by a dissolution profile in which from 50% to 60% of compound (1) is released into the dissolution media within 2 hours, from 75% to 85% within 4 hours, from 85% to 95% within 6 hours, and greater than 90% within 8 hours, as determined using a USP Type 2 dissolution apparatus with a buffered solution at pH 4.5 at a temperature of 37° C. and a paddle speed of 75 rpm.

A modified release microparticle (MR3) provided by the present disclosure can be characterized by a dissolution profile in which from 25% to 45% of compound (1) is released into the dissolution media within 2 hours, from 60% to 80% within 4 hours, from 70% to 90% within 6 hours, from 80% to 100% within 8 hours and greater than 90% within 12 hours, as determined using a USP Type 2 dissolution apparatus with a buffered solution at pH 4.5 at a temperature of 37° C. and a paddle speed of 75 rpm.

A modified release microparticle (MR3) provided by the present disclosure can be characterized by a dissolution profile in which from 30% to 40% of compound (1) is released into the dissolution media within 2 hours, from 65% to 75% within 4 hours, from 75% to 85% within 6 hours, from 85% to 95% within 8 hours and greater than 90% within 12 hours, as determined using a USP Type 2 dissolution apparatus with a buffered solution at pH 4.5 at a temperature of 37° C. and a paddle speed of 75 rpm.

A modified release microparticle can release, for example, 25% of compound (1) in less than 2 hours, 50% of compound (1) in from 1 hours to 4 hours, 75% of compound (1) in from 1.5 hours to 6 hours, and greater than 85% of compound (1) from the modified release particle into the dissolution medium, as determined using a USP Type 2 dissolution apparatus with a buffered solution at pH 4.5 at a temperature of 37° C. and a paddle speed of 75 rpm.

A modified release macroparticle can release, for example, greater than 20% of compound (1) in two hours, greater than 50% within 4 hours, greater than 70% within 6 hours, greater than 80% within 8 hours, and greater than 90% within 10 hours, as determined using a USP Type 2 dissolution apparatus with a buffered solution at pH 4.5 at a temperature of 37° C. and a paddle speed of 75 rpm.

Following oral administration of an IR formulation comprising 7.25 g of compound (1) to a population of fasted, healthy subjects a pharmacokinetic profile of compound (1) can be characterized by a mean $t_{1/2}$ of 0.45 hours, a mean $T_{max}$ of 0.6 hours, a mean $C_{max}$ of 18 µg/mL, a mean $AUC_{0-6}$ of 16 h×µg/mL, an $AUC_{0-inf}$ of 16 h×µg/mL, and/or a CL/F of 501 L/h.

Following oral administration of an IR formulation comprising 7.25 g of compound (1) to a population of fasted, healthy subjects a pharmacokinetic profile of compound (1) can be characterized by a mean $t_{1/2}$ of from 0.35 hours to 0.55 hours, a mean $T_{max}$ from 0.5 hours to 0.7 hours, a mean $C_{max}$ from 16 µg/mL to 20 µg/mL, a mean $AUC_{0-6}$ from 14 h×µg/mL to 18 h×µg/mL, an $AUC_{0-inf}$ from 14 h×µg/mL to 18 h×µg/mL, and/or a CL/F of 480 L/h to 520 L/h.

Following oral administration of an IR formulation comprising 7.25 g of compound (1) to a population of fasted, healthy subjects a pharmacokinetic profile of compound (1) can be characterized by a mean $t_{1/2}$ of from 0.4 hours to 0.5 hours, a mean $T_{max}$ from 0.55 hours to 0.65 hours, a mean $C_{max}$ from 17 µg/mL to 19 µg/mL, a mean $AUC_{0-6}$ from 15 h×µg/mL to 17 h×µg/mL, an $AUC_{0-inf}$ from 15 h×µg/mL to 17 h×µg/mL, and/or a CL/F of 490 L/h to 510 L/h.

Following oral administration of an MR1 formulation comprising 7.25 g of compound (1) to a population of fasted, healthy subjects a pharmacokinetic profile of compound (1) can be characterized by a mean $t_{1/2}$ of 0.87 hours, a mean $T_{max}$ of 1.3 hours, a mean $C_{max}$ of 8 µg/mL, a mean $AUC_{0-6}$ of 15 h×µg/mL, a mean $AUC_{0-inf}$ of 15 h×µg/mL, and/or a mean CL/F of 514 L/h.

Following oral administration of an MR1 formulation comprising 7.25 g of compound (1) to a population of fasted, healthy subjects a pharmacokinetic profile of compound (1) can be characterized by a mean $t_{1/2}$ from 0.7 hours to 1.1 hours, a mean $T_{max}$ from 1.1 hours to 1.5 hours, a mean $C_{max}$ from 0.6 µg/mL to 1.0 µg/mL, a mean $AUC_{0-6}$ from 13 h×µg/mL to 17 h×µg/mL, a mean $AUC_{0-inf}$ from 13 h×µg/mL to 17 h×µg/mL, and/or a mean CL/F from 495 L/h to 535 L/h.

Following oral administration of an MR1 formulation comprising 7.25 g of compound (1) to a population of fasted, healthy subjects a pharmacokinetic profile of compound (1) can be characterized by a mean $t_{1/2}$ from 0.8 hours to 1.0 hours, a mean $T_{max}$ from 1.2 hours to 1.4 hours, a mean $C_{max}$ from 0.7 µg/mL to 0.9 µg/mL, a mean $AUC_{0-6}$ from 14 h×µg/mL to 16 h×µg/mL, a mean $AUC_{0-inf}$ from 14 h×µg/mL to 16 h×µg/mL, and/or a mean CL/F from 505 L/h to 525 L/h.

Following oral administration of an MR2 formulation comprising 7.25 g of compound (1) to a population of fasted, healthy subjects a pharmacokinetic profile of compound (1) can be characterized by a mean $t_{1/2}$ of 0.82 hours, a mean $T_{max}$ of 1.6 hours, a mean $C_{max}$ of 5 µg/mL, a mean $AUC_{0-6}$ of 12 h×µg/mL, a mean $AUC_{0-inf}$ 12 h×µg/mL, and/or a mean CL/F of 642 L/h.

Following oral administration of an MR2 formulation comprising 7.25 g of compound (1) to a population of fasted, healthy subjects a pharmacokinetic profile of compound (1) can be characterized by a mean $t_{1/2}$ from 0.6 hours to 1.0 hours, a mean $T_{max}$ from 1.4 hours to 1.8 hours, a mean $C_{max}$ from 3 µg/mL to 7 µg/mL, a mean $AUC_{0-6}$ from 10 h×µg/mL to 14 h×µg/mL, a mean $AUC_{0-inf}$ from 10 h×µg/mL to 14 h×µg/mL, and/or a mean CL/F from 620 L/h to 660 L/h.

Following oral administration of an MR2 formulation comprising 7.25 g of compound (1) to a population of fasted, healthy subjects a pharmacokinetic profile of compound (1) can be characterized by a mean $t_{1/2}$ from 0.7 hours to 0.9 hours, a mean $T_{max}$ from 1.5 hours to 1.7 hours, a mean $C_{max}$ from 4 µg/mL to 6 µg/mL, a mean $AUC_{0-6}$ from 9 h×µg/mL to 11 h×µg/mL, a mean $AUC_{0-inf}$ from 11 h×µg/mL to 13 h×µg/mL, and/or a mean CL/F from 630 L/h to 650 L/h.

Following oral administration of an MR3 formulation comprising 7.25 g of compound (1) to a population of fasted, healthy subjects a pharmacokinetic profile of compound (1) can be characterized by a mean $t_{1/2}$ of 1.01 hours, a mean $T_{max}$ of 2.3 hours, a mean $C_{max}$ of 3.7 µg/mL, a mean $AUC_{0-6}$ of 10 h×µg/mL, a mean $AUC_{0-inf}$ 11 h×µg/mL, and/or a mean CL/F of 715 L/h.

Following oral administration of an MR3 formulation comprising 7.25 g of compound (1) to a population of fasted, healthy subjects a pharmacokinetic profile of compound (1) can be characterized by a mean $t_{1/2}$ from 0.8 hours to 1.2 hours, a mean $T_{max}$ from 2.1 hours to 2.5 hours, a mean $C_{max}$ from 3.5 µg/mL to 3.9 µg/mL, a mean $AUC_{0-6}$ from 8 h×µg/mL to 12 h×µg/mL, a mean $AUC_{0-inf}$ from 9 h×µg/mL to 13 h×µg/mL, and/or a mean CL/F from 695 L/h to 735 L/h.

Following oral administration of an MR3 formulation comprising 7.25 g of compound (1) to a population of fasted, healthy subjects a pharmacokinetic profile of compound (1) can be characterized by a mean $t_{1/2}$ from 0.9 hours to 1.1 hours, a mean $T_{max}$ from 2.2 hours to 2.4 hours, a mean $C_{max}$ from 3.6 µg/mL to 3.8 µg/mL, a mean $AUC_{0-6}$ from 9 h×µg/mL to 11 h×µg/mL, a mean $AUC_{0-inf}$ from 10 h×µg/mL to 12 h×µg/mL, and/or a mean CL/F from 705 L/h to 725 L/h.

Following oral administration of an IR formulation comprising 7.25 g of compound (1) to a population of fasted, healthy subjects a pharmacokinetic profile of γ-hydroxybutyrate can be characterized by a mean $t_{1/2}$ of 0.66 hours, a mean $T_{max}$ of 0.9 hours, a mean $C_{max}$ of 83 µg/mL, an $AUC_{0-6}$ of 167 h×µg/mL, an $AUC_{0-inf}$ of 168 h×µg/mL, and/or a CL/F of 48.5 L/h.

Following oral administration of an IR formulation comprising 7.25 g of compound (1) to a population of fasted, healthy subjects a pharmacokinetic profile of γ-hydroxybutyrate can be characterized by a mean $t_{1/2}$ from 0.45 hours to 0.85 hours, a mean $T_{max}$ from 0.7 hours to 1.1 hours, a mean $C_{max}$ from 75 µg/mL to 96 µg/mL, an $AUC_{0-6}$ from 147 h×µg/mL to 187 h×µg/mL, an $AUC_{0-inf}$ from 150 h×µg/mL to 190 h×µg/mL, and/or a CL/F from 38 L/h to 58 L/h.

Following oral administration of an IR formulation comprising 7.25 g of compound (1) to a population of fasted, healthy subjects a pharmacokinetic profile of γ-hydroxybutyrate can be characterized by a mean $t_{1/2}$ from 0.55 hours to 0.75 hours, a mean $T_{max}$ from 0.9 hours to 1.0 hours, a mean $C_{max}$ from 80 µg/mL to 90 µg/mL, an $AUC_{0-6}$ from 157 h×µg/mL to 177 h×µg/mL, an $AUC_{0-inf}$ from 160 h×µg/mL to 180 h×µg/mL, and/or a CL/F from 43 L/h to 53 L/h.

Following oral administration of an MR1 formulation comprising 7.25 g of compound (1) to a population of fasted, healthy subjects a pharmacokinetic profile of γ-hydroxybutyrate can be characterized by a mean $t_{1/2}$ of 0.85 hours, a mean $T_{max}$ of 1.7 hours, a mean $C_{max}$ of 42 µg/mL, a mean $AUC_{0-6}$ of 116 h×µg/mL, a mean $AUC_{0-inf}$ of 120 h×µg/mL, and/or a mean CL/F of 82 L/h.

Following oral administration of an MR1 formulation comprising 7.25 g of compound (1) to a population of fasted, healthy subjects a pharmacokinetic profile of γ-hydroxybutyrate can be characterized by a mean $t_{1/2}$ from 0.65 hours to 1.05 hours, a mean $T_{max}$ from, 1.5 hours to 1.9 hours, a mean $C_{max}$ from 32 μg/mL to 52 μg/mL, a mean $AUC_{0-6}$ from 96 h×μg/mL to 136 h×μg/mL, a mean $AUC_{0-inf}$ from 100 h×μg/mL to 140 h×μg/mL, and/or a mean CL/F from 62 L/h to 102 L/h.

Following oral administration of an MR1 formulation comprising 7.25 g of compound (1) to a population of fasted, healthy subjects a pharmacokinetic profile of γ-hydroxybutyrate can be characterized by a mean $t_{1/2}$ from 0.75 hours to 0.95 hours, a mean $T_{max}$ from 1.6 hours to 1.8 hours, a mean $C_{max}$ from 37 μg/mL to 47 μg/mL, a mean $AUC_{0-6}$ from 106 h×μg/mL to 126 h×μg/mL, a mean $AUC_{0-inf}$ from 110 h×μg/mL to 130 h×μg/mL, and/or a mean CL/F from 72 L/h to 92 L/h.

Following oral administration of an MR2 formulation comprising 7.25 g of compound (1) to a population of fasted, healthy subjects a pharmacokinetic profile of γ-hydroxybutyrate can be characterized by a mean $t_{1/2}$ of 1.0 hour, a mean $T_{max}$ of 2.3 hours, a mean $C_{max}$ of 25 μg/mL, a mean $AUC_{0-6}$ of 73 h×μg/mL, a mean $AUC_{0-inf}$ 76 h×μg/mL, and/or a mean CL/F of 119 L/h.

Following oral administration of an MR2 formulation comprising 7.25 g of compound (1) to a population of fasted, healthy subjects a pharmacokinetic profile of γ-hydroxybutyrate can be characterized by a mean $t_{1/2}$ from 0.8 hours to 1.2 hour, a mean $T_{max}$ from 2.1 hours to 2.5 hours, a mean $C_{max}$ from 23 μg/mL to 27 μg/mL, a mean $AUC_{0-6}$ from 63 h×μg/mL to 83 h×μg/mL, a mean $AUC_{0-inf}$ from 66 h×μg/mL to 86 h×μg/mL, and/or a mean CL/F from 100 L/h to 140 L/h.

Following oral administration of an MR2 formulation comprising 7.25 g of compound (1) to a population of fasted, healthy subjects a pharmacokinetic profile of γ-hydroxybutyrate can be characterized by a mean $t_{1/2}$ from 0.9 hours to 1.1 hour, a mean $T_{max}$ from 2.2 hours to 2.4 hours, a mean $C_{max}$ from 24 μg/mL to 26 μg/mL, a mean $AUC_{0-6}$ from 68 h×μg/mL to 78 h×μg/mL, a mean $AUC_{0-inf}$ from 71 h×μg/mL to 81 h×μg/mL, and/or a mean CL/F from 110 L/h to 130 L/h.

Following oral administration of an MR3 formulation comprising 7.25 g of compound (1) to a population of fasted, healthy subjects a pharmacokinetic profile of γ-hydroxybutyrate can be characterized by a mean $t_{1/2}$ of 1.5 hours, a mean $T_{max}$ of 3.0 hours, a mean $C_{max}$ of 16 μg/mL, a mean $AUC_{0-6}$ of 49 h×μg/mL, a mean $AUC_{0-inf}$ of 55 h×μg/mL, and/or a mean CL/F of 146 L/h.

Following oral administration of an MR3 formulation comprising 7.25 g of compound (1) to a population of fasted, healthy subjects a pharmacokinetic profile of γ-hydroxybutyrate can be characterized by a mean $t_{1/2}$ from 1.3 hours to 1.7 hours, a mean $T_{max}$ from 2.8 hours to 3.2 hours, a mean $C_{max}$ from 14 μg/mL to 18 μg/mL, a mean $AUC_{0-6}$ from 45 h×μg/mL to 53 h×μg/mL, a mean $AUC_{0-inf}$ from 51 h×μg/mL to 59 h×μg/mL, and/or a mean CL/F from 136 L/h to 156 L/h.

Following oral administration of an MR3 formulation comprising 7.25 g of compound (1) to a population of fasted, healthy subjects a pharmacokinetic profile of γ-hydroxybutyrate can be characterized by a mean $t_{1/2}$ from 1.4 hours to 1.6 hours, a mean $T_{max}$ from 2.9 hours to 3.1 hours, a mean $C_{max}$ from 15 μg/mL to 17 μg/mL, a mean $AUC_{0-6}$ from 47 h×μg/mL to 51 h×μg/mL, a mean $AUC_{0-inf}$ from 53 h×μg/mL to 57 h×μg/mL, and/or a mean CL/F from 141 L/h to 151 L/h.

Following oral administration of an IR formulation comprising 7.25 g of compound (1) to a population of fasted, healthy subjects a pharmacokinetic profile is characterized by a $C_{max}$ ratio of 4.9, and $AUC_{0-inf}$ ratio of 11.3. Following oral administration of an IR formulation comprising 7.25 g of compound (1) to a population of fasted, healthy subjects a pharmacokinetic profile can be characterized by a $C_{max}$ ratio from 3.9 to 5.9, and $AUC_{0-inf}$ ratio from 10.3 to 12.3. Following oral administration of an IR formulation comprising 7.25 g of compound (1) to a population of fasted, healthy subjects a pharmacokinetic profile can be characterized by a $C_{max}$ ratio from 4.4 to 5.4, and $AUC_{0-inf}$ ratio from 10.8 to 11.8.

Following oral administration of an MR1 formulation comprising 7.25 g of compound (1) to a population of fasted, healthy subjects a pharmacokinetic profile is characterized by a $C_{max}$ ratio of 5.2, and $AUC_{0-inf}$ ratio of 7.6, where the ratio refers to the ratio of the γ-hydroxybutyrate value to the compound (1) value. Following oral administration of an MR1 formulation comprising 7.25 g of compound (1) to a population of fasted, healthy subjects a pharmacokinetic profile is characterized by a $C_{max}$ ratio from 5.0 to 5.4, and $AUC_{0-inf}$ ratio from 7.2 to 8.0, where the ratio refers to the ratio of the γ-hydroxybutyrate value to the compound (1) value. Following oral administration of an MR1 formulation comprising 7.25 g of compound (1) to a population of fasted, healthy subjects a pharmacokinetic profile is characterized by a $C_{max}$ ratio from 5.1 to 5.3, and $AUC_{0-inf}$ ratio from 7.4 to 7.8, where the ratio refers to the ratio of the γ-hydroxybutyrate value to the compound (1) value.

Following oral administration of an MR2 formulation comprising 7.25 g of compound (1) to a population of fasted, healthy subjects a pharmacokinetic profile is characterized by a $C_m a$, ratio of 4.9, and $AUC_{0-inf}$ ratio of 6.3, where the ratio refers to the ratio of the γ-hydroxybutyrate value to the compound (1) value. Following oral administration of an MR2 formulation comprising 7.25 g of compound (1) to a population of fasted, healthy subjects a pharmacokinetic profile is characterized by a $C_{max}$ ratio from 4.5 to 5.3, and $AUC_{0-inf}$ ratio from 5.9 to 6.7, where the ratio refers to the ratio of the γ-hydroxybutyrate value to the compound (1) value. Following oral administration of an MR2 formulation comprising 7.25 g of compound (1) to a population of fasted, healthy subjects a pharmacokinetic profile is characterized by a $C_{max}$ ratio from 4.7 to 5.1, and $AUC_{0-inf}$ ratio from 6.1 to 6.5, where the ratio refers to the ratio of the γ-hydroxybutyrate value to the compound (1) value.

Following oral administration of an MR3 formulation comprising 7.25 g of compound (1) to a population of fasted, healthy subjects a pharmacokinetic profile is characterized by a $C_{max}$ ratio of 4.4, and $AUC_{0-inf}$ ratio of 5.2, where the ratio refers to the ratio of the γ-hydroxybutyrate value to the compound (1) value. Following oral administration of an MR3 formulation comprising 7.25 g of compound (1) to a population of fasted, healthy subjects a pharmacokinetic profile is characterized by a $C_{max}$ ratio from 4.0 to 4.8, and $AUC_{0-inf}$ ratio from 4.8 to 5.6, where the ratio refers to the ratio of the γ-hydroxybutyrate value to the compound (1) value. Following oral administration of an MR3 formulation comprising 7.25 g of compound (1) to a population of fasted, healthy subjects a pharmacokinetic profile is characterized by a $C_{max}$ ratio from 4.2 to 4.6, and $AUC_{0-inf}$ ratio from 5.0 to 5.4, where the ratio refers to the ratio of the γ-hydroxybutyrate value to the compound (1) value.

A pharmaceutical composition can comprise an immediate release component and a modified component.

An immediate release component can comprise any of the immediate release microparticles disclosed herein.

A modified release component can comprise any of the modified microparticles or combinations of modified release microparticles disclosed herein.

A pharmaceutical composition provided by the present disclosure can comprise, for example, from 10 wt % to 50 wt % of compound (1) in an IR component and from 90 wt % to 50 wt % in a MR component, from 20 wt % to 40 wt % of compound (1) in an IR component and from 80 wt % to 60 wt % γ-hydroxybutyrate in an MR component, or from 25 wt % to 35 wt % of compound (1) in an IR component and from 75 wt % to 65 wt % of compound (1) in an MR component, where wt % is based on the total weight of compound (1) in the pharmaceutical composition.

A pharmaceutical composition provided by the present disclosure can comprise, for example, greater than 10 wt % of compound (1) in an IR component and less than 90% of compound (1) in an MR component, greater than 20 wt % of compound (1) in an IR component and less than 80% of compound (1) in an MR components, greater than 30 wt % of compound (1) in an IR component and less than 70% of compound (1) in an MR component, or greater than 40 wt % of compound (1) in an IR component and less than 60% of compound (1) in an MR component, where wt % is based on the total weight of compound (1) in the pharmaceutical composition.

A pharmaceutical composition provided by the present disclosure can have a weight ratio of compound (1) in an IR component to compound (1) in a MR component, for example, from 1:1.5 to 1:3.5, from 1:1.7 to 1:3.3, from 1:1.9 to 1:3.1, from 1:2.1 to 1:2.9, or from 1:2:3 to 1:2.7.

A pharmaceutical composition provided by the present disclosure can have a weight ratio of compound (1) in an IR component to compound (1) in an MR component, for example, greater than 1:1.5, greater than 1:1.7, greater than 1:1.9, greater than 1:2.1, greater than 1:2.3, greater than 1:2.5 or greater than 1:2.7.

A pharmaceutical composition provided by the present disclosure can comprise, for example, from 2.5 g to 7.0 g of compound (1) in an IR component, from 2.75 g to 6.5 g, from 3 g to 6 g, from 3.25 g to 5.75 g, from 3.5 g to 5.5 g, from 3.75 g to 5.25 g or from 4 g to 6 g of compound (1) in an IR component.

A pharmaceutical composition can comprise, for example, from 7 g to 15 g of compound (1) in an MR component, from 7.5 g to 14 g, from 8 g to 13 g, from 8.5 g to 12 g, or from 9 g to 11 g of compound (1) in an MR component.

A pharmaceutical composition can comprise for example, from 2.5 g to 7 g of compound (1) in an IR component and from 7 g to 15 g of compound (1) in an MR component; from 3 g to 6 g of compound (1) in an IR component and from 8 g to 14 g of compound (1) in an MR component; from 3.5 g to 5.5 g of compound (1) in an IR component and from 9 g to 13 g of compound (1) in an MR component; or from 4 g to 5 g of compound (1) in an IR component and from 9 g to 12 g of compound (1) in an MR component.

A pharmaceutical composition provided by the present disclosure can comprise, for example, from 9.5 g to 22 g of compound (1), from 10 g to 20 g of compound (1), from 12 g to 18 g of compound (1), or from 14 g to 16 g of compound (1). A pharmaceutical composition provided by the present disclosure can comprise, for example, greater than 9 g of compound (1), greater than 10 g, greater than 12 g, greater than 14 g, greater than 16 g, greater than 18 g, or greater than 20 g of compound (1).

A pharmaceutical composition provided by the present disclosure can comprise, for example, from 10 wt % to 50 wt % γ-hydroxybutyrate equivalents in an IR component and from 50% to 90 wt % in a MR component, from 20 wt % to 40 wt % γ-hydroxybutyrate equivalents in an IR component and from 60 wt % to 80 wt % γ-hydroxybutyrate in an MR component, or from 25 wt % to 35 wt % γ-hydroxybutyrate equivalents in an IR component and from 65 wt % to 75 wt % γ-hydroxybutyrate equivalents in an MR component, where wt % γ-hydroxybutyrate equivalents is based on the total wt % of γ-hydroxybutyrate equivalents in the pharmaceutical composition.

A pharmaceutical composition provided by the present disclosure can comprise, for example, greater than 10 wt % γ-hydroxybutyrate equivalents in an IR component and less than 90% γ-hydroxybutyrate equivalents in an MR components, greater than 20 wt % γ-hydroxybutyrate equivalents in an IR component and less than 80% γ-hydroxybutyrate equivalents in an MR components, greater than 30 wt % γ-hydroxybutyrate equivalents in an IR component and less than 70% γ-hydroxybutyrate equivalents in an MR components, or greater than 40 wt % γ-hydroxybutyrate in an IR component and less than 60% γ-hydroxybutyrate equivalents in an MR components, where wt % γ-hydroxybutyrate equivalents is based on the total γ-hydroxybutyrate equivalents in the pharmaceutical composition.

A pharmaceutical composition provide by the present disclosure can have a weight ratio of γ-hydroxybutyrate equivalents in an IR component to γ-hydroxybutyrate equivalents in a MR component, for example, from 1.0:1.5 to 1.0:3.5, from 1.0:1.7 to 1.0:3.3, from 1.0:1.9 to 1.0:3.1, from 1.0:2.1 to 1.0:2.9, or from 1.0:2.3 to 1:2.7.

A pharmaceutical composition provided by the present disclosure can have a weight ratio of γ-hydroxybutyrate equivalents in an IR component to γ-hydroxybutyrate equivalents in an MR component, for example, greater than 1.0:1.5, greater than 1.0:1.7, greater than 1.0:1.9, greater than 1.0:2.1, greater than 1.0:2.3, greater than 1.0:2.5 or greater than 1.0:2.7.

A pharmaceutical composition provided by the present disclosure can comprise, for example, from 1 g to 4 g of γ-hydroxybutyrate equivalents in an IR component, from 1.5 g to 3.5 g, from 1.75 g to 3.25 g, or from 2.0 g to 3.0 g, γ-hydroxybutyrate equivalents in an IR component.

A pharmaceutical composition can comprise, for example, from 3 g to 9 g of γ-hydroxybutyrate equivalents in an MR component, from 3.5 g to 8.5 g, from 4 g to 8 g, from 4.5 g to 7.5 g, or from 5 g to 8 g of γ-hydroxybutyrate equivalents in an MR component.

A pharmaceutical composition can comprise for example, from 1 g to 4 g of γ-hydroxybutyrate equivalents in an IR component and from 3 g to 9 g of γ-hydroxybutyrate equivalents in an MR component; from 1.5 g to 3.5 g of γ-hydroxybutyrate equivalents in an IR component and from 3.5 g to 8.5 g of γ-hydroxybutyrate equivalents in an MR component; from 1.75 g to 3.25 g of γ-hydroxybutyrate equivalents in an IR component and from 4.5 g to 7.5 g of γ-hydroxybutyrate equivalents in an MR component; or from 2 g to 3 g of γ-hydroxybutyrate equivalents in an IR component and from 5 g to 8 g of γ-hydroxybutyrate equivalents in an MR component.

A pharmaceutical composition provided by the present disclosure can comprise, for example, from 6.5 g to 18 g γ-hydroxybutyrate equivalents, from 8 g to 16 g γ-hydroxybutyrate equivalents, from 10 g to 14 g of compound (1), or from 11 g to 13 g γ-hydroxybutyrate equivalents. A pharmaceutical composition provided by the present disclosure can comprise, for example, greater than 9 g γ-hydroxybutyrate equivalents, greater than 6.5 g, greater than 8 g, greater than 10 g, greater than 12 g, greater than 14 g, or greater than 16 g γ-hydroxybutyrate equivalents.

Methods for determining the pharmacokinetic profile for γ-hydroxybutyrate and 4-((L-valyl)oxy)butanoic acid (1) following oral administration of 4-((L-valyl)oxy)butanoic acid (1) fasted, healthy subjects is provided in the experimental examples.

Following oral administration of a combined release formulation (CR1) comprising an IR component comprising 4.5 g of compound (1), and an MR1 component comprising 10 g of compound (1) to a population of fasted, healthy subjects, the pharmacokinetic profile of compound (1) can be characterized by a mean $t_{1/2}$ of 0.71 hours, a mean $T_{max}$ of 0.6 hours, a mean $C_{max}$ of 20 μg/mL, a mean $AUC_{0-6}$ of 30 h×μg/mL, a mean $AUC_{0-inf}$ of 31 h×μg/mL, and a mean CL/F of 493 L/h.

Following oral administration of a combined release formulation (CR1) comprising an IR component comprising of 4.5 g of compound (1), and an MR1 component comprising 10 g of compound (1) to a population of fasted, healthy subjects, the pharmacokinetic profile of compound (1) can be characterized by a mean $t_{1/2}$ from 0.6 hours to 0.8 hours, a mean $T_{max}$ from 0.5 hours to 0.7 hours, a mean $C_{max}$ from 10 μg/mL to 30 μg/mL, a mean $AUC_{0-6}$ from 20 h×μg/mL to 40 h×μg/mL, a mean $AUC_{0-inf}$ from 20 h×μg/mL to 40 h×μg/mL, and/or a mean CL/F from 440 L/h to 540 L/h.

Following oral administration of a combined release formulation (CR1) comprising an IR component comprising 4.5 g of compound (1), and an MR1 component comprising 10 g of compound (1) to a population of fasted, healthy subjects, the pharmacokinetic profile of compound (1) can be characterized by a mean $t_{1/2}$ from 0.65 hours to 0.75 hours, a mean $T_{max}$ from 0.55 hours to 0.65 hours, a mean $C_{max}$ from 15 μg/mL to 25 μg/mL, a mean $AUC_{0-6}$ from 25 h×μg/mL to 35 h×μg/mL, a mean $AUC_{0-inf}$ from 25 h×μg/mL to 435 h×μg/mL, and/or a mean CL/F from 470 L/h to 510 L/h.

Following oral administration of a combined release formulation (CR1) comprising an IR component comprising 4.5 g of compound (1), and an MR1 component comprising 10 g of compound (1) to a population of fasted, healthy subjects, the pharmacokinetic profile of γ-hydroxybutyrate can be characterized by a mean $t_{1/2}$ of 0.70 hours, a mean $T_{max}$ of 1.8 hours, a mean $C_{max}$ of 99 μg/mL, a mean $AUC_{0-6}$ of 379 h×μg/mL, a mean $AUC_{0-inf}$ of 407 h×μg/mL, and/or a mean CL/F of 395 L/h.

Following oral administration of a combined release formulation (CR1) comprising an IR component comprising 4.5 g of compound (1), and an MR1 component comprising 10 g of compound (1) to a population of fasted, healthy subjects, the pharmacokinetic profile of γ-hydroxybutyrate can be characterized by a mean $t_{1/2}$ from 0.6 hours to 0.8 hours, a mean $T_{max}$ from 1.6 hours to 2.0 hours, a mean $C_{max}$ from 80 μg/mL to 120 μg/mL, a mean $AUC_{0-6}$ from 340 h×μg/mL to 420 h×μg/mL, a mean $AUC_{0-inf}$ from 360 h×μg/mL to 440 h×μg/mL, and/or a mean CL/F from 360 L/h to 440 L/h.

Following oral administration of a combined release formulation (CR1) comprising an IR component comprising 4.5 g of compound (1), and an MR1 component comprising 10 g of compound (1) to a population of fasted, healthy subjects, the pharmacokinetic profile of γ-hydroxybutyrate can be characterized by a mean $t_{1/2}$ from 0.65 hours to 0.75 hours, a mean $T_{max}$ from 1.7 hours to 1.9 hours, a mean $C_{max}$ from 90 μg/mL to 110 μg/mL, a mean $AUC_{0-6}$ from 360 h×μg/mL to 400 h×μg/mL, a mean $AUC_{0-inf}$ from 380 h×μg/mL to 420 h×μg/mL, and/or a mean CL/F from 380 L/h to 420 L/h.

Following oral administration of a combined release formulation (CR1) comprising an IR component comprising 4.5 g of compound (1), and an MR1 component comprising 10 g of compound (1) to a population of fasted, healthy subjects, the pharmacokinetic profile can be characterized by a $C_{max}$ ratio of 5.3, and an $AUC_{0-inf}$ ratio of 13.3, where the ratio refers to the ratio of the γ-hydroxybutyrate value to the compound (1) value.

Following oral administration of a combined release formulation (CR1) comprising an IR component comprising 4.5 g of compound (1), and an MR1 component comprising 10 g of compound (1) to a population of fasted, healthy subjects, the pharmacokinetic profile can be characterized by a $C_{max}$ ratio from 4.5 to 6.5, and an $AUC_{0-inf}$ ratio from 11.5 to 15.5, where the ratio refers to the ratio of the γ-hydroxybutyrate value to the corresponding compound (1) value.

Following oral administration of a combined release formulation (CR1) comprising an IR component comprising 4.5 g of compound (1), and an MR1 component comprising 10 g of compound (1) to a population of fasted, healthy subjects, the pharmacokinetic profile can be characterized by a $C_{max}$ ratio from 4.7 to 6.3, and an $AUC_{0-inf}$ ratio from 12.5 to 14.5, where the ratio refers to the ratio of the γ-hydroxybutyrate value to the corresponding compound (1) value.

Following oral administration of a combined release formulation (CR2) comprising an IR component comprising 4.5 g of compound (1), and an MR2 component comprising 10 g of compound (1) to a population of fasted, healthy subjects, the pharmacokinetic profile of compound (1) can be characterized by a mean $t_{1/2}$ of 0.89 hours, a mean $T_{max}$ of 0.8 hours, a mean $C_{max}$ of 17 μg/mL, a mean $AUC_{0-6}$ of 26 h×μg/mL, a mean $AUC_{0-inf}$ of 26 h×μg/mL, and/or a mean CL/F of 570 L/h.

Following oral administration of a combined release formulation (CR2) comprising an IR component comprising 4.5 g of compound (1), and an MR2 component comprising 10 g of compound (1) to a population of fasted, healthy subjects, the pharmacokinetic profile of compound (1) can be characterized by a mean $t_{1/2}$ from 0.7 hours to 1.1 hours, a mean $T_{max}$ from 0.7 hours to 0.9 hours, a mean $C_{max}$ from 15 μg/mL to 19 μg/mL, a mean $AUC_{0-6}$ from 22 h×μg/mL to 30 h×μg/mL, a mean $AUC_{0-inf}$ from 22 h×μg/mL to 30 h×μg/mL, and/or a mean CL/F of 530 L/h to 610 L/h.

Following oral administration of a combined release formulation (CR2) comprising an IR component comprising 4.5 g of compound (1), and an MR2 component comprising 10 g of compound (1) to a population of fasted, healthy subjects, the pharmacokinetic profile of compound (1) can be characterized by a mean $t_{1/2}$ from 0.8 hours to 1.0 hours, a mean $T_{max}$ from 0.75 hours to 0.85 hours, a mean $C_{max}$ from 16 μg/mL to 18 μg/mL, a mean $AUC_{0-6}$ from 24 h×μg/mL to 28 h×μg/mL, a mean $AUC_{0-inf}$ from 24 h×μg/mL to 28 h×μg/mL, and/or a mean CL/F of 550 L/h to 590 L/h.

Following oral administration of a combined release formulation (CR2) comprising an IR component comprising 4.5 g of compound (1), and an MR2 component comprising 10 g of compound (1) to a population of fasted, healthy subjects, the pharmacokinetic profile of γ-hydroxybutyrate can be characterized by a mean $t_{1/2}$ of 0.92 hours, a mean $T_{max}$ of 1.3 hours, a mean $C_{max}$ of 75 μg/mL, a mean $AUC_{0-6}$ of 307 h×μg/mL, a mean $AUC_{0-inf}$ of 342 h×μg/mL, and/or a mean CL/F of 525 L/h.

Following oral administration of a combined release formulation (CR2) comprising an IR component comprising 4.5 g of compound (1), and an MR2 component comprising 10 g of compound (1) to a population of fasted, healthy subjects, the pharmacokinetic profile of γ-hydroxybutyrate can be characterized by a mean $t_{1/2}$ from 0.8 hours to 1.0 hours, a mean $T_{max}$ from 1.1 hours to 1.5 hours, a mean $C_{max}$ from 65 μg/mL to 85 μg/mL, a mean $AUC_{0-6}$ from 290 h×μg/mL to 330 h×μg/mL, a mean $AUC_{0-inf}$ from 320 h×μg/mL to 360 h×μg/mL, and/or a mean CL/F from 505 L/h to 545 L/h.

Following oral administration of a combined release formulation (CR2) comprising an IR component comprising 4.5 g of compound (1), and an MR2 component comprising 10 g of compound (1) to a population of fasted, healthy subjects, the pharmacokinetic profile of γ-hydroxybutyrate can be characterized by a mean $t_{1/2}$ from 0.85 hours to 0.95 hours, a mean $T_{max}$ from 1.2 hours to 1.4 hours, a mean $C_{max}$ from 70 μg/mL to 80 μg/mL, a mean $AUC_{0-6}$ from 300 h×μg/mL to 320 h×μg/mL, a mean $AUC_{0-inf}$ from 330 h×μg/mL to 350 h×μg/mL, and/or a mean CL/F from 515 L/h to 535 L/h.

Following oral administration of a combined release formulation (CR2) comprising an IR component comprising 4.5 g of compound (1), and an MR2 component comprising 10 g of compound (1) to a population of fasted, healthy subjects, the pharmacokinetic profile can be characterized by a $C_{max}$ ratio of 4.9, and an $AUC_{0-inf}$ ratio of 12.7, where the ratio refers to the ratio of the γ-hydroxybutyrate value to the compound (1) value.

Following oral administration of a combined release formulation (CR2) comprising an IR component comprising 4.5 g of compound (1), and an MR2 component comprising 10 g of compound (1) to a population of fasted, healthy subjects, the pharmacokinetic profile can be characterized by a $C_{max}$ ratio from 4.7 to 5.1, and an $AUC_{0-inf}$ ratio from 11 to 15, where the ratio refers to the ratio of the γ-hydroxybutyrate value to the corresponding compound (1) value.

Following oral administration of a combined release formulation (CR2) comprising an IR component comprising 4.5 g of compound (1), and an MR2 component comprising 10 g of compound (1) to a population of fasted, healthy subjects, the pharmacokinetic profile can be characterized by a $C_{max}$ ratio from 4.8 to 5.0, and an $AUC_{0-inf}$ ratio from 12 to 14, where the ratio refers to the ratio of the γ-hydroxybutyrate value to the corresponding compound (1) value.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile of compound (1) can be characterized by a mean $t_{1/2}$ of 1.1 hours, a mean $T_{max}$ of 1.0 hours, a mean $C_{max}$ of 19 μg/mL, a mean $AUC_{0-6}$ of 32 h×μg/mL, a mean $AUC_{0-inf}$ of 34 h×μg/mL, and/or a mean CL/F of 569 L/h.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile of compound (1) can be characterized by a mean $t_{1/2}$ from 1.0 hours to 1.2 hours, a mean $T_{max}$ from 0.9 hours to 1.1 hours, a mean $C_{max}$ from 15 μg/mL to 23 μg/mL, a mean $AUC_{0-6}$ from 28 h×μg/mL to 36 h×μg/mL, a mean $AUC_{0-inf}$ from 30 to 38 h×μg/mL, and/or a mean CL/F from 550 L/h to 590 L/h.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile of compound (1) can be characterized by a mean $t_{1/2}$ from 1.05 hours to 1.15 hours, a mean $T_{max}$ from 0.95 hours to 1.05 hours, a mean $C_{max}$ from 17 μg/mL to 21 μg/mL, a mean $AUC_{0-6}$ from 30 h×μg/mL to 32 h×μg/mL, a mean $AUC_{0-inf}$ from 32 h×μg/mL to 36 h×μg/mL, and/or a mean CL/F from 560 L/h to 580 L/h.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile of γ-hydroxybutyrate can be characterized by a mean $t_{1/2}$ of 0.97 hours, a mean $T_{max}$ of 1.7 hours, a mean $C_{max}$ of 96 μg/mL, a mean $AUC_{0-6}$ of 334 h×μg/mL, a mean $AUC_{0-inf}$ of 389 h×μg/mL, and/or a mean CL/F of 55 L/h.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile of γ-hydroxybutyrate can be characterized by a mean $t_{1/2}$ from 0.9 hours to 1.1 hours, a mean $T_{max}$ from 1.5 hours to 1.9 hours, a mean $C_{max}$ from 85 μg/mL to 105 μg/mL, a mean $AUC_{0-6}$ from 314 h×μg/mL to 354 h×μg/mL, a mean $AUC_{0-inf}$ from 370 h×μg/mL to 410 h×μg/mL, and/or a mean CL/F from 45 L/h to 65 L/h.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile of γ-hydroxybutyrate can be characterized by a mean $t_{1/2}$ from 0.95 hours to 1.05 hours, a mean $T_{max}$ from 1.6 hours to 1.8 hours, a mean $C_{max}$ from 90 μg/mL to 100 μg/mL, a mean $AUC_{0-6}$ from 324 h×μg/mL to 344 h×μg/mL, a mean $AUC_{0-inf}$ from 380 h×μg/mL to 400 h×μg/mL, and/or a mean CL/F from 50 L/h to 60 L/h.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile can be characterized by a $C_{max}$ ratio of 5.3, and an $AUC_{0-inf}$ ratio of 11.6, where the ratio refers to the ratio of the γ-hydroxybutyrate value to the compound (1) value.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile can be characterized by a $C_{max}$ ratio from 5.0 to 5.6, and an $AUC_{0-inf}$ ratio from 10 to 14, where the ratio refers to the ratio of the γ-hydroxybutyrate value to the corresponding compound (1) value.

Following oral administration of a combined release formulation (CR3) comprising an IR component comprising 4.5 g of compound (1), and an MR1 component comprising 13.5 g of compound (1) to a population of fasted, healthy subjects, the pharmacokinetic profile can be characterized by a $C_{max}$ ratio from 5.1 to 5.5, and an $AUC_{0-inf}$ ratio from 11 to 13, where the ratio refers to the ratio of the γ-hydroxybutyrate value to the corresponding compound (1) value.

Following oral administration of a combined release formulation (CR4) comprising an IR component comprising 6 g of compound (1), and an MR2 component comprising 12 g of compound (1) to a population of fasted, healthy subjects, the pharmacokinetic profile of compound (1) can be characterized by a mean $t_{1/2}$ of 1.1 hours, a mean $T_{max}$ of 1.0 hours, a mean $C_{max}$ of 19 µg/mL, a mean $AUC_{0-6}$ of 31 h×µg/mL, a mean $AUC_{0-inf}$ of 34 h×µg/mL, and/or a mean CL/F of 554 L/h.

Following oral administration of a combined release formulation (CR4) comprising an IR component comprising 6 g of compound (1), and an MR2 component comprising 12 g of compound (1) to a population of fasted, healthy subjects, the pharmacokinetic profile of compound (1) can be characterized by a mean $t_{1/2}$ from 1.0 hours to 1.2 hours, a mean $T_{max}$ from 1.0 hours to 1.2 hours, a mean $C_{max}$ from 17 µg/mL to 21 µg/mL, a mean $AUC_{0-6}$ from 29 h×µg/mL to 33 h×µg/mL, a mean $AUC_{0-inf}$ from 32 h×µg/mL to 36 h×µg/mL, and/or a mean CL/F from 535 L/h to 575 L/h.

Following oral administration of a combined release formulation (CR4) comprising an IR component comprising 6 g of compound (1), and an MR2 component comprising 12 g of compound (1) to a population of fasted, healthy subjects, the pharmacokinetic profile of compound (1) can be characterized by a mean $t_{1/2}$ from 1.05 hours to 1.15 hours, a mean $T_{max}$ from 1.05 hours to 1.15 hours, a mean $C_{max}$ from 18 µg/mL to 20 µg/mL, a mean $AUC_{0-6}$ from 30 h×µg/mL to 32 h×µg/mL, a mean $AUC_{0-inf}$ from 33 h×µg/mL to 35 h×µg/mL, and/or a mean CL/F from 545 L/h to 565 L/h.

Following oral administration of a combined release formulation (CR4) comprising an IR component comprising 6 g of compound (1), and an MR2 component comprising 12 g of compound (1) to a population of fasted, healthy subjects, the pharmacokinetic profile of γ-hydroxybutyrate can be characterized by a mean $t_{1/2}$ of 0.9 hours, a mean $T_{max}$ of 2.2 hours, a mean $C_{max}$ of 92 µg/mL, a mean $AUC_{0-6}$ of 332 h×µg/mL, a mean $AUC_{0-inf}$ of 404 h×µg/mL, and/or a mean CL/F of 55.4 L/h.

Following oral administration of a combined release formulation (CR4) comprising an IR component comprising 6 g of compound (1), and an MR2 component comprising 12 g of compound (1) to a population of fasted, healthy subjects, the pharmacokinetic profile of γ-hydroxybutyrate can be characterized by a mean $t_{1/2}$ from 0.8 hours to 1.0 hours, a mean $T_{max}$ from 2.0 hours to 2.4 hours, a mean $C_{max}$ from 88 µg/mL to 96 µg/mL, a mean $AUC_{0-6}$ from 310 h×µg/mL to 350 h×µg/mL, a mean $AUC_{0-inf}$ h×µg/mL from 380 h×µg/mL to 420 h×µg/mL, and/or a mean CL/F from 51 L/h to 59 L/h.

Following oral administration of a combined release formulation (CR4) comprising an IR component comprising 6 g of compound (1), and an MR2 component comprising 12 g of compound (1) to a population of fasted, healthy subjects, the pharmacokinetic profile of γ-hydroxybutyrate can be characterized by a mean $t_{1/2}$ from 0.85 hours to 0.95 hours, a mean $T_{max}$ from 2.1 hours to 2.3 hours, a mean $C_{max}$ from 90 µg/mL to 94 µg/mL, a mean $AUC_{0-6}$ from 320 h×µg/mL to 340 h×µg/mL, a mean $AUC_{0-inf}$ h×µg/mL from 390 h×µg/mL to 410 h×µg/mL, and/or a mean CL/F from 53 L/h to 57 L/h.

Following oral administration of a combined release formulation (CR4) comprising an IR component comprising 6 g of compound (1), and an MR2 component comprising 12 g of compound (1) to a population of fasted, healthy subjects, the pharmacokinetic profile can be characterized by a $C_{max}$ ratio of 6.0, and an $AUC_{0-inf}$ ratio of 12.0, where the ratio refers to the ratio of the γ-hydroxybutyrate value to the compound (1) value.

Following oral administration of a combined release formulation (CR4) comprising an IR component comprising 6 g of compound (1), and an MR2 component comprising 12 g of compound (1) to a population of fasted, healthy subjects, the pharmacokinetic profile can be characterized by a $C_{max}$ ratio from 4 to 8, and an $AUC_{0-inf}$ ratio from 10 to 14, where the ratio refers to the ratio of the γ-hydroxybutyrate value to the corresponding compound (1) value.

Following oral administration of a combined release formulation (CR4) comprising an IR component comprising 6 g of compound (1), and an MR2 component comprising 12 g of compound (1) to a population of fasted, healthy subjects, the pharmacokinetic profile can be characterized by a $C_{max}$ ratio from 5 to 7, and an $AUC_{0-inf}$ ratio from 11 to 13, where the ratio refers to the ratio of the γ-hydroxybutyrate value to the corresponding compound (1) value.

For a combined release formulation provided by the present disclosure at 6 hours following oral administration of the combined release formulation comprising from 10 g to 20 g of compound (1) to a population of fasted, healthy subjects, the concentration of γ-hydroxybutyrate in the plasma of the subjects can be less than 15 µg/mL, less than 10 µg/mL, or less than 5 µg/mL.

For a combined release formulation provided by the present disclosure following oral administration of the combined release formulation comprising from 10 g to 20 g of compound (1) to a population of fasted, healthy subjects, the γ-hydroxybutyrate concentration in the plasma of the subjects can be greater than the sum of: (a) the $AUC_{inf}$ of γ-hydroxybutyrate following oral administration of the immediate release component; and (b) the $AUC_{inf}$ of γ-hydroxybutyrate following oral administration of the modified release component to the population of fasted, healthy subjects.

For a combined release formulation provided by the present disclosure between 6 hours and 8 hours following oral administration of the combined release formulation comprising from 10 g to 20 g of compound (1) to a population of fasted, healthy subjects, the γ-hydroxybutyrate concentration in the plasma of the subjects can be greater than the sum of: (a) the γ-hydroxybutyrate concentration between 6 hours and 8 hours following oral administration of the immediate release component; and (b) the γ-hydroxybutyrate concentration between 6 hours and 8 hours following oral administration of the modified release component to the population of fasted, healthy subjects.

For a combined release formulation provided by the present disclosure following oral administration of the combined release formulation comprising from 10 g to 20 g of compound (1) to a population of healthy, fasted subjects, concentration from 6 hours to 8 hours following oral administration can be greater than the concentration of γ-hydroxybutyrate in the plasma of the subjects following administration of the modified release component alone.

For a combined release formulation provided by the present disclosure the mean γ-hydroxybutyrate $AUC_{0-inf}$ following oral administration of the immediate release component and the modified release component to a population of fasted, healthy subjects can be greater than the sum of the mean γ-hydroxybutyrate $AUC_{0-inf}$ following oral administration of the immediate release component alone, and the mean γ-hydroxybutyrate $AUC_{0-inf}$ following oral administration of the modified release component alone.

For a combined release formulation provided by the present disclosure the mean compound (1) $AUC_{0-inf}$ following oral administration of the immediate release component and the modified release component to a population of subjects is substantially the same as the sum of the mean compound (1) $AUC_{0-inf}$ following oral administration of the immediate release component alone, and the mean compound (1) $AUC_{0-inf}$ following oral administration of the modified release component alone.

For a combined release formulation provided by the present disclosure the mean γ-hydroxybutyrate $AUC_{0-inf}$ following oral administration of a combined release formulation comprising an immediate release component comprising 4.52 gm compound (1) and a modified release component comprising 10 gm compound (1) to a population of fasted, healthy subjects is greater than the sum of the mean γ-hydroxybutyrate $AUC_{0-inf}$ following oral administration of an immediate release component comprising 7.25 gm compound (1) alone, and the mean γ-hydroxybutyrate $AUC_{0-inf}$ following oral administration of a modified release component comprising 7.25 g of compound (1) alone.

For a combined release formulation provided by the present disclosure the mean compound (1) $AUC_{0-inf}$ following oral administration of the combined release formulation comprising an immediate release component comprising 4.52 gm compound (1) and a modified release component comprising 10 gm compound (1) to a population of fasted, healthy subjects is substantially the same as the sum of the mean compound (1) $AUC_{0-inf}$ following oral administration of an immediate release component comprising 7.25 gm compound (1) alone, and the mean compound (1) $AUC_{0-inf}$ following oral administration of a modified release component comprising 7.25 g of compound (1) alone.

A combined release formulation provided by the present disclosure can comprise an immediate release component and a modified release component.

An immediate release component can comprise an uncoated microparticles comprising a compound (1) or seal-coated microparticles comprising a compound (1).

An immediate release component can comprise a solution comprising compound (1).

A modified release component can comprise uncoated or seal-coated microparticles comprising a compound (1) with a modified release coating covering the microparticles. The modified release microparticles can comprise, for example, from 5% wg to 50% wg of a modified release coating.

A combined release formulation provided by the present disclosure can comprise, for example, greater than 5 gm of a compound (1), greater than 8 g, greater than 12 g, greater than 16 g, or greater than 20 g of a compound (1). A combined release formulation provided by the present disclosure can comprise, for example, from 5 g to 20 g of a compound (1), from 7 g to 18 g, from 9 g to 16 g, or from 11 g to 16 g of a compound (1).

In a combined release formulation provided by the present disclosure, the immediate release component can comprise from 2.5 g to 6.5 g such as from 3.5 g to 5.5 g of a compound (1), and the modified release component can comprise from 12.5 g to 16.5 g such as from 12.5 g to 15.5 g of a compound (1).

In a combined release formulation provided by the present disclosure a weight ratio of the compound (1) in the immediate release component to the compound in the modified release component can be, for example, from 0.3 to 0.6, from 0.35 to 0.55, or from 0.40 to 0.50.

In a combined release formulation provided by the present disclosure from 15 wt % to 45 wt % of the compound (1) can be in the immediate release compound, from 20 wt % to 40 wt %, or from 25 wt % to 35 wt %, where wt % is based on the total weight of the compound (1) in the combined release formulation.

Following oral administration of a combined release formulation provided by the present disclosure comprising from 7 g γ-hydroxybutyrate equivalents to 11 g γ-hydroxybutyrate equivalents (11.3 g to 17.7 g of a compound (1)) to a population of fasted patients the plasma γ-hydroxybutyrate pharmacokinetic profile is characterized by a mean $T_{max}$ of less than 2.4 hours, less than 2.2 hours, less than 2.0 hours, less than 1.8 hours, less than 1.6 hours.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $T_{max}$ from 1.4 hours to 2.4 hours, from 1.5 hours to 2.2 hours, from 1.6 hours to 2.0 hours, or from 1.7 hours to 1.9 hours.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_{max}$ of less than 100 μg/mL, less than 95 μg/mL, less than 90 μg/mL, less than 85 μg/mL, or less than 80 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_{max}$ from 75 μg/mL to 105 μg/mL, from 80 μg/mL to 100 μg/mL, or from 85 μg/mL to 95 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $AUC_{0-6h}$ of greater than 250 h×μg/mL, greater than 275 h×μg/mL, greater than 300 h×μg/mL, greater than 325 h×μg/mL, greater than 350 h×μg/mL, greater than 400 h×μg/mL, or greater than 425 h×μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $AUC_{0-6h}$ of from 250 h×μg/mL to 425 h×μg/mL, from 275 h×μg/mL to 400 h×μg/mL, from 300 h×μg/mL to 375 h×μg/mL, or from 325 h×μg/mL to 375 h×μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_6$ of less than 36 μg/mL, less than 34 μg/mL, less than 32 μg/mL, less than 30, less than 28 μg/mL, less than 26 μg/mL, less than 24 μg/mL, less than 22 μg/mL, less than 20 μg/mL, or less than 18 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_6$ of from 18 μg/mL to 36 μg/mL, from 20 μg/mL to 34 μg/mL, from 22 μg/mL to 32 μg/mL, or from 24 μg/mL to 30 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_8$ of less than 20 μg/mL, less than 16 μg/mL, less than 12 μg/mL, less than 10 μg/mL, less than 8 μg/mL, or less than 4 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_8$ of from 4 μg/mL to 20 μg/mL, from 6 μg/mL to 18 μg/mL, from 8 μg/mL to 16 μg/mL, or from 10 μg/mL to 14 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_{10h}$ of less than 10 μg/mL, less than 8 μg/mL, less than 6 μg/mL, less than 4 μg/mL, or less than 2 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a mean $C_{10h}$ of from 0 μg/mL to 8 μg/mL, from 0 μg/mL to 6 μg/mL, from 0 μg/mL to 4 μg/mL, or from 0 μg/mL to 2 μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a plasma γ-hydroxybutyrate concentration greater than 10 μg/mL, greater than 15 μg/mL, greater than 20 μg/mL, greater than 25 μg/mL, or greater than 30 μg/mL for from 5 hours to 7 hours, such as 6 hours.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a plasma γ-hydroxybutyrate concentration from 10 μg/mL to 30 μg/mL, from 15 μg/mL to 30 μg/mL, from 20 μg/mL to 30 μg/mL, from 22 μg/mL to 28 μg/mL, or from 24 μg/mL to 26 μg/mL, for from 5 hours to 7 hours, such as 6 hours.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a $C_{max}/C_{5h}$ ratio of less than 4, less than 3, or less than 2.

Following oral administration of a combined release formulation provided by the present disclosure to a population of fasted patients the plasma γ-hydroxybutyrate pharmacokinetic profile is characterized by a $C_{max}/C_{5h}$ ratio of from 1.5 to 4, from 1.5 to 3.5, or from 2 to 3.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a $C_{max}/C_{5h}$ ratio of greater than 2, greater than 4, greater than 6, greater than 8, or greater than 10.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a $C_{max}/C_{5h}$ ratio of from 2 to 10, from 2 to 8, or from 4 to 6.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a $C_{max}/C_{5h}$ ratio of greater than 5, greater than 10, greater than 15, or greater than 20.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a $C_{max}/C_{5h}$ ratio of from 5 to 20 or from 10 to 15.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a $AUC_{0-8h}/AUC_{inf}$ ratio of greater than 0.6, greater than 0.8, greater than 1.0, or greater than 1.2.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by a $AUC_{0-8h}/AUC_{inf}$ ratio of from 0.6 to 1.2 or from 0.8 to 1.0.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by an $AUC_{inf}$ of greater than 250 h×μg/mL, greater than 300 h×μg/mL greater than 350 h×μg/mL, or greater than 400 h×μg/mL.

Following oral administration of a combined release formulation provided by the present disclosure comprising from 7 g γ-hydroxybutyrate equivalents to 11 g γ-hydroxybutyrate equivalents to a population of fasted patients the plasma γ-hydroxybutyrate pharmacokinetic profile is characterized by an $AUC_{0-8h}/AUC_{inf}$ from 250 h×μg/mL to 450 h×μg/mL, or from 300 h×μg/mL to 400 h×μg/mL.

In any of the foregoing combined release formulations, the combined release formulations can comprise 14.5 g of compound (1) corresponding to 9 g γ-hydroxybutyrate equivalents, with 4.5 g of compound (1) in the immediate release component and 10 g compound (1) in the modified release component.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $T_{max}$ from 2.0 hours to 3.2 hours such as from 2.2 hours to 3.0 hours or from 2.4 hours to 2.8 hours.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean CMX from 94 μg/mL to 114 μg/mL such as from 96 μg/mL to 112 μg/mL, from 98 μg/mL to 110 μg/mL, from 100 μg/mL to 108 μg/mL or from 102 μg/mL to 106 μg/mL.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $AUC_{inf}$ from 430 hr×μg/mL to 490 hr×μg/mL, from 440 hr×μg/mL to 480 hr×μg/mL, or from 450 hr×μg/mL to 470 hr×μg/mL.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $AUC_{0-6}$ from 360 hr×μg/mL to 420 hr×μg/mL, from 370 hr×μg/mL to 410 hr×μg/mL, or from 380 hr×μg/mL to 400 hr×μg/mL.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $C_6$ from 25 μg/mL to 55 μg/mL, from 30 μg/mL to 50 μg/mL, or from 35 μg/mL to 45 μg/mL.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $C_8$ from 5 μg/mL to 15 μg/mL, from 7 μg/mL to 13 μg/mL, or from 9 μg/mL to 11 μg/mL.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $C_{10}$ less than 5 μg/mL such as less than 4 μg/mL, or less than 2 μg/mL.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $C_{max}/C_8$ ratio from 9 to 11 such as from 9.5 to 10.5.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by a mean $T_{max}$ from 2.0 hours to 3.2 hours, a mean $C_{max}$ from 94 μg/mL to 114 μg/mL, a mean $AUC_{inf}$ from 430 hr×μg/mL to 490 hr×μg/mL, a mean $AUC_{0-6}$ from 360 hr×μg/mL to 420 hr×μg/mL, a mean $C_6$ from 25 μg/mL to 55 μg/mL, a mean $C_8$ from 5 μg/mL to 15 μg/mL, a mean $C_{10}$ less than 5 μg/mL, and/or a mean $C_{max}/C_8$ ratio from 9 to 11.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by plasma γ-hydroxybutyrate greater than 25 μg/mL for at least 8 hours, at least 7 hours, at least 6 hours, at least 5 hours, or at least 4 hours.

Following oral administration of a combined release formulation comprising 4.5 g of compound (1) in an IR component and 10 g of compound (1) in an MR component to a population of fasted, healthy subjects a pharmacokinetic profile of γ-hydroxybutyrate can be characterized by plasma γ-hydroxybutyrate for from 2 hours to 8 hours, from 2 hours to 7 hours, from 2 hours to 6 hours, from 2 hours to 5 hours, from 2 hours to 4 hours, from 4 hours to 6 hours or from 5 hours to 6 hours.

Figure 2A:
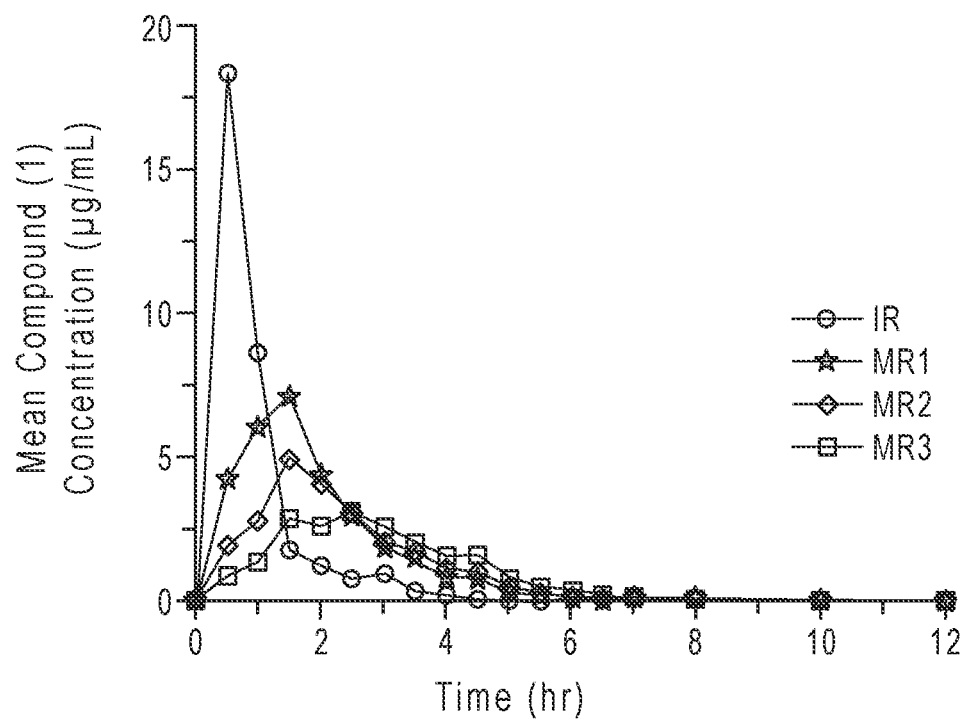
FIG. 2A shows the mean plasma concentration of 4-((L-valyl)oxy)butanoic acid (compound (1)) following oral administration of an immediate release component and three modified release components of compound (1) to fasted, healthy subjects.
Figure 2B:
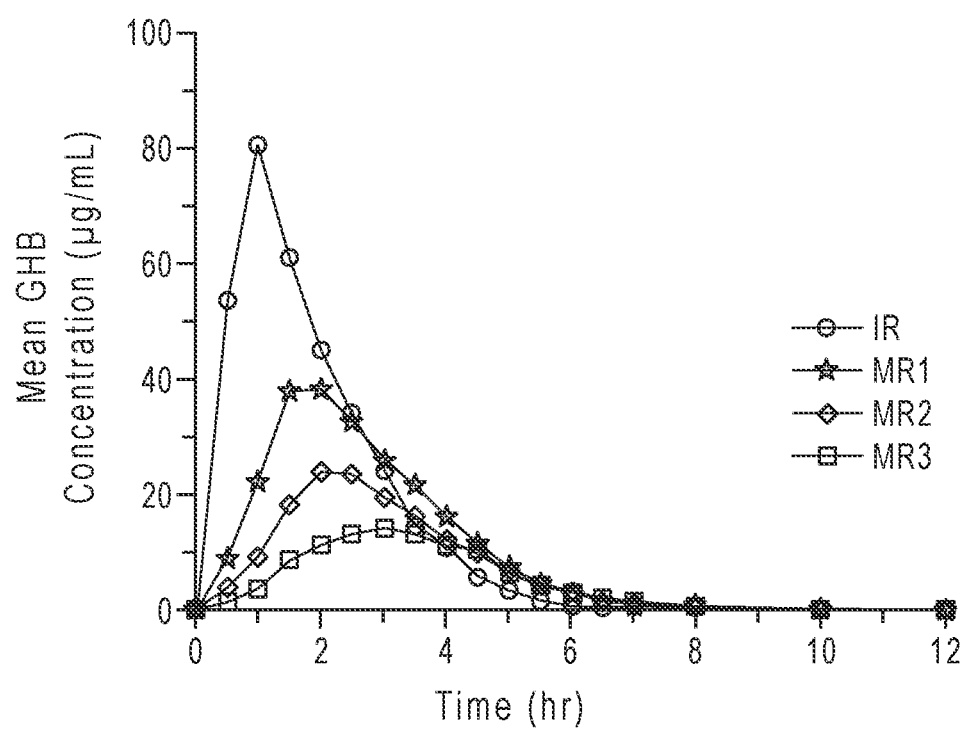
FIG. 2B shows the mean plasma γ-hydroxybutyrate concentration following oral administration of an immediate release component and three modified release formulations of compound (1) to fasted, healthy subjects.

An immediate release component provided by the present disclosure can exhibit a pharmacokinetic profile that is bioequivalent to a pharmacokinetic profile for compound (1) as shown in FIG. 2A or for γ-hydroxybutyrate as shown in FIG. 2B.

A modified release component provided by the present disclosure can exhibit a pharmacokinetic profile that is bioequivalent to the pharmacokinetic profile for compound (1) as shown FIG. 2A or for γ-hydroxybutyrate as shown in FIG. 2B.

Figure 5:
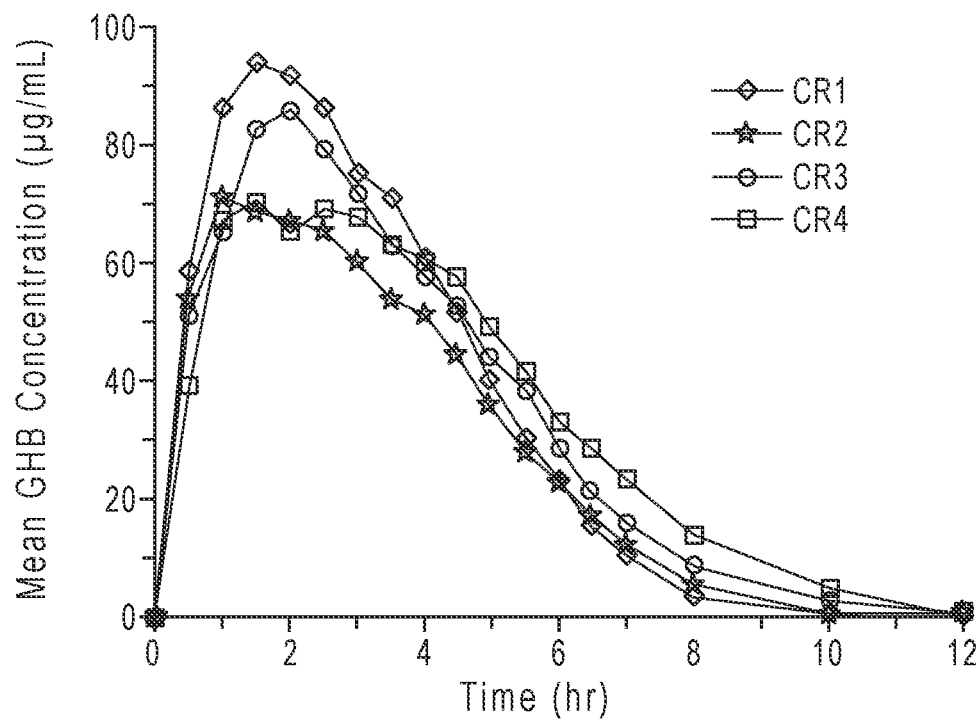
FIG. 5 shows the mean γ-hydroxybutyrate plasma concentration following oral administration of combined release formulations of compound (1) to fasted, healthy subjects.

A combined release formulation provided by the present disclosure can exhibit a pharmacokinetic profile that is bioequivalent to the pharmacokinetic profile for γ-hydroxybutyrate as shown in FIG. 5.

Figure 6:
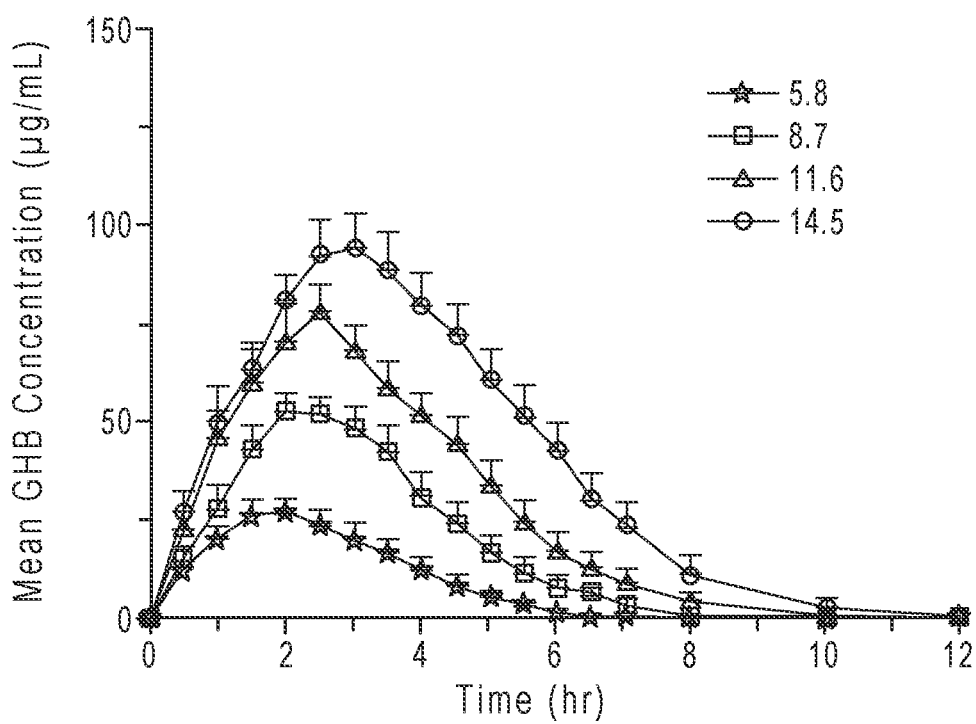
FIG. 6 shows the mean γ-hydroxybutyrate plasma concentration following oral administration of different doses of a combined release formulation provided by the present disclosure as described in Example 5 to fasted, healthy subjects.

A combined release formulation provided by the present disclosure can exhibit a pharmacokinetic profile that is bioequivalent to the pharmacokinetic profile for γ-hydroxybutyrate as shown in FIG. 6.

A combined release formulation provided by the present disclosure can exhibit a pharmacokinetic profile that is bioequivalent to the pharmacokinetic profile for γ-hydroxybutyrate as provided in FIG. 4.

A pharmaceutical composition provided by the present disclosure, such as a combined release formulation, can exhibit a pharmacokinetic profile that is bioequivalent to the pharmacokinetic profile for compound (1) provided in Table 6 or for γ-hydroxybutyrate as shown in Table 7. Table 6 shows the mean plasma γ-hydroxybutyrate concentration of compound (1) following oral administration of various combined release (CR) formulations as described in Example 4. Table 7 shows the mean plasma concentration of γ-hydroxybutyrate following oral administration of various combined release (CR) formulations as described in Example 4.

A pharmaceutical composition provided by the present disclosure, such as a combined release formulation, can exhibit a pharmacokinetic profile that is bioequivalent to the pharmacokinetic profile for compound (1) provided in FIG. 3 or for γ-hydroxybutyrate as shown in FIG. 4. FIG. 3 shows the mean plasma γ-hydroxybutyrate concentration of compound (1) following oral administration of various combined release (CR) formulations as described in Example 4. FIG. 4 shows the mean plasma concentration of γ-hydroxybutyrate following oral administration of various combined release (CR) formulations as described in Example 4.

A pharmaceutical composition provided by the present disclosure, such as a combined release formulation, can exhibit a pharmacokinetic profile that is bioequivalent to the pharmacokinetic profile for γ-hydroxybutyrate as shown in FIG. 6 or as summarized in Table 10.

A dose of a pharmaceutical composition provided by the present disclosure can be any suitable to dose for treating a disease or symptom of a disease in a patient.

A dose of a pharmaceutical composition provided by the present disclosure can comprise, for example, from 6 g to 22 g of compound (1), from 8 g to 20 g, from 10 g to 20 g, from 12 g to 20 g, from 14 g to 20 g, or from 14 g to 18 g of compound (1).

A dose of a pharmaceutical composition provided by the present disclosure can comprise, for example, greater than 6 g of compound (1), greater than 8 g, greater than 10 g, greater than 12 g, greater than 14, g, greater than 18 g, or greater than 20 g of compound (1).

A dose of a pharmaceutical composition provided by the present disclosure can comprise, for example, from 3 g to 12 g γ-hydroxybutyrate equivalents, from 4 g to 11 g, from 5 g to 10 g, or from 6 g to 9 g γ-hydroxybutyrate equivalents.

A dose of a pharmaceutical composition provided by the present disclosure can comprise, for example, greater than 3 g γ-hydroxybutyrate equivalents, greater than 5 g, greater than 7 g, greater than 9 g, or greater than 9 g γ-hydroxybutyrate equivalents.

A pharmaceutical composition provided by the present disclosure can be included in a kit that may be used to administer the compound to a patient for therapeutic purposes. A kit can include a pharmaceutical composition comprising an immediate release component and a modified release component suitable for administration to a patient and instructions for administering the pharmaceutical composition to the patient. The kit can be used, for example, to treat a sleep disorder. A kit can comprise an immediate release component and a modified release component, a pharmaceutically acceptable vehicle for administering the immediate release component and a modified release component, and instructions for administering the pharmaceutical composition to a patient.

The pharmaceutical compositions can be included in a container, pack, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

A pharmaceutical composition provided by the present disclosure can be used, for example, to treat narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, and fibromyalgia.

A pharmaceutical composition provided by the present disclosure can be used, for example, to treat to treat REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, and anxiety.

A pharmaceutical composition provided by the present disclosure can be used, for example, to enhance cognitive function in a neurodegenerative disorder. For example, a pharmaceutical composition provided by the present disclosure can be used to enhanced cognitive function in a patient with Parkinson's disease or in a patient with Alzheimer's disease.

A pharmaceutical composition provided by the present disclosure can be used to treat narcolepsy such as Type 1 or Type 2 narcolepsy. The treatment of narcolepsy is defined as reducing excessive daytime sleepiness or reducing the frequency of cataplectic attacks. In various embodiments, the composition is sufficient to be administered once daily. For example, the composition may be sufficient to administer in the morning or at night less than 2 hours after eating a meal. The formulation is also effective to induce sleep for at least 6 to 8 consecutive hours. In one embodiment, the composition administered less than two hours after eating is effective to induce sleep for at least 8 consecutive hours. In various embodiments, the formulation is effective to induce sleep for at least 6 hours, at least 7 hours, at least 8 hours, at least 9 hours, or at least 10 hours. In other embodiments, the formulation is effective to induce sleep for up to 6 hours, up to 7 hours, up to 8 hours, up to 9 hours, or up to 10 hours.

A pharmaceutical composition and formulation provided by the present disclosure can be used to treat a sleeping disorder, drug abuse, alcohol and opiate withdrawal, a reduced level of growth hormone, anxiety, analgesia, a symptom associated with a neurological disorder such as Parkinson's disease, Alzheimer's disease and depression, an endocrine disturbance, hypoxia or anoxia of tissues such as from stroke or myocardial infarction, or an increased level of intracranial pressure.

A pharmaceutical composition provided by the present disclosure can be used to treat a disease or condition capable of being treated by administering γ-hydroxybutyric acid such as, for example, fibromyalgia and sleep disorders such as apnea, sleep time disturbances, narcolepsy, cataplexy, excessive daytime sleepiness (EDS), sleep paralysis, hypnagogic hallucination, sleep arousal, insomnia, and nocturnal myoclonus.

A pharmaceutical composition provided by the present disclosure can be used to treat a sleep disorder associated with a viral disease such as a COVID-19 infection.

A pharmaceutical composition provided by the present disclosure can be used for relieving pain and improving function in patients with fibromyalgia syndrome, and in alleviating excessive daytime sleepiness and fatigue in patients with Parkinson's disease, improving myoclonus and essential tremor, and reducing tardive dyskinesia and bipolar disorder.

A pharmaceutical composition provided by the present disclosure can be used to improve cognitive function in a patient with a neurological disorder such as Parkinson's disease and Alzheimer's disease.

A pharmaceutical composition and formulation provide by the present disclosure can be used to treat a neurodegenerative disease or a condition or disorder associated with a neurovegetative disease in a patient where the neurodegenerative diseases is selected from, for example, Alzheimer's diseases, amyotrophic lateral sclerosis, Friedrich's ataxia, Huntington's diseases, Lewy body disease, Parkinson's disease, spinal muscular atrophy, motor neuron disease, Creutzfeldt Jakob disease, primary progressive aphasia, and progressive supranuclear palsy.

Other examples of neurodegenerative diseases include Alper's diseases, Batten disease, cerebro-oculo-facio-skeletal syndrome, corticobasal degeneration, Gerstmann-Straussler-Scheinker disease, kuru, Leigh's disease, monometic amyotrophy, multiple system atrophy, opsoclonus myoclonus, prion diseases, progressive multifocal leukoencephalopathy, leukoencephalopathy striatonigral degermation, and transmissible spongiform encephalopathies.

ASPECTS

The invention can be defined by one or more of the following aspects.

Aspect 1. A pharmaceutical composition comprising;
an immediate release (IR) component, wherein the immediate release component comprises from 1.2 g γ-hydroxybutyrate-equivalents to 4.0 g γ-hydroxybutyrate-equivalents; and
a modified release (MR) component, wherein the modified release component comprises from 3 g γ-hydroxybutyrate-equivalents to 9 g γ-hydroxybutyrate-equivalents.

Aspect 2. The pharmaceutical composition of aspect 1, wherein each of the immediate release component and the modified release component comprise 4-((L-valyl)oxy)butanoic acid.

Aspect 3. The pharmaceutical composition of any one of aspects 1 to 2, wherein the γ-hydroxybutyrate equivalents is in the form of γ-((L-valyl)oxy)butanoic acid.

Aspect 4. The pharmaceutical composition of any one of aspects 2 to 3, wherein,
the immediate release component comprises from 10 wt % to 50 wt % of 4-((L-valyl)oxy)butanoic acid; and
the modified release component comprises from 50 wt % to 90 wt % of 4-((L-valyl)oxy)butanoic acid,
wherein wt % is based on the total weight of compound (1) in the pharmaceutical composition.

Aspect 5. The pharmaceutical composition of any one of aspects 2 to 4, wherein,
the immediate release component comprises from 2 g to 7 g of 4-((L-valyl)oxy)butanoic acid; and
the modified release component comprises from 7 g to 15 g of 4-((L-valyl)oxy)butanoic acid.

Aspect 6. The pharmaceutical composition of any one of aspects 1 to 5, wherein,
the immediate release component comprises from 1 g to 4 g of γ-hydroxybutyrate equivalents; and
the modified release component comprises from 3.5 g to 8.5 g of γ-hydroxybutyrate equivalents.

Aspect 7. The pharmaceutical composition of any one of aspects 1 to 6, wherein a weight ratio of the gm-equivalents γ-hydroxybutyrate in the immediate release component to the gm-equivalents γ-hydroxybutyrate in the modified release component is from 1.5 to 3.5.

Aspect 8. The pharmaceutical composition of any one of aspects 1 to 7, wherein the immediate release component comprises a plurality of immediate release microparticles.

Aspect 9. The pharmaceutical composition of aspect 8, wherein the immediate release microparticles comprise greater than 90 wt % of 4-((L-valyl)oxy)butanoic acid, wherein wt % is based on the total weight of the immediate release microparticles.

Aspect 10. The pharmaceutical composition of any one of aspects 8 to 9, wherein the immediate release microparticles have a volume mean diameter D(4,3) from 200 μm to 500 μm.

Aspect 11. The pharmaceutical composition of any one of aspects 1 to 10, wherein the immediate release component comprises a solution suitable for oral administration.

Aspect 12. The pharmaceutical composition of any one of aspects 1 to 11, wherein the modified release component comprises a plurality of modified release microparticles.

Aspect 13. The pharmaceutical composition of any one of aspects 1 to 12, wherein the modified release component comprises a suspension of modified release microparticles suitable for oral administration.

Aspect 14. The pharmaceutical composition of any one of aspects 12 to 13, wherein the modified release microparticles comprise a core and a modified release coating surrounding the core.

Aspect 15. The pharmaceutical composition of aspect 14, wherein the core comprises greater than 90 wt % of 4-((L-valyl)oxy)butanoic acid (1), wherein wt % is based on the total weight of the core.

Aspect 16. The pharmaceutical composition of aspect 14, wherein the core comprises greater than 95 wt % of compound (1), wherein wt % is based on the total weight of the core.

Aspect 17. The pharmaceutical composition of any one of aspects 14 to 16, wherein the core comprises an immediate release macroparticle comprising compound (1).

Aspect 18. The pharmaceutical composition of any one of aspects 14 to 17, wherein the modified release coating comprises a plasticizer, a controlled release polymer, a pore former, and an anti-tacking agent.

Aspect 19. The pharmaceutical composition of any one of aspects 14 to 18, wherein the modified release microparticles comprise from 10 wt % to 35 wt % of the modified release coating, wherein wt % is based on the total weight of the modified release microparticles.

Aspect 20. The pharmaceutical composition of any one of aspects 14 to 19, wherein the modified release microparticles comprise:
from 14 wt % to 20 wt % of the modified release coating;
from 20 wt % to 26 wt % of the modified release coating; or
from 25 wt % to 31 wt % of the modified release coating
wherein wt % is based on the total weight of the modified release microparticles.

Aspect 21. The pharmaceutical composition of any one of aspects 1 to 20, wherein,
the modified release component comprises modified release microparticles; and
the modified release microparticles are characterized by a dissolution profile in which from 70 wt % to 90 wt % of compound (1) is released into the dissolution media within 2 hours, from 85% to 100% within 4 hours, and greater than 95% within 6 hours, as determined using a USP Type 2 dissolution apparatus with a buffered solution at pH 4.5 at a temperature of 37° C. and a paddle speed of 75 rpm.

Aspect 22. The pharmaceutical composition of any one of aspects 1 to 20, wherein,
the modified release component comprises modified release microparticles; and
the modified release microparticles are characterized by a dissolution profile in which from 45% to 65% of compound (1) is released into the dissolution media within 2 hours, from 70% to 90% within 4 hours, from 80% to 100% within 6 hours, and greater than 90% within 8 hours, as determined using a USP Type 2 dissolution apparatus with a buffered solution at pH 4.5 at a temperature of 37° C. and a paddle speed of 75 rpm.

Aspect 23. The pharmaceutical composition of any one of aspects 1 to 20, wherein,
the modified release component comprises modified release microparticles; and
the modified release microparticles are characterized by a dissolution profile in which from 25 wt % to 45 wt % of compound (1) is released into the dissolution media within 2 hours, from 60% to 80% within 4 hours, from 70% to 90% within 6 hours, from 80% to 100% within 8 hours and greater than 90% within 12 hours, as determined using a USP Type 2 dissolution apparatus with a buffered solution at pH 4.5 at a temperature of 37° C. and a paddle speed of 75 rpm.

Aspect 24. The pharmaceutical composition of any one of aspects 1 to 23, wherein following oral administration of an IR component comprising 7.25 g of compound (1) to a population of fasted, healthy subjects a pharmacokinetic profile of compound (1) is characterized by a mean $t_{1/2}$ of from 0.35 hours to 0.55 hours, a mean $T_{max}$ from 0.5 hours to 0.7 hours, a mean $C_{max}$ from 16 µg/mL to 20 µg/mL, a mean $AUC_{0-6}$ from 14 h×µg/mL to 18 h×µg/mL, an $AUC_{0-inf}$ from 14 h×µg/mL to 18 h×µg/mL, and/or a CL/F of 480 L/h to 520 L/h.

Aspect 25. The pharmaceutical composition of any one of aspects 1 to 23, wherein following oral administration of an IR component comprising 7.25 g of compound (1) to a population of fasted, healthy subjects a pharmacokinetic profile of γ-hydroxybutyrate is characterized by a mean $t_{1/2}$ from 0.45 hours to 0.85 hours, a mean $T_{max}$ from 0.7 hours to 1.1 hours, a mean $C_{max}$ from 75 µg/mL to 96 µg/mL, an $AUC_{0-6}$ from 147 h×µg/mL to 187 h×µg/mL, an $AUC_{0-inf}$ from 150 h×µg/mL to 190 h×µg/mL, and/or a CL/F from 38 L/h to 58 L/h.

Aspect 26. The pharmaceutical composition of any one of aspects 1 to 23, wherein following oral administration of an IR component comprising 7.25 g of compound (1) to a population of fasted, healthy subjects a pharmacokinetic profile is characterized by a $C_{max}$ ratio from 3.9 to 5.9, and an $AUC_{0-inf}$ ratio from 10.3 to 12.3.

Aspect 27. The pharmaceutical composition of any one of aspects 1 to 26, wherein following oral administration of a modified release component comprising 7.25 g of compound (1) to a population of fasted, healthy subjects a pharmacokinetic profile of compound (1) is characterized by a mean $t_{1/2}$ from 0.7 hours to 1.1 hours, a mean $T_{max}$ from 1.1 hours to 1.5 hours, a mean $C_{max}$ from 0.6 µg/mL to 1.0 µg/mL, a mean $AUC_{0-6}$ from 13 h×µg/mL to 17 h×µg/mL, a mean $AUC_{0-inf}$ from 13 h×µg/mL to 17 h×µg/mL, and/or a mean CL/F from 495 L/h to 535 L/h.

Aspect 28. The pharmaceutical composition of any one of aspects 1 to 26, wherein following oral administration of a modified release component comprising 7.25 g of compound (1) to a population of fasted, healthy subjects a pharmacokinetic profile of γ-hydroxybutyrate is characterized by a mean t/2 from 0.65 hours to 1.05 hours, a mean $T_{max}$ from 1.5 hours to 1.9 hours, a mean $C_{max}$ from 32 µg/mL to 52 µg/mL, a mean $AUC_{0-6}$ from 96 h×µg/mL to 136 h×µg/mL, a mean $AUC_{0-inf}$ from 100 h×µg/mL to 140 h×µg/mL, and/or a mean CL/F from 62 L/h to 102 L/h.

Aspect 29. The pharmaceutical composition of any one of aspects 1 to 26, wherein following oral administration of a modified release component comprising 7.25 g of compound (1) to a population of fasted, healthy subjects a pharmacokinetic profile is characterized by a $C_{max}$ ratio from 5.0 to 5.4, and $AUC_{0-inf}$ ratio from 7.2 to 8.0, where the ratio refers to the ratio of the γ-hydroxybutyrate value to the compound (1) value.

Aspect 30. The pharmaceutical composition of any one of aspects 1 to 26, wherein following oral administration of a modified release component comprising 7.25 g of compound (1) to a population of fasted, healthy subjects a pharmacokinetic profile of compound (1) is characterized by a mean $t_{1/2}$ from 0.6 hours to 1.0 hours, a mean $T_{max}$ from 1.4 hours to 1.8 hours, a mean $C_{max}$ from 3 µg/mL to 7 µg/mL, a mean $AUC_{0-6}$ from 10 h×µg/mL to 14 h×µg/mL, a mean $AUC_{0-inf}$ from 10 h×µg/mL to 14 h×µg/mL, and/or a mean CL/F from 620 L/h to 660 L/h.

Aspect 31. The pharmaceutical composition of any one of aspects 1 to 26, wherein following oral administration of a modified release component comprising 7.25 g of compound (1) to a population of fasted, healthy subjects a pharmacokinetic profile of γ-hydroxybutyrate is characterized by a mean $t_{1/2}$ from 0.8 hours to 1.2 hours, a mean $T_{max}$ from 2.1 hours to 2.5 hours, a mean $C_{max}$ from 23 µg/mL to 27 µg/mL, a mean $AUC_{0-6}$ from 63 h×µg/mL to 83 h×µg/mL, a mean $AUC_{0-inf}$ from 66 h×µg/mL to 86 h×µg/mL, and/or a mean CL/F from 100 L/h to 140 L/h.

Aspect 32. The pharmaceutical composition of any one of aspects 1 to 31, wherein following oral administration of a modified release component comprising 7.25 g of compound (1) to a population of fasted, healthy subjects a pharmacokinetic profile is characterized by a $C_{max}$ ratio from 4.5 to 5.3, and an $AUC_{0-inf}$ ratio from 5.9 to 6.7, where the ratio refers to the ratio of the γ-hydroxybutyrate value to the compound (1) value.

Aspect 33. The pharmaceutical composition of any one of aspects 1 to 32, wherein following oral administration of a modified release component comprising 7.25 g of compound (1) to a population of fasted, healthy subjects a pharmacokinetic profile of compound (1) is characterized by a mean $t_{1/2}$ from 0.8 hours to 1.2 hours, a mean $T_{max}$ from 2.1 hours to 2.5 hours, a mean $C_{max}$ from 3.5 µg/mL to 3.9 µg/mL, a mean $AUC_{0-6}$ from 8 h×µg/mL to 12 h×µg/mL, a mean $AUC_{0-inf}$ from 9 h×µg/mL to 13 h×µg/mL, and/or a mean CL/F from 695 L/h to 735 L/h.

Aspect 34. The pharmaceutical composition of any one of aspects 1 to 26, wherein following oral administration of a modified release component comprising 7.25 g of compound (1) to a population of fasted, healthy subjects a pharmacokinetic profile of γ-hydroxybutyrate is characterized by a mean $t_{1/2}$ from 1.3 hours to 1.7 hours, a mean $T_{max}$ from 2.8 hours to 3.2 hours, a mean $C_{max}$ from 14 µg/mL to 18 µg/mL, a mean $AUC_{0-6}$ from 45 h×µg/mL to 53 h×µg/mL, a mean $AUC_{0-inf}$ from 51 h×µg/mL to 59 h×µg/mL, and/or a mean CL/F from 136 L/h to 156 L/h.

Aspect 35. The pharmaceutical composition of any one of aspects 1 to 34, wherein following oral administration of a modified release component comprising 7.25 g of compound (1) to a population of fasted, healthy subjects a pharmacokinetic profile is characterized by a $C_{max}$ ratio from 4.0 to 4.8, and an $AUC_{0-inf}$ ratio from 4.8 to 5.6, where the ratio refers to the ratio of the γ-hydroxybutyrate value to the compound (1) value.

Aspect 36. The pharmaceutical composition of any one of aspects 1 to 35, wherein,
the immediate release component comprises from 2 g to 8 g of compound (1); and
the modified release component comprises from 8 g to 16 g of compound (1).

Aspect 37. The pharmaceutical composition of any one of aspects 1 to 36, wherein,
the immediate release component comprises from 20 wt % to 40 wt % of compound (1); and
the modified release component comprises from 60 wt % to 80 wt % of compound (1),
wherein wt % is based on the total weight of compound (1).

Aspect 38. The pharmaceutical composition of any one of aspects 1 to 37, wherein a weight ratio of compound (1) in the immediate release component to compound (1) in the modified release component is from 1:2 to 1:3.

Aspect 39. The pharmaceutical composition of any one of aspects 1 to 38, wherein following oral administration of a combined release formulation comprising:

an IR component comprising 4.5 g of compound (1); and
a modified release component comprising 10 g of compound (1) to a population of fasted, healthy subjects,
the pharmacokinetic profile of compound (1) is characterized by a mean $t_{1/2}$ from 0.6 hours to 0.8 hours, a mean $T_{max}$ from 0.5 hours to 0.7 hours, a mean $C_{max}$ from 10 μg/mL to 30 μg/mL, a mean $AUC_{0-6}$ from 20 h×μg/mL to 40 h×μg/mL, a mean $AUC_{0-inf}$ from 20 h×μg/mL to 40 h×μg/mL, and/or a mean CL/F from 440 L/h to 540 L/h.

Aspect 40. The pharmaceutical composition of any one of aspects 1 to 38, wherein following oral administration of a combined release formulation comprising:

an IR component comprising 4.5 g of compound (1); and
a
a modified release component comprising 10 g of compound (1) to a population of fasted, healthy subjects,
the pharmacokinetic profile of γ-hydroxybutyrate is characterized by a mean $t_{1/2}$ from 0.6 hours to 0.8 hours, a mean $T_{max}$ from 1.6 hours to 2.0 hours, a mean $C_{max}$ from 80 μg/mL to 120 μg/mL, a mean $AUC_{0-6}$ from 340 h×μg/mL to 420 h×μg/mL, a mean $AUC_{0-inf}$ from 360 h×μg/mL to 440 h×μg/mL, and/or a mean CL/F from 360 L/h to 440 L/h.

Aspect 41. The pharmaceutical composition of any one of aspects 1 to 38, wherein following oral administration of a combined release formulation comprising:

an IR component comprising 4.5 g of compound (1); and
a modified release component comprising 10 g of compound (1) to a population of fasted, healthy subjects,
the pharmacokinetic profile is characterized by a $C_{max}$ ratio from 4.5 to 6.5, and an $AUC_{0-inf}$ ratio from 11.5 to 15.5, where the ratio refers to the ratio of the γ-hydroxybutyrate value to the corresponding compound (1) value.

Aspect 42. The pharmaceutical composition of any one of aspects 1 to 38, wherein following oral administration of a combined release formulation comprising:

an IR component comprising 4.5 g of compound (1); and
a modified release component comprising 10 g of compound (1) to a population of fasted, healthy subjects,
the pharmacokinetic profile of compound (1) is characterized by a mean $t_{1/2}$ from 0.7 hours to 1.1 hours, a mean $T_{max}$ from 0.7 hours to 0.9 hours, a mean $C_{max}$ from 15 μg/mL to 19 μg/mL, a mean $AUC_{0-6}$ from 22 h×μg/mL to 30 h×μg/mL, a mean $AUC_{0-inf}$ from 22 h×μg/mL to 30 h×μg/mL, and/or a mean CL/F of 530 L/h to 610 L/h.

Aspect 43. The pharmaceutical composition of any one of aspects 1 to 38, wherein following oral administration of a combined release formulation comprising:

an IR component comprising 4.5 g of compound (1); and
a modified release component comprising 10 g of compound (1) to a population of fasted, healthy subjects,
the pharmacokinetic profile of γ-hydroxybutyrate is characterized by a mean $t_{1/2}$ from 0.8 hours to 1.0 hours, a mean $T_{max}$ from 1.1 hours to 1.5 hours, a mean $C_{max}$ from 65 μg/mL to 85 μg/mL, a mean $AUC_{0-6}$ from 290 h×μg/mL to 330 h×μg/mL, a mean $AUC_{0-inf}$ from 320 h×μg/mL to 360 h×μg/mL, and/or a mean CL/F from 505 L/h to 545 L/h.

Aspect 44. The pharmaceutical composition of any one of aspects 1 to 38, wherein following oral administration of a combined release formulation comprising:

an IR component comprising 4.5 g of compound (1); and
a modified release component comprising 10 g of compound (1) to a population of fasted, healthy subjects, the pharmacokinetic profile is characterized by a $C_{max}$ ratio from 4.7 to 5.1, and an $AUC_{0-inf}$ ratio from 11 to 15, where the ratio refers to the ratio of the γ-hydroxybutyrate value to the corresponding compound (1) value.

Aspect 45. The pharmaceutical composition of any one of aspects 1 to 38, wherein following oral administration of a combined release formulation comprising:

an IR component comprising 4.5 g of compound (1); and
a modified release component comprising 13.5 g of compound (1) to a population of fasted, healthy subjects,
the pharmacokinetic profile of compound (1) is characterized by a mean $t_{1/2}$ from 1.0 hours to 1.2 hours, a mean $T_{max}$ from 0.9 hours to 1.1 hours, a mean $C_{max}$ from 15 μg/mL to 23 μg/mL, a mean $AUC_{0-6}$ from 28 h×μg/mL to 36 h×μg/mL, a mean $AUC_{0-inf}$ from 30 h×μg/mL to 38 h×μg/mL, and/or a mean CL/F from 550 L/h to 590 L/h.

Aspect 46. The pharmaceutical composition of any one of aspects 1 to 38, wherein following oral administration of a combined release formulation comprising:

an IR component comprising 4.5 g of compound (1); and
a modified release component comprising 13.5 g of compound (1) to a population of fasted, healthy subjects,
the pharmacokinetic profile of γ-hydroxybutyrate is characterized by a mean $t_{1/2}$ from 0.9 hours to 1.1 hours, a mean $T_{max}$ from 1.5 hours to 1.9 hours, a mean $C_{max}$ from 85 μg/mL to 105 μg/mL, a mean $AUC_{0-6}$ from 314 h×μg/mL to 354 h×μg/mL, a mean $AUC_{0-inf}$ from 370 h×μg/mL to 410 h×μg/mL, and/or a mean CL/F from 45 L/h to 65 L/h.

Aspect 47. The pharmaceutical composition of any one of aspects 1 to 38, wherein following oral administration of a combined release formulation comprising:

an IR component comprising 4.5 g of compound (1); and
a modified release component comprising 13.5 g of compound (1) to a population of fasted, healthy subjects,
the pharmacokinetic profile is characterized by a $C_{max}$ ratio from 5.0 to 5.6, and an $AUC_{0-inf}$ ratio from 10 to 14, where the ratio refers to the ratio of the γ-hydroxybutyrate value to the corresponding compound (1) value.

Aspect 48. The pharmaceutical composition of any one of aspects 1 to 38, wherein following oral administration of a combined release formulation comprising:

an IR component comprising 6 g of compound (1); and
a modified release component comprising 12 g of compound (1) to a population of fasted, healthy subjects,
the pharmacokinetic profile of compound (1) is characterized by a mean $t_{1/2}$ from 1.0 hours to 1.2 hours, a mean $T_{max}$ from 1.0 hours to 1.2 hours, a mean $C_{max}$ from 17 μg/mL to 21 μg/mL, a mean $AUC_{0-6}$ from 29 h×μg/mL to 33 h×μg/mL, a mean $AUC_{0-inf}$ from 32 h×μg/mL to 36 h×μg/mL, and/or a mean CL/F from 535 L/h to 575 L/h.

Aspect 49. The pharmaceutical composition of any one of aspects 1 to 38, wherein following oral administration of a combined release formulation comprising:

an IR component comprising 6 g of compound (1); and
a modified release component comprising 12 g of compound (1) to a population of fasted, healthy subjects,
the pharmacokinetic profile of γ-hydroxybutyrate is characterized by a mean $t_{1/2}$ from 0.8 hours to 1.0 hours, a mean $T_{max}$ from 2.0 hours to 2.4 hours, a mean $C_{max}$ from 88 μg/mL to 96 μg/mL, a mean $AUC_{0-6}$ from 310 h×μg/mL to 350 h×μg/mL, a mean $AUC_{0-inf}$ h×μg/mL from 380 h×μg/mL to 420 h×μg/mL, and/or a mean CL/F from 51 L/h to 59 L/h.

Aspect 50. The pharmaceutical composition of any one of aspects 1 to 49, wherein following oral administration of a combined release formulation comprising:

an IR formulation comprising 6 g of compound (1); and
a modified release component comprising 12 g of compound (1) to a population of fasted, healthy subjects, the pharmacokinetic profile is characterized by a $C_{max}$ ratio from 4 to 8, and an $AUC_{0-inf}$ ratio from 10 to 14, where the ratio refers to the ratio of the γ-hydroxybutyrate value to the corresponding compound (1) value.

Aspect 51. The pharmaceutical composition of any one of aspects 1 to 50, wherein, at 6 hours following oral administration of the pharmaceutical composition to a population of fasted, healthy subjects, the concentration of γ-hydroxybutyrate in the plasma of the subjects is less than 15 μg/mL, less than 10 μg/mL, or less than 5 μg/mL.

Aspect 52. The pharmaceutical composition of any one of aspects 1 to 51, wherein following oral administration of a pharmaceutical composition comprising from 10 g to 20 g of compound (1) to a population of fasted, healthy subjects, the γ-hydroxybutyrate concentration in the plasma of the subjects is greater than the sum of: (a) the $AUC_{inf}$ of γ-hydroxybutyrate following oral administration of the immediate release component; and (b) the $AUC_{inf}$ of γ-hydroxybutyrate following oral administration of the modified release component to the population of fasted, healthy subjects.

Aspect 53. The pharmaceutical composition of any one of aspects 1 to 52, wherein between 6 hours and 8 hours following oral administration of a pharmaceutical composition comprising from 10 g to 20 g of compound (1) to a population of fasted, healthy subjects, the γ-hydroxybutyrate concentration in the plasma of the subjects is greater than the sum of: (a) the γ-hydroxybutyrate concentration between 6 hours and 8 hours following oral administration of the immediate release component; and (b) the γ-hydroxybutyrate concentration between 6 hours and 8 hours following oral administration of the modified release component to the population of fasted, healthy subjects.

Aspect 54. The pharmaceutical composition of any one of aspects 1 to 53, wherein following oral administration of a pharmaceutical composition comprising from 10 g to 20 g of compound (1) to a population of healthy, fasted subjects, concentration from 6 hours to 8 hours following administration is greater than the concentration of γ-hydroxybutyrate in the plasma of the subjects following administration of the modified release component alone.

Aspect 55. The pharmaceutical composition of any one of aspects 1 to 54, wherein the mean γ-hydroxybutyrate $AUC_{0-inf}$ following oral administration of the immediate release component and the modified release component to a population of fasted, healthy subjects is greater the sum of the mean γ-hydroxybutyrate $AUC_{0-inf}$ following oral administration of the immediate release component alone, and the mean γ-hydroxybutyrate $AUC_{0-inf}$ following oral administration of the modified release component alone.

Aspect 56. The pharmaceutical composition of any one of aspects 1 to 55, wherein the mean compound (1) $AUC_{0-inf}$ following oral administration of the immediate release component and the modified release component to a population of subjects is substantially the same as than the sum of the mean compound (1) $AUC_{0-inf}$ following oral administration of the immediate release component alone, and the mean compound (1) $AUC_{0-inf}$ following oral administration of the modified release component alone.

Aspect 57. The pharmaceutical composition of any one of aspects 1 to 56, wherein the mean γ-hydroxybutyrate $AUC_{0-inf}$ following oral administration of a pharmaceutical composition comprising an immediate release component comprising 4.52 g of compound (1) and a modified release component comprising 10 gm compound (1) to a population of fasted, healthy subjects is greater than the sum of the mean γ-hydroxybutyrate $AUC_{0-inf}$ following oral administration of an immediate release component comprising 7.25 g of compound (1) alone, and the mean γ-hydroxybutyrate $AUC_{0-inf}$ following oral administration of a modified release component comprising 7.25 g of compound (1) alone.

Aspect 58. The pharmaceutical composition of any one of aspects 1 to 57, wherein the mean compound (1) $AUC_{0-inf}$ following oral administration of a pharmaceutical composition comprising an immediate release component comprising 4.52 g of compound (1) and a modified release component comprising 10 gm compound (1) to a population of fasted, healthy subjects is substantially the same as than the sum of the mean compound (1) $AUC_{0-inf}$ following oral administration of an immediate release component comprising 7.25 g of compound (1) alone, and the mean compound (1) $AUC_{0-inf}$ following oral administration of a modified release component comprising 7.25 g of compound (1) alone.

Aspect 59. The pharmaceutical composition of any one of aspects 1 to 58, wherein following oral administration of the pharmaceutical composition to a population of fasted, healthy subjects the plasma γ-hydroxybutyrate pharmacokinetic profile is characterized by a mean $T_{max}$ of less than 2.4 hours.

Aspect 60. The pharmaceutical composition of any one of aspects 1 to 59, wherein following oral administration of the pharmaceutical composition to a population of fasted, healthy subjects the plasma γ-hydroxybutyrate pharmacokinetic profile is characterized by a mean $T_{max}$ from 1.4 hours to 2.4 hours.

Aspect 61. The pharmaceutical composition of any one of aspects 1 to 60, wherein following oral administration of the pharmaceutical composition to a population of fasted, healthy subjects the plasma γ-hydroxybutyrate pharmacokinetic profile is characterized by a mean $C_{max}$ of less than 100 μg/mL.

Aspect 62. The pharmaceutical composition of any one of aspects 1 to 61, wherein following oral administration of the pharmaceutical composition to a population of fasted, healthy subjects the plasma γ-hydroxybutyrate pharmacokinetic profile is characterized by a mean $C_{max}$ from 75 μg/mL to 105 μg/mL.

Aspect 63. The pharmaceutical composition of any one of aspects 1 to 62, wherein following oral administration of the pharmaceutical composition to a population of fasted, healthy subjects the plasma γ-hydroxybutyrate pharmacokinetic profile is characterized by a mean $AUC_{0-6h}$ of greater than 250 h×μg/mL.

Aspect 64. The pharmaceutical composition of any one of aspects 1 to 63, wherein following oral administration of the pharmaceutical composition to a population of fasted, healthy subjects the plasma γ-hydroxybutyrate pharmacokinetic profile is characterized by a mean $C_6$ of less than 36 μg/mL.

Aspect 65. The pharmaceutical composition of any one of aspects 1 to 64, wherein following oral administration of the pharmaceutical composition to a population of fasted, healthy subjects the plasma γ-hydroxybutyrate pharmacokinetic profile is characterized by a mean $C_6$ of from 18 μg/mL to 36 μg/mL.

Aspect 66. The pharmaceutical composition of any one of aspects 1 to 65, wherein following oral administration of the pharmaceutical composition to a population of fasted, healthy subjects the plasma γ-hydroxybutyrate pharmacokinetic profile is characterized by a mean $C_8$ of from 4 μg/mL to 20 μg/mL.

Aspect 67. The pharmaceutical composition of any one of aspects 1 to 66, wherein following oral administration of the pharmaceutical composition to a population of fasted, healthy subjects the plasma γ-hydroxybutyrate pharmacokinetic profile is characterized by a mean $C_{10h}$ of less than 10 µg/mL.

Aspect 68. The pharmaceutical composition of any one of aspects 1 to 67, wherein following oral administration of the pharmaceutical composition to a population of fasted, healthy subjects the plasma γ-hydroxybutyrate pharmacokinetic profile is characterized by a plasma γ-hydroxybutyrate concentration greater than 10 µg/mL for from 5 hours to 7 hours.

Aspect 69. The pharmaceutical composition of any one of aspects 1 to 68, wherein following oral administration of the pharmaceutical composition to a population of fasted, healthy subjects the plasma γ-hydroxybutyrate pharmacokinetic profile is characterized by a plasma γ-hydroxybutyrate concentration from 10 µg/mL to 30 µg/mL for from 5 hours to 7 hours.

Aspect 70. The pharmaceutical composition of any one of aspects 1 to 69, wherein following oral administration of the pharmaceutical composition to a population of fasted, healthy subjects the plasma γ-hydroxybutyrate pharmacokinetic profile is characterized by a $C_{max}/C_{5h}$ ratio of less than 4.

Aspect 71. The pharmaceutical composition of any one of aspects 1 to 70, wherein following oral administration of the pharmaceutical composition to a population of fasted, healthy subjects the plasma γ-hydroxybutyrate pharmacokinetic profile is characterized by a $C_{max}/C_{5h}$ ratio of from 1.5 to 4.

Aspect 72. The pharmaceutical composition of any one of aspects 1 to 71, wherein following oral administration of the pharmaceutical composition to a population of fasted, healthy subjects the plasma γ-hydroxybutyrate pharmacokinetic profile is characterized by a $C_{max}/C_{6h}$ ratio of greater than 2.

Aspect 73. The pharmaceutical composition of any one of aspects 1 to 72, wherein following oral administration of the pharmaceutical composition to a population of fasted, healthy subjects the plasma γ-hydroxybutyrate pharmacokinetic profile is characterized by a $C_{max}/C_{6h}$ ratio of from 2 to 10.

Aspect 74. The pharmaceutical composition of any one of aspects 1 to 73, wherein following oral administration of the pharmaceutical composition to a population of fasted, healthy subjects the plasma γ-hydroxybutyrate pharmacokinetic profile is characterized by a $C_{max}/C_{8h}$ ratio of greater than 5.

Aspect 75. The pharmaceutical composition of any one of aspects 1 to 74, wherein following oral administration of the pharmaceutical composition to a population of fasted, healthy subjects the plasma γ-hydroxybutyrate pharmacokinetic profile is characterized by a $C_{max}/C_{6h}$ ratio of from 5 to 20.

Aspect 76. The pharmaceutical composition of any one of aspects 1 to 75, wherein following oral administration of the pharmaceutical composition to a population of fasted, healthy subjects the plasma γ-hydroxybutyrate pharmacokinetic profile is characterized by a $AUC_{0-8h}/AUC_{inf}$ ratio of greater than 0.6.

Aspect 77. The pharmaceutical composition of any one of aspects 1 to 76, wherein following oral administration of the pharmaceutical composition to a population of fasted, healthy subjects the plasma γ-hydroxybutyrate pharmacokinetic profile is characterized by a $AUC_{0-8h}/AUC_{inf}$ ratio of from 0.6 to 1.2.

Aspect 78. The pharmaceutical composition of any one of aspects 1 to 77, wherein following oral administration of the pharmaceutical composition to a population of fasted, healthy subjects the plasma γ-hydroxybutyrate pharmacokinetic profile is characterized by an $AUC_{inf}$ of greater than 250 h×µg/mL.

Aspect 79. The pharmaceutical composition of any one of aspects 1 to 78, wherein following oral administration of the pharmaceutical composition to a population of fasted, healthy subjects the plasma γ-hydroxybutyrate pharmacokinetic profile is characterized by an $AUC_{inf}$ from 250 h×µg/mL to 450 h×µg/mL.

Aspect 80. The pharmaceutical composition of any one of aspects 1 to 79, wherein the pharmaceutical composition can comprise 14.5 g of compound (1) corresponding to 9 g γ-hydroxybutyrate equivalents, with 4.5 g of compound (1) in the immediate release component and 10 g compound (1) in the modified release component.

Aspect 81. The pharmaceutical composition of aspect 80, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $T_{max}$ from 2.0 hours to 3.2 hours.

Aspect 82. The pharmaceutical composition of any one of aspects 80 to 81, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $C_{max}$ from 94 µg/mL to 114 µg/mL.

Aspect 83. The pharmaceutical composition of any one of aspects 80 to 82, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $AUC_{inf}$ from 430 hr×µg/mL to 490 hr×µg/mL.

Aspect 84. The pharmaceutical composition of any one of aspects 80 to 83, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $AUC_{0-6}$ from 360 hr×µg/mL to 420 hr×µg/mL.

Aspect 85. The pharmaceutical composition of any one of aspects 80 to 84, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $C_6$ from 25 µg/mL to 55 µg/mL.

Aspect 86. The pharmaceutical composition of any one of aspects 80 to 85, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $C_8$ from 5 µg/mL to 15 µg/mL.

Aspect 87. The pharmaceutical composition of any one of aspects 80 to 86, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $C_{10}$ less than 5 µg/mL.

Aspect 88. The pharmaceutical composition of any one of aspects 80 to 87, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $C_{max}/C_8$ ratio from 9 to 11.

Aspect 89. The pharmaceutical composition of any one of aspects 80 to 88, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by a mean $T_{max}$ from 2.0 hours to 3.2 hours, a mean $C_{max}$ from 94 μg/mL to 114 μg/mL, a mean $AUC_{inf}$ from 430 hr×μg/mL to 490 hr×μg/mL, a mean $AUC_{0-6}$ from 360 hr×μg/mL to 420 hr×μg/mL, a mean $C_6$ from 25 μg/mL to 55 μg/mL, a mean $C_8$ from 5 μg/mL to 15 μg/mL, a mean $C_{10}$ less than 5 μg/mL, and/or a mean $C_{max}/C_8$ ratio from 9 to 11.

Aspect 90. The pharmaceutical composition of any one of aspects 80 to 89, wherein following oral administration of the pharmaceutical composition comprising 4.5 g of compound (1) in an IR component and 10 g of compound (1) in an MR component to a population of fasted, healthy subjects a pharmacokinetic profile of γ-hydroxybutyrate can be characterized by plasma γ-hydroxybutyrate greater than 25 μg/mL for at least 4 hours.

Aspect 91. A method of treating fatigue or excessive daytime sleepiness associated with narcolepsy in a patient comprising orally administering to a patient in need of such treatment a therapeutically effective amount of the pharmaceutical composition of any one of aspects 1 to 90.

Aspect 92. A method of treating narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia in a patient comprising orally administering to a patient in need of such treatment a therapeutically effective amount of the pharmaceutical composition of any one of aspects 1 to 89.

Aspect 93. A method of treating a symptom associated with narcolepsy, excessive daytime sleepiness, cataplexy, excessive daytime sleepiness associated with narcolepsy, excessive daytime sleepiness associated with Parkinson's disease, excessive daytime sleepiness associated with multiple sclerosis, cataplexy associated with narcolepsy, fatigue, fatigue associated with Parkinson's diseases, fatigue associated with multiple sclerosis, or fibromyalgia in a patient comprising orally administering to a patient in need of such treatment a therapeutically effective amount of the pharmaceutical composition of any one of aspects 1 to 90.

Aspect 94. A method of treating REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety in a patient comprising orally administering to a patient in need of such treatment a therapeutically effective amount of the pharmaceutical composition of any one of aspects 1 to 90.

Aspect 95. A method of treating a symptom associated with REM sleep behavior disorder, spasmodic dystonia, schizophrenia, insomnia, insomnia associated with schizophrenia, idiopathic hypersomnia, chronic fatigue syndrome, cluster headache, Alzheimer's disease, essential tremor, post-traumatic stress syndrome, insomnia associated with post-traumatic stress syndrome, or anxiety in a patient comprising orally administering to a patient in need of such treatment a therapeutically effective amount of the pharmaceutical composition of any one of aspects 1 to 90.

Aspect 96. A method of treating a sleep disorder associated with a bacterial infection in a patient comprising orally administering to a patient in need of such treatment, a therapeutically effective amount of the pharmaceutical composition of any one of aspects 1 to 90.

Aspect 97. The method of aspect 96, wherein the bacterial infection is a COVID-19 infection.

Aspect 98. A method of enhancing cognitive function in a patent having a neurological disorder comprising orally administering to a patient in need of such treatment, a therapeutically effective amount of the pharmaceutical composition of any one of aspects 1 to 90.

Aspect 99. The method of any one of aspects 92 to 98, wherein administering comprises administering QD.

Aspect 100. The method of any one of aspects 91 to 98, wherein administering comprises administering BID.

Aspect 101. The method of any one of aspects 91 to 98, wherein administering comprising administering once nightly.

Aspect 102. A kit comprising the pharmaceutical composition of any one of aspects 1 to 90.

EXAMPLES

Embodiments provided by the present disclosure are further illustrated by reference to the following examples, which describe microparticles comprising compound (1), immediate release and modified release components comprising compound (1), pharmaceutical compositions comprising compound (1), and the pharmacokinetics of compound (1) and γ-hydroxybutyrate following oral administration of the pharmaceutical compositions to fasted, healthy subjects. It will be apparent to those skilled in the art that many modifications, both to materials, and methods, may be practiced without departing from the scope of the disclosure. It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

General Methods

The plasma concentrations of compound (1) and γ-hydroxybutyrate in plasma of healthy human subjects were measured using liquid chromatography tandem mass-spectroscopy and evaluated using PHOENIX™ WINNONLIN® version 8.1 (Pharsight Corporation, USA) and MICROSOFT® EXCEL® 2016 (Microsoft Corporation, USA).

Example 1

Oral Formulations

The constituents of immediate release (IR) microparticles and three (3) modified release (MR1, MR2, and MR3) microparticles comprising compound (1) are provided in Table 1.

TABLE 1

Composition of immediate release (IR) and modified release (MR) microparticles.

| Component | Quality Standard | Function | Amount (% w/w) | | | |
|---|---|---|---|---|---|---|
| | | | IR | MR1 | MR2 | MR3 |
| Microparticle | | | | | | |
| Compound (1) | In-house Specification | Drug Substance | 98.50 | 82.08 | 75.77 | 70.36 |
| Colloidal silicon dioxide ($SiO_2$) | [2] NF | Anti-tacking agent | 1.00 | 0.83 | 0.77 | 0.71 |
| Hydroxypropyl cellulose, (HPC) | NF | Binder | 0.50 | 0.42 | 0.38 | 0.36 |
| [1] Purified Water | [2] USP | Solvent | — | — | — | — |
| Coating | | | | | | |
| Dibutyl sebacate | NF | Plasticizer | — | 1.28 | 1.78 | 2.20 |
| [1] Ethyl alcohol | USP | Solvent | — | — | — | — |
| Ethylcellulose | NF | Controlled release polymer | — | 12.18 | 16.86 | 20.88 |
| Hydroxypropyl cellulose (HPC) | NF | Pore former | — | 0.64 | 0.89 | 1.10 |
| Magnesium silicate, hydrous (Talc) | USP | Anti-tacking agent | — | 2.56 | 3.55 | 4.40 |
| [1] Purified Water | USP | Solvent | — | — | — | — |

[1] Removed during processing.
[2] USP/NF: United States Pharmacopeia/National Formulary, current edition.

To prepare the immediate release microparticles, compound (1) was first milled and then combined with colloidal $SiO_2$ and hydroxypropyl cellulose and mixed. Water was added and mixed to provide a wet granulation. The wet granulation was co-milled through a screen to form a wet mass. The wet mass was granulated with the addition of water to form a granulation that was mixed to form microparticles. The microparticles were dried at 40° C. for from 12 hours to 24 hours. The dried microparticles were sorted by size. Microparticles having a size (D4,3) from 200 μm to 500 μm were separated and used for the pharmacokinetic studies.

The immediate release microparticles contained 98.5 wt % of compound (1) 4-((L-valyl)oxy)butanoic acid, where wt % is based on the total weight of the immediate release microparticles.

To prepare the modified release microparticles, a coating mixture was prepared by first combining and mixing ethyl alcohol, ethyl cellulose, hydroxypropyl cellulose, water, magnesium silicate (hydrous), and dibutyl sebacate to provide a coating suspension. The coating suspension was sprayed onto immediate release microparticles to different thicknesses to provide the three modified release microparticles used in the pharmacokinetic studies.

Following coating, the immediate release microparticles had a weight gain of 20%, 30%, or 40% for the MR1 (20% wg), MR2 (30% wg), and MR3 (40% wg) modified release microparticles, respectively.

Example 2

Dissolution Profiles

The dissolution profiles for the modified release microparticles were determined using a USP Type 2 dissolution apparatus with a buffered solution at pH 4.5 at a temperature of 37° C. and a paddle speed of 75 rpm. The dissolution profiles for the release of compound (1) from the modified release microparticles is shown in FIG. 1.

Example 3

Pharmacokinetics of Immediate Release Component and Modified Release Component

The pharmacokinetics of compounds (1) and γ-hydroxybutyrate following oral administration of an immediate release component or modified release component to fasted, healthy subjects was determined.

To prepare an immediate release formulation, immediate release microparticles prepared according to Example 1 were added to 30 mL water and gently swirled to dissolve the immediate release microparticles. Water was added to bring the total volume to 250 mL to provide an immediate release oral formulation which was ingested by the subject.

To prepare the modified release formulations, modified release microparticles prepared according to Example 1 were added to 30 mL of water and gently swirled. ORA-PLUS® (30 mL) was added, the contents gently swirled, and the suspension ingested by the subject. Additional water up to a total volume of 250 mL was used to rinse the container and was also ingested by the subject.

Each formulation contained 7.25 g of compound (1) (3.172 g γ-hydroxybutyrate-equivalents).

Pharmacokinetic profiles for compound (1) and γ-hydroxybutyrate following oral administration of the immediate release (IR) and modified release (MR1-MR3) formulations to fasted, healthy subjects are shown in FIG. 2A for compound (1) and in FIG. 2B for γ-hydroxybutyrate. The results represent the mean and standard deviation based on the results for from 10 to 12 subjects.

Pharmacokinetic parameters for compound (1) and γ-hydroxybutyrate following oral administration of the IR and MR microparticles are provided in Table 2 and Table 3, respectively. The results represent the mean and standard deviation based on the results for from 10 to 12 subjects.

TABLE 2

Pharmacokinetic parameters for compound (1) following oral administration of immediate release or modified release formulations.

| Formulation | | $T_{max}$ (h) | $C_{max}$ (µg/mL) | $AUC_{last}$ (h × µg/mL) | $AUC_{inf}$ (h × µg/mL) | $AUC_{0-6}$ (h × µg/mL) | $AUC_{0-8}$ (h × µg/mL) | $AUC_{0-12}$ (h × µg/mL) | CL/F (L/h) | $t_{1/2}$ (h) |
|---|---|---|---|---|---|---|---|---|---|---|
| IR | Mean | 0.6 | 18 | 16 | 16 | 16 | 16 | 16 | 501 | 0.4 |
|    | CV % | 33.4 | 25 | 26 | 26 | 26 | 26 | 26 | 35 | 75 |
| MR1 | Mean | 1.3 | 8 | 15 | 15 | 15 | 15 | 15 | 514 | 0.9 |
|     | CV % | 26 | 27 | 30 | 30 | 29 | 30 | 30 | 29 | 39 |
| MR2 | Mean | 1.6 | 5 | 12 | 12 | 14 | 12 | 12 | 642 | 0.8 |
|     | CV % | 12.3 | 21 | 30 | 30 | 28 | 30 | 30 | 21 | 44 |
| MR3 | Mean | 2.3 | 4 | 10 | 11 | 10 | 10 | 10 | 715 | 1.0 |
|     | CV % | 32.1 | 30 | 23 | 23 | 23 | 23 | 24 | 20 | 49 |

TABLE 3

Pharmacokinetic parameters for γ-hydroxybutyrate following oral administration of immediate release or modified release formulations.

| Microparticle | | $T_{max}$ (h) | $C_{max}$ (µg/mL) | $AUC_{last}$ (h × µg/mL) | $AUC_{inf}$ (h × µg/mL) | $AUC_{0-6}$ (h × µg/mL) | $AUC_{0-8}$ (h × µg/mL) | $AUC_{0-12}$ (h × µg/mL) | CL/F (L/h) | $t_{1/2}$ (h) |
|---|---|---|---|---|---|---|---|---|---|---|
| IR | Mean | 0.9 | 83 | 167 | 168 | 167 | 168 | 168 | 48 | 0.7 |
|    | CV % | 26 | 23 | 35 | 34 | 34 | 34 | 35 | 37 | 29 |
| MR1 | Mean | 1.7 | 41 | 119 | 120 | 116 | 119 | 119 | 82 | 0.8 |
|     | CV % | 23 | 39 | 55 | 55 | 53 | 55 | 55 | 59 | 18 |
| MR2 | Mean | 2.2 | 25 | 75 | 76 | 73 | 75 | 76 | 119 | 1.0 |
|     | CV % | 15 | 37 | 48 | 48 | 47 | 48 | 48 | 50 | 22 |
| MR3 | Mean | 3.0 | 16 | 53 | 55 | 49 | 53 | 54 | 146 | 1.4 |
|     | CV % | 35 | 39 | 37 | 35 | 37 | 36 | 36 | 36 | 51 |

The $C_{max}$ Ratio, $AUC_{0-inf}$ Ratio, and $AUC_{0-8}$ Ratio are shown in Table 4, where the ratios refer to the γ-hydroxybutyrate value divided by the corresponding compound (1) value. For example, the $C_{max}$ ratio equals $(C_{max}(GHB)/C_{max}$ (Compound 1).

TABLE 4

Pharmacokinetic ratios for immediate release and modified release formulations.

| Microparticle | $C_{max}$ Ratio | $AUC_{inf}$ Ratio | $AUC_{0-8}$ Ratio |
|---|---|---|---|
| IR | 4.9 | 11.3 | 11.3 |
| MR1 | 5.2 | 7.6 | 7.6 |
| MR2 | 4.0 | 6.3 | 6.3 |
| MR3 | 4.5 | 5.2 | 5.1 |

Example 4

Pharmacokinetics of Combined-Release Formulations

The pharmacokinetics of combined-release (CR) formulations comprising an immediate release component and a modified release component was determined.

The amounts of compound (1) in the immediate release components and in the modified release component used to prepare the combined release formulations (CR1-CR4) are summarized in Table 5.

TABLE 5

Content of combined release (CR) formulations.

| | Compound (1) (g) | | | | |
|---|---|---|---|---|---|
| Combined Release Formulation | IR 98.5 wt % Compound (1) | MR1 82.08 wt % Compound (1) | MR2 75.77 wt % Compound (1) | Total | |
| CR1 | 4.5 | 10.0 | — | 14.5 | Compound (1) (g) |
|     | 2.8 | 6.2 | — | 9.0 | GHB equivalents |
| CR2 | 4.5 | — | 10.0 | 14.5 | Compound (1) (g) |
|     | 2.8 | — | 6.2 | 9.0 | GHB equivalents |
| CR3 | 4.5 | 13.5 | — | 18.0 | Compound (1) (g) |
|     | 2.8 | 8.4 | — | 11.2 | GHB equivalents |
| CR4 | 6.0 | — | 12.0 | 18.0 | Compound (1) (g) |
|     | 3.7 | — | 7.4 | 11.2 | GHB equivalents |

To prepare combined release formulations, the immediate release microparticles were dissolved in 30 mL of water. The modified release microparticles were then added and swirled gently. Thirty (30) mL of ORA-PLUS®, an oral suspending vehicle, was added and the suspension gently stirred. The subjects then drank the suspension. The subjects repeatedly rinsed the cup with up to 250 mL of water and drank the solution.

Pharmacokinetic profiles for compound (1) and γ-hydroxybutyrate following oral administration of the combined release formulations (CR1-CR4) to fasted, healthy subjects are shown in tabular form in FIG. 3 and FIG. 4, respectively. The pharmacokinetic profiles for γ-hydroxybutyrate are shown in FIG. 5. The results represent the mean and standard deviation based on from 10 to 12 subjects.

A summary of certain pharmacokinetic parameters for compound (1) and γ-hydroxybutyrate following oral administration of the combined release formulations to fasted, healthy subjects is provided in Tables 6 and 7. The results reflect mean values obtained for from 10 to 12 subjects.

TABLE 6

Pharmacokinetic parameters for compound (1) following oral administration of combined release (CR) formulations.

| Formulation | | $T_{max}$ (h) | $C_{max}$ (μg/mL) | $AUC_{last}$ (h × μg/mL) | $AUC_{inf}$ (h × μg/mL) | $AUC_{0-6}$ (h × μg/mL) | $AUC_{0-8}$ (h × μg/mL) | $AUC_{0-12}$ (h × μg/mL) | CL/F (L/h) | $t_{1/2}$ (h) |
|---|---|---|---|---|---|---|---|---|---|---|
| CR1 | Mean | 0.6 | 20 | 31 | 31 | 30 | 31 | 31 | 493 | 0.7 |
|  | CV % | 34 | 27 | 26 | 26 | 26 | 26 | 27 | 27 | 41 |
| CR2 | Mean | 0.8 | 17 | 26 | 26 | 26 | 26 | 26 | 569 | 0.9 |
|  | CV % | 121 | 33 | 20 | 20 | 20 | 20 | 20 | 20 | 33 |
| CR3 | Mean | 1.0 | 19 | 32 | 34 | 32 | 33 | 34 | 554 | 1.1 |
|  | CV % | 57 | 19 | 24 | 20 | 19 | 19 | 20 | 21 | 60 |
| CR4 | Mean | 1.0 | 16 | 34 | 34 | 31 | 33 | 34 | 559 | 1.1 |
|  | CV % | 63 | 25 | 23 | 23 | 22 | 22 | 23 | 26 | 50 |

TABLE 7

Pharmacokinetic parameters for γ-hydroxybutyrate following oral administration of combined release (CR) formulations.

| Formulation | | $T_{max}$ (h) | $C_{max}$ (μg/mL) | $AUC_{last}$ (h × μg/mL) | $AUC_{inf}$ (h × μg/mL) | $AUC_{0-6}$ (h × μg/mL) | $AUC_{0-8}$ (h × μg/mL) | $AUC_{0-12}$ (h × μg/mL) | CL/F (L/h) | $t_{1/2}$ (h) |
|---|---|---|---|---|---|---|---|---|---|---|
| CR1 | Mean | 1.8 | 99 | 406 | 407 | 379 | 402 | 407 | 39 | 0.7 |
|  | CV % | 41 | 21 | 34 | 34 | 31 | 34 | 34 | 34 | 24 |
| CR2 | Mean | 1.3 | 75 | 341 | 342 | 307 | 334 | 342 | 52 | 1.0 |
|  | CV % | 48 | 20 | 43 | 43 | 37 | 42 | 43 | 53 | 36 |
| CR3 | Mean | 1.7 | 96 | 358 | 389 | 334 | 368 | 387 | 55 | 1.0 |
|  | CV % | 42 | 24 | 52 | 44 | 33 | 40 | 44 | 43 | 33 |
| CR4 | Mean | 2.2 | 92 | 402 | 404 | 332 | 379 | 403 | 55 | 0.9 |
|  | CV % | 63 | 20 | 43 | 44 | 32 | 38 | 43 | 56 | 26 |

The $C_{max}$ Ratio, $AUC_{0-inf}$ Ratio and $AUC_{0-8}$ Ratio for the combined release formulations are shown in Table 8, where the ratios refer to the γ-hydroxybutyrate value divided by the corresponding compound (1) value.

TABLE 8

Pharmacokinetic ratios for combined release (CR) formulations.

| Formulation | $C_{max}$ Ratio | $AUC_{0-8}$ Ratio | $AUC_{inf}$ Ratio |
|---|---|---|---|
| CR1 | 5.28 | 13.21 | 13.25 |
| CR2 | 4.91 | 12.42 | 12.65 |
| CR3 | 5.28 | 11.28 | 11.61 |
| CR4 | 6.00 | 11.51 | 11.98 |

Example 5

Pharmacokinetics of Modified Release Microparticles

Modified release microparticles were prepared by applying a modified release coating to immediate release microparticles.

Immediate release microparticles comprising 4-((L-valyl)oxy)butanoic acid was prepared using MICROPX® micropelletizing technology (Glatt GmbH). The immediate release microparticles had an average granule diameter (D50) from 225 μm to 275 μm. The immediate release microparticles contained 90 wt % 4-((L-valyl)oxy)butanoic acid, 5 wt % USP magnesium silicate, and 5 wt % hypromellose (hydroxypropylmethyl cellulose), where wt % is based on the total weight of the immediate release microparticles.

A modified release coating as described in Example 1 was applied to the immediate release microparticles to provide the modified release microparticles. The coating was applied to provide a 20% wg.

The immediate release microparticles (IR component) and the modified release microparticles (MR) component were combined and orally administered with water to twelve (12) fasted, healthy subjects as described in Example 4 at doses of 5.8 g, 8.7 g, 11.6 g, and 14.5 g of compound (1). The amount of compound (1) in the IR and the MR component are provided in Table 9.

TABLE 9

Content of combined release formulation.

| IR Component (g) | MR Component (g) | Dose Compound (1) (g) |
|---|---|---|
| 1.8 | 4 | 5.8 |
| 2.7 | 6 | 8.7 |

TABLE 9-continued

Content of combined release formulation.

| IR Component (g) | MR Component (g) | Dose Compound (1) (g) |
|---|---|---|
| 3.6 | 8 | 11.6 |
| 4.5 | 10 | 14.5 |

Certain of the pharmacokinetic parameters are provided in Table 10 and the γ-hydroxybutyrate pharmacokinetic profiles are shown in FIG. 6.

TABLE 10

Pharmacokinetic parameters for combined release formulations.

| (Dose) | | $T_{max}$ hr | $C_{max}$ hr × µg/mL | $AUC_{0-6}$ hr × µg/mL | $AUC_{0-12}$ hr × µg/mL | $AUC_{last}$ hr × µg/mL | $AUC_{inf}$ hr × µg/mL | CL/F L/hr | V/F L | $t_{1/2}$ hr |
|---|---|---|---|---|---|---|---|---|---|---|
| 5.8 g | Mean | 1.7 | 31 | 88 | 90 | 89 | 90 | 81 | 91 | 0.8 |
|  | CV % | 33 | 35 | 52 | 53 | 53 | 52 | 45 | 51 | 23 |
| 8.7 g | Mean | 2.3 | 61 | 185 | 194 | 193 | 195 | 52 | 79 | 0.9 |
|  | CV % | 31 | 29 | 38 | 43 | 43 | 42 | 40 | 114 | 82 |
| 11.6 g | Mean | 2.4 | 81 | 285 | 311 | 310 | 311 | 44 | 44 | 0.7 |
|  | CV % | 16 | 31 | 38 | 44 | 44 | 44 | 43 | 46 | 20 |
| 14.5 g | Mean | 2.6 | 104 | 389 | 455 | 454 | 457 | 37 | 47 | 0.8 |
|  | CV % | 32 | 24 | 33 | 41 | 42 | 42 | 38 | 47 | 44 |

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

What is claimed is:

1. A pharmaceutical composition comprising:
   an immediate release component, wherein the immediate release component comprises from 2 g of γ-((L-valyl)oxy)butanoic acid to 7 g of γ-((L-valyl)oxy)butanoic acid; and
   a modified release component, wherein the modified release component comprises from 7 g of γ-((L-valyl)oxy)butanoic acid to 15 g of γ-((L-valyl)oxy)butanoic acid.

2. The pharmaceutical composition of claim 1, wherein
   the immediate release component comprises from 10 wt % to 50 wt % of 4-((L-valyl)oxy)butanoic acid; and
   the modified release component comprises from 50 wt % to 90 wt % of 4-((L-valyl)oxy)butanoic acid,
   wherein wt % is based on the total weight of 4-((L-valyl)oxy)butanoic acid in the pharmaceutical composition.

3. The pharmaceutical composition of claim 1, wherein
   the immediate release component comprises a plurality of immediate release microparticles; and
   the immediate release microparticles comprise greater than 90 wt % of 4-((L-valyl)oxy)butanoic acid, wherein wt % is based on the total weight of the immediate release microparticles.

4. The pharmaceutical composition of claim 1, wherein
   the modified release component comprises modified release microparticles;
   the modified release microparticles comprise a core and a modified release coating surrounding the core; and
   the core comprises greater than 90 wt % of 4-((L-valyl)oxy)butanoic acid, wherein wt % is based on the total weight of the core.

5. The pharmaceutical composition of claim 1 prepared by adding to water the immediate release component and the modified release component.

6. The pharmaceutical composition of claim 1, wherein
   the immediate release component comprises a plurality of immediate release microparticles;
   the immediate release microparticles comprise:
     from 98 wt % to 99 wt % of γ-((L-valyl)oxy)butanoic acid;
     from 0.5 wt % to 1.5 wt % of a flow control agent; and
     from 0.25 wt % to 0.75 wt % of a binder, wherein,
   wt % is based on the total weight of the immediate release microparticles.

7. The pharmaceutical composition of claim 6, wherein
   the flow control agent comprises colloidal silicon dioxide; and
   the binder comprises hydroxypropyl cellulose.

8. The pharmaceutical composition of claim 4, wherein
   the core of the modified release microparticles comprises
     from 98 wt % to 99 wt % of γ-((L-valyl)oxy)butanoic acid;
     from 0.5 wt % to 1.5 wt % of a flow control agent; and
     from 0.25 wt % to 0.75 wt % of a binder, wherein,
   wt % is based on the total weight of the core; and
   the modified release coating comprises:
     from 2 wt % to 12 wt % of a plasticizer;
     from 65 wt % to 80 wt % of a water-insoluble polymer;
     from 2 wt % to 6 wt % of a water-soluble polymer; and
     from 12 wt % to 18 wt % of an antistatic agent, wherein,
   wt % is based on the total weight of the modified release coating.

9. The pharmaceutical composition of claim 8, wherein the modified release microparticles comprise from 10% wg to 40% wg of the modified release coating, wherein % wg refers to the weight of the modified release coating based on the weight of the core.

10. The pharmaceutical composition of claim 8, wherein
    the flow control agent comprises colloidal silicon dioxide;
    the binder comprises hydroxypropyl cellulose;
    the plasticizer comprises dibutyl sebacate;
    the water-insoluble polymer comprises ethyl cellulose;
    the water-soluble polymer comprises hydroxypropyl cellulose; and
    the antistatic agent comprises magnesium silicate.

11. The pharmaceutical composition of claim 8, wherein the modified release microparticles have an average particle diameter from 150 µm to 350 µm, wherein the average particle diameter is determined using laser diffraction or sieve analysis.

12. The pharmaceutical composition of claim 8, wherein
the immediate release component comprises from 4 g to 5 g of γ-((L-valyl)oxy)butanoic acid and
the modified release component comprises 9 g to 12 g of γ-((L-valyl)oxy)butanoic acid.

13. The pharmaceutical composition of claim 8, wherein
the immediate release component comprises 4.5 g of γ-((L-valyl)oxy)butanoic acid and
the modified release component comprises 10 g of γ-((L-valyl)oxy)butanoic acid.

14. The pharmaceutical composition of claim 1, wherein the immediate release microparticles have an average particle diameter from 75 μm to 450 μm, wherein the average particle diameter is determined by sieve analysis.

15. The pharmaceutical composition of claim 1, wherein
the immediate release component comprises immediate release microparticles; and
the modified release component comprises modified release microparticles.

* * * * *

UNITED STATES PATENT AND TRADEMARK OFFICE
CERTIFICATE OF CORRECTION

| | |
|---|---|
| PATENT NO. | : 11,510,892 B2 |
| APPLICATION NO. | : 17/698609 |
| DATED | : November 29, 2022 |
| INVENTOR(S) | : Daniel M. Canafax et al. |

It is certified that error appears in the above-identified patent and that said Letters Patent is hereby corrected as shown below:

In the Claims

Column 59, Lines 38-40, Claim 1 that read "$\gamma$-((L-valyl)oxy)butanoic acid to 2 g of $\gamma$-((L-valyl)oxy)butanoic acid" should read -- 4-((L-valyl)oxy)butanoic acid to 7 g of 4-((L-valyl)oxy)butanoic acid --

Column 59, Lines 43-45, Claim 1 that read "$\gamma$-((L-valyl)oxy)butanoic acid to 7 g of $\gamma$-((L-valyl)oxy)butanoic acid" should read -- 4-((L-valyl)oxy)butanoic acid to 15 g of 4-((L-valyl)oxy)butanoic acid --

Column 60, Lines 36-37, Claim 12 that read "from 98 wt % to 99 wt% of $\gamma$-((L-valyl)oxy)butanoic acid" should read -- from 98 wt % to 99 wt% of 4-((L-valyl)oxy)butanoic acid --

Column 61, Line 3, Claim 12 that reads "$\gamma$-((L-valyl)oxy)butanoic acid" should read -- 4-((L-valyl)oxy)butanoic acid --

Column 61, Line 5, Claim 13 that reads "$\gamma$-((L-valyl)oxy)butanoic acid" should read -- 4-((L-valyl)oxy)butanoic acid --

Column 61, Line 8, Claim 13 that reads "$\gamma$-((L-valyl)oxy)butanoic acid" should read -- 4-((L-valyl)oxy)butanoic acid --

Column 61, Lines 9-10, Claim 13 that reads "10 g of $\gamma$-((L-valyl)oxy)butanoic acid" should read -- 10 g of 4-((L-valyl)oxy)butanoic acid --

Signed and Sealed this
Twenty-first Day of November, 2023

Katherine Kelly Vidal
*Director of the United States Patent and Trademark Office*